United States Patent
Cantor et al.

(10) Patent No.: US 11,371,989 B2
(45) Date of Patent: Jun. 28, 2022

(54) INTRACELLULAR OSTEOPONTIN REGULATES THE LINEAGE COMMITMENT OF LYMPHOID SUBSETS

(71) Applicant: Dana-Farber Cancer Institute, Inc., Boston, MA (US)

(72) Inventors: Harvey Cantor, Boston, MA (US); Jianmei Wu Leavenworth, Hoover, AL (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 499 days.

(21) Appl. No.: 16/195,586

(22) Filed: Nov. 19, 2018

(65) Prior Publication Data

US 2019/0178884 A1 Jun. 13, 2019

Related U.S. Application Data

(62) Division of application No. 15/506,868, filed as application No. PCT/US2015/047189 on Aug. 27, 2015, now abandoned.

(60) Provisional application No. 62/042,476, filed on Aug. 27, 2014.

(51) Int. Cl.
| | |
|---|---|
| *A61K 35/00* | (2006.01) |
| *G01N 33/564* | (2006.01) |
| *C12Q 1/6883* | (2018.01) |
| *A61K 35/17* | (2015.01) |
| *G01N 33/50* | (2006.01) |

(52) U.S. Cl.
CPC ........... *G01N 33/564* (2013.01); *A61K 35/17* (2013.01); *C12Q 1/6883* (2013.01); *G01N 33/5023* (2013.01); *C12Q 2600/118* (2013.01); *C12Q 2600/158* (2013.01); *G01N 2333/4703* (2013.01); *G01N 2333/52* (2013.01); *G01N 2500/02* (2013.01); *G01N 2800/24* (2013.01)

(58) Field of Classification Search
None
See application file for complete search history.

(56) References Cited

U.S. PATENT DOCUMENTS

| | | |
|---|---|---|
| 5,552,303 A | 9/1996 | Grabstein et al. |
| 6,780,843 B2 | 8/2004 | Lin et al. |
| 7,196,170 B2 | 3/2007 | Georgopoulos et al. |
| 7,217,687 B2 * | 5/2007 | Boschert ................ A61P 43/00 514/17.7 |
| 8,709,424 B2 | 4/2014 | Schebye et al. |
| 9,783,846 B2 | 10/2017 | Olek |
| 10,548,957 B2 | 2/2020 | Cantor et al. |
| 10,596,195 B2 | 3/2020 | Cantor et al. |
| 2002/0022030 A1 | 2/2002 | Marrack et al. |
| 2004/0235720 A1 * | 11/2004 | Boschert ................ A61P 3/10 514/17.7 |
| 2007/0081991 A1 | 4/2007 | Soderstrom |
| 2007/0160578 A1 | 7/2007 | Waldmann et al. |
| 2008/0152642 A1 | 6/2008 | Georgopoulos et al. |
| 2009/0155292 A1 | 6/2009 | Santamaria et al. |
| 2009/0238791 A1 | 9/2009 | Jacques et al. |
| 2009/0324538 A1 | 12/2009 | Wong et al. |
| 2010/0260781 A1 | 10/2010 | Murray |
| 2013/0157363 A1 | 6/2013 | Kim et al. |
| 2013/0183321 A1 | 7/2013 | Smith et al. |
| 2013/0302276 A1 | 11/2013 | Cantor et al. |
| 2013/0317113 A1 | 11/2013 | Hadlock et al. |
| 2014/0220012 A1 | 8/2014 | Noelle et al. |
| 2014/0335530 A1 | 11/2014 | Drake et al. |
| 2015/0250862 A1 | 9/2015 | Cantor et al. |
| 2017/0224732 A1 | 8/2017 | Cantor et al. |
| 2017/0269076 A1 | 9/2017 | Cantor et al. |
| 2019/0192565 A1 | 6/2019 | Cantor et al. |

FOREIGN PATENT DOCUMENTS

| | | |
|---|---|---|
| WO | WO 2007/110230 A2 | 10/2007 |
| WO | WO 2009/027284 A1 | 3/2009 |
| WO | WO 2012/079000 A1 | 6/2012 |
| WO | WO 2014/039513 A2 | 3/2014 |

OTHER PUBLICATIONS

Fong et al. Osteopontin increases lung cancer cells migration via activation of the v3 integrin/FAK/Akt and NF-B-dependent pathway Lung Cancer 64 (2009) 263-270.*
Partial Supplementary European Search Report for EP 15836839.9 dated Jan. 11, 2018.
Extended European Search Report for Application No. EP 15836839.9 dated Apr. 11, 2018.
International Search Report and Written Opinion for PCT/US2015/047189 dated Feb. 2, 2016.
International Preliminary Report on Patentability for PCT/US2015/047189 dated Mar. 9, 2017.
[No Author Listed], Peripheral blood mononuclear cell From Wikipedia, the free encyclopedia; pp. 1-2 downloaded on Jul. 13, 2018.
Alvarez et al., Disruption of CD8+ Treg activity results in expansion of T follicular helper cells and enhanced antitumor immunity. Cancer Immunol Res. Mar. 2014;2(3):207-16. doi: 10.1158/2326-6066.CIR-13-0121. Epub Dec. 31, 2013.
Aoki et al., Fluorescence resonance energy transfer imaging of cell signaling from in vitro to in vivo: basis of biosensor construction, live imaging, and image processing. Dev Growth Differ. May 2013;55(4):515-22. doi:10.1111/dgd.12039. Epub Feb. 7, 2013.

(Continued)

*Primary Examiner* — Maria G Leavitt
(74) *Attorney, Agent, or Firm* — Baker Donelson

(57) ABSTRACT

Methods for diagnosing and prognosing autoimmune diseases and T cell lymphomas are provided, for example by measuring levels of intracellular osteopontin (OPN-i). Also provided are screening methods for identifying activators and inhibitors of the transcription factor Bcl6, which is involved in T cell activation/differentiation. Other aspects of the disclosure provide methods for enhancing adoptive T cell transfer.

8 Claims, 45 Drawing Sheets

Specification includes a Sequence Listing.

(56) References Cited

OTHER PUBLICATIONS

Baumjohann et al., Cutting Edge: Distinct waves of BCL6 expression during T follicular helper cell development. J Immunol. Sep. 1, 2011;187(5):2089-92. doi: 10.4049/jimmunol.1101393. Epub Jul. 29, 2011.

Bindea et al., Spatiotemporal dynamics of intratumoral immune cells reveal the immune landscape in human cancer. Immunity. Oct. 17, 2013;39(4):782-95. doi: 10.1016/j.immuni.2013.10.003.

Buback et al., Osteopontin and the skin: multiple emerging roles in cutaneous biology and pathology. Exper. Dermatol. Sep. 2009;18:750-759.

Bunting et al., New effector functions and regulatory mechanisms of BCL6 in normal and malignant lymphocytes. Curr Opin Immunol. Jun. 2013;25(3):339-46. Doi:10.1016/j.coi.2013.05.003. Epub May 30, 2013.

Buommino et al., Osteopontin: a new emerging role in psoriasis. Arch. Dermatol. Res. 2009;301:397-404.

Cantor et al., Regulation of T-helper-cell lineage development by osteopontin: the inside story. Nat Rev Immunol. Feb. 2009;9(2):137-41. Doi:10.1038/nri2460.

Carbone et al., Report of the Committee on Hodgkin's Disease Staging Classification. Cancer Res. Nov. 1971;31(11):1860-1.

Cerchietti et al., A purine scaffold Hsp90 inhibitor destabilizes BCL-6 and has specific antitumor activity in BCL-6-dependent B cell lymphomas. Nat Med. Dec. 2009;15(12):1369-76. Doi: 10.1038/nm.2059. Epub Nov. 22, 2009.

Chagan-Yasutan et al., Involvement of osteopontin and its signaling molecule CD44 in clinicopathological features of adult T cell leukemia. Leukemia Res. May 9, 2011;35(11):1484-90.

Chang et al., TRAF3 regulates the effector function of regulatory T cells and humoral immune responses. J Exp Med. Jan. 13, 2014;211(1):137-51. Doi:10.1084/jem.20131019. Epub Dec. 30, 2013.

Choi et al., Cutting edge: STAT1 is required for IL-6-mediated Bcl6 induction for early follicular helper cell differentiation. J Immunol. Apr. 1, 2013;190(7):3049-53. Doi: 10.4049/jimmunol.1203032. Epub Feb. 27, 2013.

Choi et al., ICOS receptor instructs T follicular helper cell versus effector cell differentiation via induction of the transcriptional repressor Bcl6. Immunity. Jun. 24, 2011;34(6):932-46. Doi: 10.1016/j.immuni.2011.03.023.

Chung et al., Follicular regulatory T (Tfr) cells with dual Foxp3 and Bcl6 expression suppress germinal center reactions. Nat Med. Jul. 24, 2011;17(8):983-8. Doi: 10.1038/nm.2426.

Crotty et al., Effectors and memories: Bcl-6 and Blimp-1 in T and B lymphocyte differentiation. Nat Immunol. Feb. 2010;11(2):114-20. Doi: 10.1038/ni.1837. Epub Jan. 19, 2010.

Diamandis et al., The biotin-(strept)avidin system: principles and applications in biotechnology. Clin Chem. May 1991;37(5):625-36.

Doria et al., Long-term prognosis and causes of death in systemic lupus erythematosus. Am J Med. Aug. 2006;119(8):700-6.

Gigoux et al., Inducible costimulatory promotes helper T-cell differentiation through phosphoinositide 3-kinase. Proc Natl Acad Sci U S A. Dec. 1, 2009;106(48):20371-6. Doi:10.1073/pnas.0911573106. Epub Nov. 13, 2009.

Haxhinasto et al., The AKT-Mtor axis regulates de novo differentiation of CD4+Foxp3+ cells. J Exp Med. Mar. 17, 2008;205(3):565-74. Doi:10.1084/jem.20071477. Epub Feb. 18, 2008.

Hedfors et al., Long-term proliferation and survival of in vitro-activated T cells is dependent on Interleukin-2 receptor Signaling but not on the high-affinity IL-2R. Scand J Immunol. Nov. 2003;58(5):522-31.

Huang et al., Gene expression profiles in BCL11B-siRNA treated malignant T cells. J. Hermatol Oncol. May 15, 2011;4(1, 23):1-6.

Huang et al., Lineage-specific functions of Bcl-6 in immunity and inflammation are mediated by distinct biochemical mechanisms. Nat Immunol. Apr. 2013;14(4):380-8. Doi: 10.1038/ni.2543. Epub Mar. 3, 2013.

Inoue et al., Intracellular osteopontin (iOPN) and immunity. Immunol Res. Apr. 2011;49(1-3):160-72. Doi: 10.1007/s12026-010-8179-5.

Johnston et al., Bcl6 and Blimp-1 are reciprocal and antagonistic regulators of T follicular helper cell differentiation. Science. Aug. 21, 2009;325(5943):1006-10. Doi: 10.1126/science.1175870. Epub Jul. 16, 2009.

June, Principles of adoptive T cell cancer therapy. J Clin Invest. May 2007;117(5):1204-12.

Kaleta, Role of Osteopontin in Systemic Lupus Erythematosus. Arch Immunol. Ther. Exp. Dec. 1, 2014;62:475-482.

Kalos et al., Adoptive T cell transfer for cancer immunotherapy in the era of synthetic biology. Immunity. Jul. 25, 2013;39(1):49-60. doi:10.1016/j.immuni.2013.07.002.

Kaluza et al., Improving the outcome of adoptive cell transfer by targeting tumor escape. Oncoimmunollogy. Jan. 2013;2(1):e22059-1-3.

Kang et al., MicroRNAs of the miR-17~92 family are critical regulators of T(FH) differentiation. Nat Immunol. Aug. 2013;14(8):849-57. doi: 10.1038/ni.2648. Epub Jun. 30, 2013.

Karttunen et al., Detection of rare antigen-presenting cells by the lacZ T-cell activation assay suggests an expression cloning strategy for T-cell antigens. Proc Natl Acad Sci U S A. Jul. 1, 1992;89(13):6020-4.

Kerfoot et al., Germinal center B cell and T follicular helper cell development initiates in the interfollicular zone. Immunity. Jun. 24, 2011;34(6):947-60. doi:10.1016/j.immuni.2011.03.024.

Keszei et al., Expansion of an osteopontin-expressing T follicular helper cell subset correlates with autoimmunity in B6.Sle1b mice and is suppressed by the H1-isoform of the Slamf6 receptor. FASEB J. Aug. 2013;27(8):3123-31. doi: 10.1096/fj.12-226951. Epub Apr. 29, 2013.

Kim et al., Inhibition of follicular T-helper cells by CD8(+) Treg is essential for self tolerance. Nature. Sep. 16, 2010;467(7313):328-32. doi: 10.1038/nature09370.

Krönke et al., Lenalidomide causes selective degradation of IKZF1 and IKZF3 in multiple myeloma cells. Science. Jan. 17, 2014;343(6168):301-5. doi: 10.1126/science.1244851. Epub Nov. 29, 2013.

Leavenworth et al., A p85α-osteopontin axis couples the receptor ICOS to sustained Bcl-6 expression by follicular helper and regulatory T cells. Nat Immunol. Jan. 2015;16(1):96-106. doi: 10.1038/ni.3050. Epub Dec. 1, 2014.

Leavenworth et al., Amelioration of arthritis through mobilization of peptide-specific CD8+regulatory T cells. J Clin Invest. Mar. 2013;123(3):1382-9. doi: 10.1172/JCI66938. Epub Feb. 8, 2013.

Lequin, Enzyme immunoassay (EIA)/enzyme-linked immunosorbent assay (ELISA). Clin Chem. Dec. 2005;51(12):2415-8. Epub Sep. 22, 2005.

Lim et al., Parkin mediates nonclassical, proteasomal-independent ubiquitination of synphilin-1: implications for Lewy body formation. J Neurosci. Feb. 23, 2005;25(8):2002-9.

Lindqvist et al., Prognostic laboratory markers of joint damage in rheumatoid arthritis. Ann Rheum Dis. Feb. 2005;64(2):196-201. Epub Sep. 30, 2004.

Linterman et al., Foxp3+ follicular regulatory T cells control T follicular helper cells and the germinal center reponse. Nat Med. Jul. 24, 2011;17(8):975-82. doi: 10.1038/nm.2425.

Ma et al., Human T follicular helper (Tfh) cells and disease. Immunol Cell Biol. Jan. 2014;92(1):64-71. doi: 10.1038/icb.2013.55. Epub Oct. 22, 2013.

Mrowietz et al., Definition of treatment goals for moderate to severe psoriasis: a European consensus. Arch Dermatol Res. Jan. 2011;303(1):1-10. doi: 10.1007/s00403-010-1080-1. Epub Sep. 21, 2010.

Münst et al., Engineering cell-permeable protein. J Vis Exp. Dec. 28, 2009;(34). pii: 1627. doi: 10.3791/1627.

Nakayamada et al.,Type I IFN induces binding of STAT1 to Bc16: divergent roles of STAT family transcription factors in the T follicular helper cell genetic program. J Immunol. Mar. 1, 2014;192(5):2156-66. doi: 10.4049/jimmunol.1300675. Epub Jan. 31, 2014.

Nurieva et al., Bcl6 mediates the development of T follicular helper cells. Science. Aug. 21, 2009;325(5943):1001-5. doi: 10.1126/science.1176676. Epub Jul. 23, 2009.

(56) References Cited

OTHER PUBLICATIONS

Obenauer et al., Scansite 2.0: Proteome-wide prediction of cell signaling interactions using short sequence motifs. Nucleic Acids Res. Jul. 1, 2003;31(13):3635-41.
Park et al., The regulatory subunits of PI3K, p85alpha and p85beta, interact with XBP-1 and increase its nuclear translocation. Nat Med. Apr. 2010;16(4):429-37. doi: 10.1038/nm.2099. Epub Mar. 28, 2010.
Patarca et al., Differential induction of interferon gamma gene expression after activation of CD4+ T cells by conventional antigen and Mls superantigen. Proc Natl Acad Sci U S A. Apr. 1, 1991;88(7):2736-9.
Patarca et al., Dysregulated expression of the T cell cytokine Eta-1 in CD4-8- lymphocytes during the development of murine autoimmune disease. J Exp Med. Oct. 1, 1990;172(4):1177-83.
Powell et al., Expression profiling of a hemopoietic cell survival transcriptome implicates osteopontin as a functional prognostic factor in AML. Blood. Nov. 26, 2009;114(23):4859-70. doi:10.1182/blood-2009-02-204818. Epub Oct. 5, 2009.
Roifman et al., Evidence of endothelial dysfunction in patients with inflammatory bowel disease. Clin Gastroenterol Hepatol. Feb. 2009;7(2):175-82. doi: 10.1016/j.cgh.2008.10.021. Epub Oct. 30, 2008.
Rolf et al., Phosphoinositide 3-kinase activity in T cells regulates the magnitude of the germinal center reaction. J Immunol. Oct. 1, 2010;185(7):4042-52. doi: 10.4049/jimmunol.1001730. Epub Sep. 8, 2010.
Rolf et al., Signaling pathways in T follicular helper cells. J Immunol. Jun. 15, 2010;184(12):6563-8. doi: 10.4049/jimmunol.1000202.
Rullo et al., Plasma levels of osteopontin identify patients at risk for organ damage in systemic lupus erythematosus. Arthritis Res Ther. Jan. 23, 2013;15(1):R18. doi: 10.1186/ar4150.
Sage et al., PD-1 controls Lymph Node and Blood T Follicular Regulatory Cells. Nat Immunol. Feb. 2013;14(2):152-61. doi: 10.1038/ni.2496. Epub Dec. 16, 2012.
Samitas et al., Osteopontin expression and relation to disease severity in human asthma. Eur Respir J. Feb. 2011;37(2):331-41. doi: 10.1183/09031936.00017810. Epub Jun. 18, 2010.
Sato et al., Osteopontin/Eta-1 upregulated in Crohn's disease regulates theTh1 immune response. Gut. Sep. 2005;54(9):1254-62.
Schafer et al., Microglia sculpt postnatal neural circuits in an activity and complementdependent manner. Neuron. May 24, 2012;74(4):691-705. doi: 10.1016/j.neuron.2012.03.026.
Shinohara et al., Alternative translation of osteopontin generates intracellular and secreted isoforms that mediate distinct biological activities in dendritic cells. Proc Natl Acad Sci U S A. May 20, 2008;105(20):7235-9. doi: 10.1073/pnas.0802301105. Epub May 14, 2008.
Shinohara et al., Engagement of the type I interferon receptor on dendritic cells inhibits T helper 17 cell development: role of intracellular osteopontin. Immunity. Jul. 18, 2008;29(1):68-78. doi:10.1016/j.immuni.2008.05.008.
Shinohara et al., T-bet-dependent expression of osteopontin contributes to T cell polarization. Proc Natl Acad Sci U S A. Nov. 22, 2005;102(47):17101-6. Epub Nov. 14, 2005.
Tafuri et al., ICOS is essential for effective T-helper-cell responses. Nature. Jan. 4, 2001;409(6816):105-9.
Tey et al., Adoptive T-cell transfer in cancer immunotherapy. Immunol Cell Biol. Jun. 2006;84(3):281-9.
Thompson et al., Prognosis and prognostic factors in inflammatory bowel disease. Saudi J Gastroenterol. Sep. 1995;1(3):129-37.
Tsang et al., Multiple sclerosis—diagnosis, management and prognosis. Aust Fam Physician. Dec. 2011;40(12):948-55.
Tun et al., Pathway analysis of primary central nervous system lymphoma. Blood. Mar. 15, 2008;111(6):3200-10. doi: 10.1182/blood-2007-10-119099. Epub Jan. 9, 2008.
Uede et al., Osteopontin, intrinsic tissue regulator of intractable inflammatory diseases. Pathol. Int. May 2011;61:265-280.
Wieczorek et al., Genetically modified T cells for the treatment of malignant disease. Transfus Med Hemother. Dec. 2013;40(6):388-402. doi: 10.1159/000357163. Epub Nov. 29, 2013.
Winnay et al., A Novel Interaction Between the Regulatory Subunit of PI 3-Kinase and X-box Binding Portein-1 Modulates the Unfolded Protein Response. Nat Med. Apr. 2010;16(4):438-45. doi: 10.1038/nm.2121. Epub Mar. 28, 2010.
Wong et al., Elevation of plasma osteopontin concentration is correlated with disease activity in patients with systemic lupus erythematosus. Rheumatology (Oxford). May 2005;44(5):602-6. Epub Feb. 10, 2005.
Yaffe et al., The structural basis for 14-3-3:phosphopeptide binding specificity. Cell. Dec. 2,6 1997;91(7):961-71.
Yawn, Factors accounting for asthma variability: achieving optimal symptom control for individual patients. Prim Care Respir J. Sep. 2008;17(3):138-47. doi: 10.3132/pcrj.2008.00004.
Yu et al.., Regulation of the p85/p110 phosphatidylinositol 3'-kinase: stabilization and inhibition of the p110alpha catalytic subunit by the p85 regulatory subunit. Mol Cell Biol. Mar. 1998;18(3):1379-87.
Zeug et al., Quantitative intensity-based FRET approaches—a comparative snapshot. Biophys J. Nov. 7, 2012;103(9):1821-7.doi:10.1016/j.bpj.2012.09.031.
Zhao et al., The oncogenic properties of mutant p110alpha and p110beta phosphatidylinositol 3-kinases in human mammary epithelial cells. Proc Natl Acad Sci U S A. Dec. 20, 2005;102(51):18443-8. Epub Dec. 8, 2005.
PCT/US2015/047189, Feb. 2, 2016, International Search Report and the Written Opinion.
PCT/US2015/047189, Mar. 9, 2017, International Preliminary Report on Patentability.
EP 15836839.9, Jan. 11, 2018, Partial Supplementary European Search Report.
EP 15836839.9, Apr. 11, 2018, Extended European Search Report.

\* cited by examiner

Stable Bcl6 expression
Functional $T_{FH}$ and $T_{FR}$ differentiation

Primary response

| Function Annotation | p-value | # Molecules |
|---|---|---|
| quantity of T lymphocytes | 3.89E-14 | 26 |
| quantity of B lymphocytes | 7.06E-12 | 19 |
| proliferation of T lymphocytes | 8.68E-12 | 24 |
| systemic autoimmune syndrome | 2.65E-11 | 31 |
| activation of T lymphocytes | 3.02E-10 | 17 |
| production of antibody | 1.03E-09 | 16 |
| quantity of immunoglobulin | 4.11E-09 | 15 |
| quantity of IgG | 6.50E-09 | 13 |
| cell death of T lymphocytes | 9.67E-09 | 15 |
| differentiation of T lymphocytes | 4.36E-08 | 15 |
| function of T lymphocytes | 7.55E-08 | 13 |
| Rheumatic Disease | 4.56E-07 | 25 |
| expansion of T lymphocytes | 5.32E-07 | 9 |
| proliferation of B lymphocytes | 8.67E-07 | 12 |
| quantity of helper T lympocytes | 9.26E-07 | 10 |
| immune response of T lymphocytes | 1.03E-06 | 8 |
| quantity of IgG1 | 3.30E-06 | 8 |
| rheumatoid arthritis | 5.88E-06 | 18 |
| quantity of IgG2a | 6.22E-06 | 7 |
| differentiation of naive T lymphocytes | 1.95E-05 | 5 |
| proliferation of helper T lymphocytes | 7.75E-05 | 5 |
| differentiation of helper T lymphocytes | 1.45E-04 | 7 |

Fig. 13B

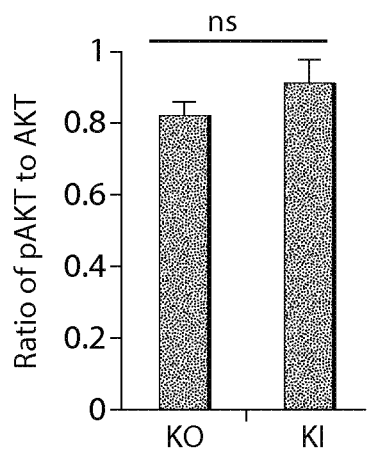
Fig. 14C
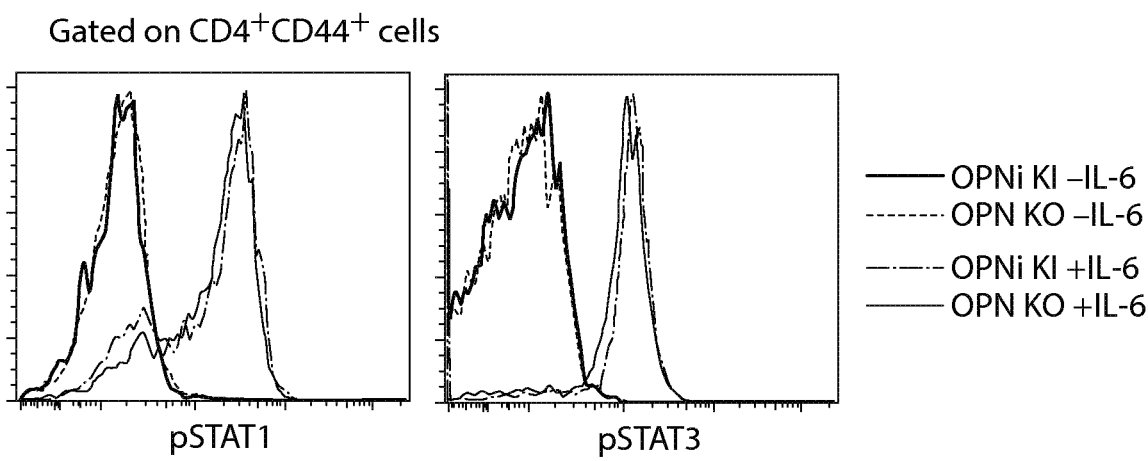
Fig. 14D
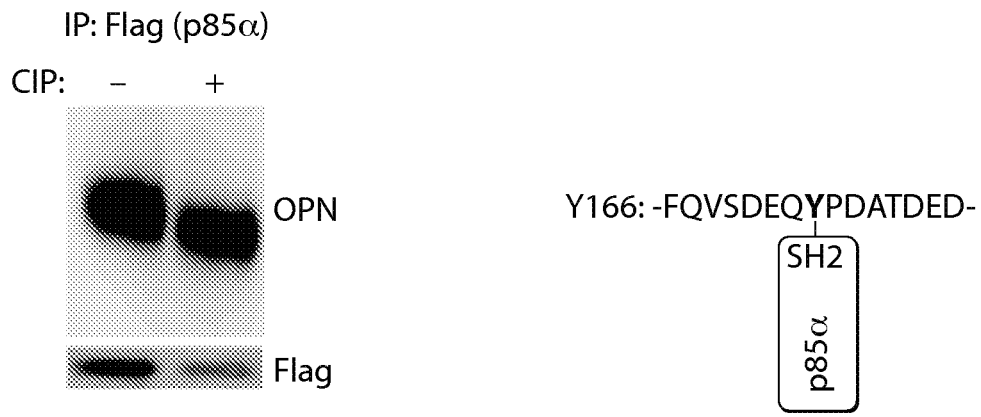
Fig. 14E
Fig. 14F

INTRACELLULAR OSTEOPONTIN REGULATES THE LINEAGE COMMITMENT OF LYMPHOID SUBSETS

RELATED APPLICATIONS

This application is a Division of U.S. application Ser. No. 15/506,868, filed Feb. 27, 2017, now abandoned, entitled "INTRACELLULAR OSTEOPONTIN REGULATES THE LINEAGE COMMITMENT OF LYMPHOID SUBSETS", which is a national stage filing under 35 U.S.C. 371 of International Patent Application Serial No. PCT/US2015/047189, filed Aug. 27, 2015, entitled "INTRACELLULAR OS TEO PONTIN REGULA TES THE LINEAGE COMMITMENT OF LYMPHOID SUBSETS", which application claims the benefit under 35 U.S.C. § 119(e) of U.S. provisional application U.S. Ser. No. 62/042,476, filed Aug. 27, 2014, the entire contents of each of which are incorporated herein by reference in their entirety.

FEDERALLY SPONSORED RESEARCH

This invention was made with government support under grant number R01 AI048125 awarded by the National Institutes of Health. The government has certain rights in the invention.

BACKGROUND OF THE INVENTION

The generation of protective antibodies by B cells following infection or vaccination requires 'help' from CD4+ T cells. T follicular helper ($T_{FH}$) and T follicular regulatory ($T_{FR}$) cells are specialized CD4+ T cell subsets that induce and repress the activation and differentiation of B cells into immunoglobulin (Ig) secreting cells, respectively. Bcl6, a proto-oncoprotein and a transcriptional repressor belonging to the BTB-POZ family, has been identified as the central transcription factor (TF) that controls both $T_{FH}$ differentiation and associated GC responses[1-3] as well as $T_{FR}$ differentiation and their suppressive activity. As such, appropriate control of $T_{FH}$ and $T_{FR}$ cell generation and function is essential to human health as Bcl6 deficiency can result in increased susceptibility to chronic infection, while excessive expression is associated with autoimmunity and lymphocytic transformation. Furthermore, an understanding of the activation of these cells may be invaluable for the diagnosis and prognosis of immune related disorders, and for identifying modulators which can be used to promote or inhibit germinal center activation, for example in the treatment of immune related disorders.

SUMMARY OF THE INVENTION

The present disclosure relates, in some aspects, to the development of strategies based on in vivo and in vitro activation and differentiation of the follicular CD4+ helper T ($T_{FH}$) cells and regulatory T ($T_{FR}$) cells for the diagnosis, prognosis, and treatment of autoimmune diseases. Other aspects relate to novel screening methods for identifying compounds useful for treating autoimmune diseases.

According to some aspects, the present disclosure provides a method for diagnosing an autoimmune disease, the method comprising: selecting a subject suspected of having an autoimmune disease; measuring expression level of intracellular osteopontin (OPN-i) in a follicular helper T ($T_{FH}$) cells sample obtained from the subject; and identifying the subject as having an autoimmune disease when the expression level of OPN-i is increased as compared to a control level.

According to some aspects, the present disclosure provides a method for prognosing an autoimmune disease, the method comprising: selecting a subject having or suspected of having an autoimmune disease; measuring expression level of intracellular osteopontin (OPN-i) in a follicular helper T ($T_{FH}$) cells sample obtained from the subject; and identifying the subject as having a less favorable prognosis when the expression level of OPN-i is increased as compared to a control level.

In some embodiments, the autoimmune disease is selected from the group consisting of systemic lupus erythematosus (SLE), psoriasis, multiple sclerosis, Crohn's disease, inflammatory bowel disease (IBD), asthma, rheumatoid arthritis, and psoriatic arthritis.

In some embodiments, the autoimmune disease is SLE. In another embodiment, the less favorable prognosis of SLE is (a) a higher risk of developing CNS involvement, (b) a higher risk of progressive renal failure and/or (c) a higher risk of cardiovascular diseases, pleurisy and/or abnormalities in the blood.

According to some aspects, the present disclosure provides a method for diagnosing T cell lymphomas, the method comprising: selecting a subject suspected of having T cell lymphomas; measuring expression level of intracellular osteopontin (OPN-i) in a follicular helper T ($T_{FH}$) cells sample obtained from the subject; and identifying the subject as having T cell lymphomas when the expression level of OPN-i is increased as compared to a control level.

According to some aspects, the present disclosure provides a method for prognosing T cell lymphomas, the method comprising: selecting a subject having or suspected of having T cell lymphomas; measuring expression level of intracellular osteopontin (OPN-i) in a follicular helper T ($T_{FH}$) cells sample obtained from the subject; and identifying the subject as having a less favorable prognosis when the expression level of OPN-i is increased as compared to a control level.

In some embodiments, the follicular helper T ($T_{FH}$) cells are isolated from peripheral blood mononuclear cells (PBMC).

In some embodiments, the follicular helper T ($T_{FH}$) cells are isolated using immunofluorescence or fluorescence activated cell sorting (FACS).

In some embodiments, the OPN-i mRNA or protein expression level is measured. In some embodiments the OPN-i mRNA expression level is measured using quantitative RT-PCR. In other embodiments, the OPN-i protein expression level is measured using Western blot or enzyme-linked immunosorbent assay (ELISA).

In some embodiments, the invention is a method further comprising: measuring expression level of inducible costimulator (ICOS) receptor in the follicular helper T ($T_{FH}$) cells sample; and identifying the subject as having an autoimmune disease or as having a less favorable prognosis when the expression levels of both OPN-I and ICOS are increased as compared to a control level for each of OPN-I and ICOS.

According to some aspects, the present disclosure provides a method for identifying Bcl6 inhibitors comprising: combining regulatory p85α subunit of phosphatidylinositol-3-OH kinase or a fragment thereof with OPN-i or fragment thereof in presence or absence of a test compound; labelling p85α or fragment thereof with a fluorescence donor and labelling OPN-i or fragment thereof with a fluorescent acceptor, wherein binding of OPN-i to p-85α is detected by proximity-based luminescence detection; and identifying the test compound as a Bcl6 inhibitor when the proximity-based luminescence detection signal is decreased in the presence of the test compound relative to the signal in the absence of the test compound.

In some embodiments, the proximity-based luminescence detection is selected from the group consisting of fluorescence resonance energy transfer ("FRET"), luminescence resonance energy transfer ("LRET"), fluorescence cross-correlation spectroscopy ("FCCS"), scintillation proximity ("SPA"), chemiluminescence energy transfer ("CRET"), bioluminescence energy transfer ("BRET"), and excimer formation.

In some embodiments, the p85α subunit is labeled with a fluorescence acceptor, and OPN-i is labeled with a fluorescence donor. In another embodiment, the p85α subunit or the fragment thereof is fused to glutathione-S-transferase (GST); and the OPN-i or the fragment thereof is linked to biotin.

In some embodiments, the p85α subunit or the fragment thereof is labelled with a fluorescence donor or acceptor using an anti-GST antibody; and the OPN-i or the fragment thereof is labelled with a fluorescent acceptor or donor using streptavidin. In another embodiment, the p85α subunit or the fragment thereof is linked to biotin; and the OPN-i or the fragment thereof is fused to glutathione-S-transferase (GST).

In some embodiments, the p85α subunit or the fragment thereof is labelled with a fluorescence donor or acceptor using streptavidin; and the OPN-i or the fragment thereof is labelled with a fluorescent acceptor or donor using an anti-GST antibody.

In some embodiments, the fragment of p85α subunit comprises amino acid residues 333-428 or amino acid residues 624-718 of SEQ ID NO:1

In some embodiment, the fragment of OPN-i comprises SEQ ID NO: 2.

In some embodiments, the p85α subunit and/or OPN-i are linked to a solid substrate. In some embodiments, the p85α subunit and/or OPN-i are linked to the solid substrate via a biotin/avidin interaction.

In some embodiments, the solid substrate is a microtiter plate, membrane, or bead.

In some embodiments, the method further comprises performing an assay to determine whether the identified Bcl6 inhibitor compound binds to OPN-i.

In some embodiments, the method further comprises performing an assay to determine whether the identified Bcl6 inhibitor compound binds to p85α or fragment thereof.

According to some aspects, the present disclosure provides a method for identifying Bcl6 activators comprising: combining regulatory p85α subunit of phosphatidylinositol-3-OH kinase or a fragment thereof with OPN-i or fragment thereof in presence or absence of a test compound; labelling p85α or fragment thereof with a fluorescence donor and labelling OPN-i or fragment thereof with a fluorescent acceptor, wherein binding of OPN-i to p85α is detected by proximity-based luminescence detection; and identifying the test compound as a Bcl6 activator when the proximity-based luminescence detection signal is increased in the presence of the test compound relative to the signal in the absence of the test compound.

In some embodiments, the proximity-based luminescence detection is selected from the group consisting of fluorescence resonance energy transfer ("FRET"), luminescence resonance energy transfer ("LRET"), fluorescence cross-correlation spectroscopy ("FCCS"), scintillation proximity ("SPA"), chemiluminescence energy transfer ("CRET"), bioluminescence energy transfer ("BRET"), and excimer formation.

In some embodiments, the p85α subunit is labeled with a fluorescence acceptor, and OPN-i is labeled with a fluorescence donor.

In some embodiments, the p85α subunit or the fragment thereof is fused to glutathione-S-transferase (GST); and the OPN-i or the fragment thereof is linked to biotin.

In some embodiments, the p85α subunit or the fragment thereof is labelled with a fluorescence donor or acceptor using an anti-GST antibody; and the OPN-i or the fragment thereof is labelled with a fluorescent acceptor or donor using streptavidin.

In some embodiments, the p85α subunit or the fragment thereof is linked to biotin; and the OPN-i or the fragment thereof is fused to glutathione-S-transferase (GST). In some embodiments, the p85α subunit or the fragment thereof is labelled with a fluorescence donor or acceptor using streptavidin; and the OPN-i or the fragment thereof is labelled with a fluorescent acceptor or donor using an anti-GST antibody.

In some embodiments, the fragment of p85α subunit comprises amino acid residues 333-428 or amino acid residues 624-718 of SEQ ID NO:1

In some embodiment, the fragment of OPN-i comprises SEQ ID NO: 2.

In some embodiments, the p85α subunit and/or OPN-i are linked to a solid substrate. In some embodiments the p85α subunit and/or OPN-i are linked to the solid substrate via a biotin/avidin interaction. In other embodiments the solid substrate is a microtiter plate, membrane, or bead.

According to some aspects, the present disclosure provides a method for identifying Bcl6 inhibitors comprising: combining OPN-i or a fragment thereof with Bcl6 RD2 domain in presence or absence of a test compound; labelling OPN-i or fragment thereof with a fluorescence donor and labelling Bcl6 RD2 domain with a fluorescent acceptor; detecting binding of OPN-i to Bcl6 RD2 domain by proximity-based luminescence detection; performing an assay to determine whether the test compound binds to OPN-i; and identifying the test compound as a Bcl6 inhibitor when the proximity-based luminescence detection signal is decreased in the presence of the test compound relative to the signal in the absence of the test compound, and the test compound binds to OPN-i.

In some embodiments, the proximity-based luminescence detection is selected from the group consisting of fluorescence resonance energy transfer ("FRET"), luminescence resonance energy transfer ("LRET"), fluorescence cross-correlation spectroscopy ("FCCS"), scintillation proximity ("SPA"), chemiluminescence energy transfer ("CRET"), bioluminescence energy transfer ("BRET"), and excimer formation.

In some embodiments, the OPN-i is labeled with a fluorescence acceptor, and the Bcl6 RD2 domain is labeled with a fluorescence donor.

In some embodiments, the Bcl6 RD2 domain is fused to glutathione-S-transferase (GST); and the OPN-i or the fragment thereof is linked to biotin. In other embodiments, the Bcl6 RD2 domain is labelled with a fluorescence donor or acceptor using an anti-GST antibody; and the OPN-i or the fragment thereof is labelled with a fluorescent acceptor or donor using streptavidin.

In some embodiment, the Bcl6 RD2 domain is linked to biotin; and the OPN-i or the fragment thereof is fused to glutathione-S-transferase (GST). In some embodiments, the Bcl6 RD2 domain is labelled with a fluorescence donor or acceptor using streptavidin; and the OPN-i or the fragment thereof is labelled with a fluorescent acceptor or donor using an anti-GST antibody.

In some embodiments, the fragment of OPN-i comprises SEQ ID NO: 2.

In some embodiments, the OPN-i and/or the Bcl6 RD2 domain are linked to a solid substrate. In some embodiments, OPN-i and/or the Bcl6 RD2 domain are linked to the solid substrate via a biotin/avidin interaction. In other embodiments, the solid substrate is a microtiter plate, membrane, or bead.

According to some aspects, the present disclosure provides a method for identifying Bcl6 activators comprising: combining OPN-i or a fragment thereof with Bcl6 RD2 domain in presence or absence of a test compound; labelling OPN-i or fragment thereof with a fluorescence donor and labelling Bcl6 RD2 domain with a fluorescent acceptor, wherein binding of OPN-i to Bcl6 RD2 domain is detected by proximity-based luminescence detection; and identifying the test compound as a Bcl6 inhibitor when the proximity-based luminescence detection signal is increased in the presence of the test compound relative to the signal in the absence of the test compound.

In some embodiments, the proximity-based luminescence detection is selected from the group consisting of fluorescence resonance energy transfer ("FRET"), luminescence resonance energy transfer ("LRET"), fluorescence cross-correlation spectroscopy ("FCCS"), scintillation proximity ("SPA"), chemiluminescence energy transfer ("CRET"), bioluminescence energy transfer ("BRET"), and excimer formation.

In some embodiments, the OPN-i is labeled with a fluorescence acceptor, and the Bcl6 RD2 domain is labeled with a fluorescence donor.

In some embodiments, the Bcl6 RD2 domain is fused to glutathione-S-transferase (GST); and the OPN-i or the fragment thereof is linked to biotin.

In some embodiments, the Bcl6 RD2 domain is labelled with a fluorescence donor or acceptor using an anti-GST antibody; and the OPN-i or the fragment thereof is labelled with a fluorescence acceptor or donor using streptavidin.

In some embodiments, the Bcl6 RD2 domain is linked to biotin; and the OPN-i or the fragment thereof is fused to glutathione-S-transferase (GST). In another embodiment the Bcl6 RD2 domain is labelled with a fluorescence donor or acceptor using streptavidin; and the OPN-i or the fragment thereof is labelled with a fluorescent acceptor or donor using an anti-GST antibody.

In some embodiments, the fragment of OPN-i comprises SEQ ID NO: 2.

In some embodiments, the OPN-i and/or the Bcl6 RD2 domain are linked to a solid substrate. In other embodiments the OPN-i and/or the Bcl6 RD2 domain are linked to the solid substrate via a biotin/avidin interaction. In another embodiment the solid substrate is a microtiter plate, membrane, or bead.

According to some aspects, the present disclosure provides a method for identifying Bcl6 inhibitors comprising: combining cells expressing fluorescently labelled Bcl6 fusion protein and p85α subunit with OPN-i or fragment thereof in the presence or absence of a test compound; and identifying the test compound as a Bcl6 inhibitor when fluorescence signal is decreased in the presence of the test compound relative to the signal in the absence of the test compound.

According to some aspects, the present disclosure provides a method for identifying Bcl6 modulators comprising: combining OPN-i or a fragment thereof with Bcl6 RD2 domain in presence or absence of a test compound, wherein binding of OPN-i to Bcl6 RD2 domain is detected by ELISA-based assay; and identifying the test compound as a Bcl6 modulator when the ELISA signal is decreased or increased in the presence of the test compound relative to the signal in the absence of the test compound.

According to some aspects, the present disclosure provides a method of enhancing adoptive T cell transfer in a subject, said method comprising isolating CD4+ T cells from peripheral blood from a subject in need thereof; transducing the isolated CD4+ T cells by contacting the CD4+ T cells with retroviral vectors expressing OPN-i; expanding the transduced CD4+ T cells by growing them in a culture medium until the number of transduced CD4+ T cells increases by at least 5%; and administering the expanded transduced CD4+ T cells to the subject.

In some embodiments, the T cell is an activated T cell. In some embodiments the T cells are modified to express a chimeric antigen receptor (CAR).

In some embodiments, the method further comprises transducing the isolated CD4+ T cells by contacting the CD4+ T cells with retroviral vectors expressing p85α.

According to some aspects, the present disclosure provides a method of enhancing adoptive T cell transfer in a subject, said method comprising isolating CD4+ T cells from peripheral blood from a subject in need thereof; treating the isolated CD4+ T cells with cell-permeable OPN-i or fragments thereof; expanding the treated CD4+ T cells by growing them in a culture medium until the number of treated CD4+ T cells increases by at least 5%; and administering the expanded treated CD4+ T cells to the subject.

In some embodiments, the T cell is an activated T cell.

In some embodiments, the T cells is modified to express a chimeric antigen receptor (CAR).

In some embodiments, the cell-permeable OPN-i or fragments thereof comprise OPN-i or fragments thereof fused to protein transduction domains.

In some embodiments, the protein transduction domain is selected from the group consisting of transportan, AntHD, TAT, VP22, cationic prion protein domains and functional fragments thereof.

Each of the embodiments and aspects of the invention can be practiced independently or combined. Also, the phraseology and terminology used herein is for the purpose of description and should not be regarded as limiting. The use of "including", "comprising", or "having", "containing", "involving", and variations thereof herein, is meant to encompass the items listed thereafter and equivalents thereof as well as additional items.

These and other aspects of the inventions, as well as various advantages and utilities will be apparent with reference to the Detailed Description. Each aspect of the invention can encompass various embodiments as will be understood.

All documents identified in this application are incorporated in their entirety herein by reference.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 2A depicts the quantitative RT-PCR analysis of Spp1 mRNA (left), OPN and actin protein levels (right) expressed by the indicated CD4$^+$ T cell populations sorted (as shown in FIG. 10) from B6 mice 3 days after immunization with KLH in CFA. Spp1 expression was normalized to that of the Rps18 control and results are presented relative to that of naïve T cells ($T_N$). FIG. 2B shows the levels of IgG and IgG1 after WT, OPN KO, and OPN-i KI mice expressing the OT-II TCR were immunized with NP-OVA in CFA for 10 days followed by boosting for another 7 days. Serum titers of anti-NP23 (total) and anti-NP4 (high affinity) IgG and IgG1 are shown. FIG. 2C is a series of representative FACS plots of $T_{FH}$ (Foxp3$^-$PD1$^+$CXCR5$^+$), $T_{FR}$ (Foxp3$^+$PD1$^+$CXCR5$^+$), and GC B cells in FIG. 2B are shown. FIG. 2D depicts the numbers of $T_{FH}$, $T_{FR}$ and GC B cells in FIG. 2C. n=5 per group. , P<0.01, *, P<0.001, ns, no significance. Data shown are representative of at least three independent experiments.

FIG. 3A consists of representative FACS plots of $T_{FH}$ (Foxp3$^-$PD1$^+$CXCR5$^+$) and GC B cells at d7. Naïve CD4$^+$ T cells from the indicated OT-II mice were transferred into Rag2$^{-/-}$Prf1$^{-/-}$ hosts along with OPN-i KI B cells followed by immunization with NP-OVA in CFA at day 0 and boosting with NP-OVA in IFA at day 10. FIG. 3B depicts serum titers of NP-specific IgG and IgG1 that were analyzed at day 17. n=4 per group. FIG. 3C includes representative FACS plots of $T_{FR}$ (Foxp3$^+$PD1$^+$CXCR5$^+$) cells at day 7. Purified CD25$^+$ CD4$^+$ T cells from the indicated mouse strains were transferred into TCRα$^{-/-}$ hosts followed by immunization with NP-KLH in CFA. FIG. 3D shows titers of NP-specific total IgG (α-NP23) and high-affinity IgG (α-NP4) at d14 in immunized Rag2$^{-/-}$Prf1$^{-/-}$ mice given KI or KO $T_{FH}$ cells (5×10$^4$) with or without KI or KO $T_{FR}$ cells (2.5×10$^4$) and GL-7$^-$B cells (1×10$^5$) from KLH-immunized mice. All Rag2$^{-/-}$ Prf1$^{-/-}$ recipients were immunized with NP-KLH in CFA. FIG. 3E consists of representative FACS plots of GC B cells at d22 in FIG. 3D. FIG. 3F depicts titers of NP-specific total IgG at day 11 in immunized Rag2$^{-/-}$Prf1$^{-/-}$ mice given KI or KO $T_{FH}$ cells with or without KI or KO $T_{FR}$ cells (2.5×10$^4$) at different ratios and GL-7$^-$B cells (1×10$^5$) from KLH-immunized mice. Data are representative of three (FIG. 3A-3C) and two (FIG. 3D-3F) independent experiments.

FIG. 4A is a kinetic analysis of Bcl6 expression in the indicated CD4$^+$ $T_H$ subsets ($T_{FH}$: CD4$^+$CD44$^+$CXCR5$^+$PD-1$^+$Foxp3$^-$; $T_{FR}$: CD4$^+$CD44$^+$CXCR5$^+$PD-1$^+$Foxp3$^+$; Non-$T_{FH}$: CD4$^+$CD44$^{hi}$CXCR5$^{lo}$PD-1$^{lo}$Foxp3$^-$) from each mouse strain at the indicated time points after immunization with KLH in CFA. Overlaid histograms of Bcl6 (FIG. 4A) and quantitation of Bcl6 MFI (FIG. 4B) are shown. FIG. 4C consists of representative FACS plots of $T_{FH}$ and $T_{FR}$ cells at the indicated time points in FIG. 4A. In FIG. 4D, the frequency of $T_{FH}$ and $T_{FR}$ cells in (c) is plotted. n=3 per group. In FIG. 4E, quantitative kinetic RT-PCR analysis of Spp1 mRNA levels in indicated CD4$^+$ T cell populations sorted (as shown in FIG. 10) from OPN-i KI mice at the indicated time points after immunization with KLH in CFA is shown. Spp1 expression was normalized to that of the Rps18 control and results are presented relative to that of Treg at day 3. Data are representative of two independent experiments.

FIG. 5A shows the relative Spp1 expression after purified naïve CD62L$^+$ CD4$^+$ T cells from B6 mice were stimulated with anti-CD3 and anti-CD28 for 2 d followed by resting overnight before 20 minute incubation with the indicated Ab and then cross-linking with goat anti-hamster Ab for 8 hours or 24 hours. Quantitative RT-PCR analysis of Spp1 RNA and expression was normalized to that of the Rps18 control and results are presented relative to that of isotype hamster IgG-treated cells at 8 hours. FIG. 5B depicts the cell lysates from FIG. 5A after 12 h cross-linking were blotted with the indicated Ab. FIG. 5C presents Bcl6, OPN, and actin analyzed from purified CD62L$^-$ CD4$^+$ T cell lysates from B6.ICOS$^{-/-}$ and B6 mice 2 or 3 days post-immunization. FIG. 5D shows Bcl6, OPN, and actin analyzed from sorted CD25$^-$CD44$^{hi}$GITR$^-$CD4$^+$ effector T cell and CD25$^+$CD44$^{hi}$GITR$^+$CD4$^+$ regulatory T cell lysates from B6.ICOS$^{-/-}$ and B6 mice 3 days post-immunization. All results are representative of two independent experiments.

FIG. 6A presents a co-transfection of 293T cells by Flag-p85α and increasing amounts of OPN-i expression plasmids before lysis and immunoprecipitation (IP) as indicated. FIG. 6B depicts enriched CD62L$^-$ CD4$^+$ T cells from OPN KO and WT mice 40 hours post-immunization with KLH in CFA that rested overnight and stimulated as in FIG. 5A for 12 hours followed by IP analysis and protein blotting, as indicated. FIG. 6C shows the flow cytometry of splenocytes from Pi3kr1$^{fl}$ Vav1-Cre$^-$ (p85α WT) and Vav1-Cre$^+$ (p85α KO) mice day 3 post-immunization with KLH in CFA. Numbers adjacent to outlined areas indicate percent Foxp3$^-$Bcl6$^+$CXCR5$^+$ $T_{FH}$ cells and Foxp3$^+$Bcl6$^+$CXCR5$^+$ $T_{FR}$ cells. FIG. 6D is histogram overlays of Bcl6 expression in Foxp3$^-$ICOS$^+$CXCR5$^+$ $T_{FH}$ (top) and Foxp3$^+$ICOS$^+$CXCR5$^+$ $T_{FR}$ (bottom) cells. On the right, Bcl6 MFI is plotted. n=4 per group. FIG. 6E shows p85α KO CD4$^+$ T cells that were transduced with GFP$^+$ retrovirus expressing constitutively-active Akt (cAkt) or control virus (pBABE-GFP) and sorted GFP$^+$ CD4$^+$ T cells were transferred into Rag2$^{-/-}$Prf1$^{-/-}$ hosts followed by immunization with KLH in CFA. p85α WT CD4$^+$ T cells transduced with control virus (Ctrl) were also included. The transduction efficiency (GFP) and the activation status of Akt (phospho-Akt, pAkt) post-reconstitution into p85α KO CD4$^+$ T cells was confirmed. FIG. 6F consists of representative FACS plots of CXCR5$^+$Bcl6$^+$CD4$^+$ T cells at day 5 post-infection. On the right, frequency of CXCR5$^+$Bcl6$^+$CD4$^+$ T cells is plotted. n=4 per group. FIG. 6G illustrates the IP of 293T cell lysates after co-transfection with Flag-p85α and OPN-i WT or Y166F mutant expression plasmids. Aliquots of cell lysates were used as input for assessment of transfected protein expression. Data are representative of three (FIG. 6A-6D, 6G) and two (FIG. 6E-6F) independent experiments.

FIG. 7A shows an immunofluorescence analysis of OPN and Bcl6 expression by enriched CD62L⁻ CD4⁺ T cells from OPN-i KI mice treated with anti-ICOS Ab, as in FIG. 5B. Cells were counterstained with the DNA-intercalating dye DAPI to trace nuclear perimeter. On the right, fluorescence intensity was expressed as the mean ratio of summed nuclear to cytoplasmic fluorescence pixel intensity (n=25-30 cells per value). Original magnification, 600×. FIG. 7B presents the nuclear protein expression in OPN-i KI CD62L⁻CD4⁺ T cells treated with anti-CD3 and/or anti-ICOS Abs, as in FIG. 5B. LaminB1 and tubulin expression were used for validation of the integrity of nuclear separation. FIG. 7C shows a cellular fractionation analysis of protein expression by 293T cells cotransfected with OPN-i or OPN-i Y166F mutant and increasing concentrations of Flag-p85α expression plasmid. FIG. 7D presents an immunofluorescence analysis of OPN and Bcl6 expression by enriched CD62L⁻CD4⁺ T cells from p85α WT or KO mice. Cell treatment and analysis are as in FIG. 7A. Original magnification, 600×. *, P<0.05, ***, P<0.001, Mann-Whitney test (FIG. 7A-7D). All results are representative of at least three independent experiments.

FIG. 8A depicts the protein blot after enriched CD62L⁻ CD4⁺ T cells from OPN KO and KI mice 3 d post-immunization with KLH in CFA were lysed for endogenous co-IP, as indicated. FIG. 8B illustrates Bcl6 protein domain deletion mutants. Bottom, Co-IP of cell lysates of 293T cells co-transfected with OPN-i and Flag-Bcl6 deletion mutant expression plasmids. The Bcl6 ZF deletion mutant has no Flag tag and was co-transfected with Flag-OPN-i plasmid, immunoprecipitated with Flag Ab and blotted with Bcl6 and Flag (OPN-i) Abs. Arrowhead: IgG heavy chain. CDS: complete coding sequence. FIG. 8C shows enriched CD62L⁻ CD4⁺ T cells from OPN KO and KI mice 40 h post-immunization with KLH in CFA that were rested for 2 hours, treated with or without MG132 at 90 minutes after initial priming with anti-CD3 and anti-ICOS, followed by the addition of cycloheximide (CHX) 30 min later and analysis of protein expression at 0 hours and 3 hours after the addition of CHX. Bottom, quantitation of relative Bcl6 protein levels. FIG. 8D presents the degradation rates of Flag-Bcl6 in 293T cells that were transfected with or without OPN-i expression plasmid and treated with CHX. The percent remaining Bcl6 protein levels relative to that before addition of CHX are plotted. FIG. 8E-8G show that 293T cells were transfected with the indicated plasmids and treated with MG132 (FIG. 8E-8F) or DUBi (FIG. 8G) as indicated. Whole cell extracts were denatured, immunoprecipitated with anti-Bcl6 Ab (FIG. 8E) or HA (FIG. 8F) and blotted as indicated. The bracket on the right side of the top panel marks a ladder of bands >85 kDa that corresponds to ubiquitinated Bcl6 (Ubn). An increasing amount of OPN-i plasmids were transfected in (FIG. 8F). Data are representative of three (FIG. 8A, 8C) and two (FIG. 8B, 8D-8G) independent experiments.

FIG. 9A shows OPN KO CD4⁺ T cells infected with GFP⁺ retrovirus expressing WT or Y166F mutant OPN-i or control virus before sorting of GFP⁺ CD4⁺ T cells and transfer into Rag2⁻/⁻Prf1⁻/⁻ hosts followed by LCMV infection. FACS analysis of Foxp3⁻CXCR5⁺Bcl6⁺ $T_{FH}$ cells at day 5 post-infection is shown. FIG. 9B represents the Bcl6 protein expression (MFI) in FIG. 9A. Control virus-infected OPN-i KI CD4⁺ T cells (white bar). Group (WT) versus group (Ctrl) or group (Y166F) difference: *P<0.05. n=5 per group. FIG. 9C depicts purified CD62L⁻ CD4⁺ T cells from B6 mice immunized with type II collagen (CII) and CFA that were infected with indicated GFP⁺ retrovirus and sorted GFP⁺ CD4⁺ T cells (1×10⁵) and then transferred into Rag2⁻/⁻ Prf1⁻/⁻ mice along with B cells (2×10⁶) followed by immunization with CII and CFA at d0 and boosting with CII in IFA at d21. Representative FACS plots (top) and the percentages of Bcl6⁺ CD44⁺ CD4⁺ T cells and GL7⁺ GC B cells, serum titers of anti-mouse CII Ab (bottom) at d28 are shown. Control virus-infected OPN KO CD4⁺ T cells (gray bar). n=4 per group. FIG. 8D shows purified CD25⁺ CD4⁺ T cells from OPN KO mice infected with indicated GFP⁺ retrovirus and sorted GFP⁺ CD4⁺ T cells (4×10⁴) and transferred into Rag2⁻/⁻Prf1⁻/⁻ mice along with 1×10⁵ CD25⁻CD4⁺ T cells and 2×10⁶ B cells (CD45.1⁺) followed by immunization with NP-KLH in CFA at day 0 and boosting with NP-KLH in IFA at day 10. Representative FACS plots of CD45.1⁻Foxp3⁺Bcl6⁺CXCR5⁺CD4⁺ $T_{FR}$ cells and CD45.1⁺Fas⁺ GL7⁺ GC B cells at day 16 post-immunization are shown. FIG. 8E presents the serum titers of anti-NP (top) and anti-ANA Ab (bottom) at day 16 in FIG. 8D. n=3 per group. Control virus-infected OPN-i KI CD25⁺CD4⁺ T cells (white bar). (−): Groups without transfer of CD25⁺ CD4⁺ T cells (gray bar). Data are representative of three (FIG. 9A, 9B) and two (FIG. 9C-9E) independent experiments.

FIG. 11A shows the Spp1 genomic locus and targeting strategy. Boxes represent exons; exon 2 (gray) indicates the mutation site with a deletion of the initial 45 nucleotides that encodes an N-terminal signal sequence while sparing the translational start site and other endogenous elements. A transcriptional STOP element flanked by loxP sites (black triangles) was inserted upstream of this mutation site to prevent OPN-i expression. Germline transmitted OPN-i$^{flstop/+}$ mice were backcrossed to B6 mice for at least 5 generations before crossing with mice carrying the Cre recombinase from the adenovirus EIIa promoter (which targets Cre expression to the early mouse embryo) to generate homozygous mice that constitutively express OPN-i. neo$^r$, neomycin-resistance gene. FIG. 11B is a PCR of genomic DNA showing OPN⁺/⁺ (WT), OPN-i$^{flstop}$ Cre⁺ (KI) and OPN-i$^{flstop}$ Cre⁻ (KO) mice after crossing with EIIa-Cre mice using genotyping primers indicated as gray triangles in FIG. 11A. KO mice gained the STOP element (194 bp) compared to WT allele. WT: 324 bp, KI (after Cre recombination): 453 bp, KO: 518 bp. FIG. 11C shows secreted OPN protein measured by ELISA from purified DC, NK and T cell supernatants from each mouse strain after stimulation with indicated reagents. FIG. 11D depicts the analysis of OPN and actin expression from splenocyte lysates from the indicated mouse strain. Ratios of OPN to actin are shown at the bottom. Right, quantitation of relative OPN protein levels in the indicated mouse strains (n=5 per group). FIG. 11E shows secreted IFNα protein in pDC after stimulation by CpG-B (ODN-1668).

12A shows OT-II×WT, OPN KO and OPN-i KI mice that were immunized as in FIG. 2B. CD44 MFI, percentages of CD4+ T cells and Foxp3+CD44+CD4+ Treg cells were quantified at day 7. n=5 per group. FIG. 12B presents the adoptive transfer and immunization as in FIG. 3A. Serum titers of NP-specific IgG and IgG1 were analyzed at day 7. n=4 per group. FIG. 12C illustrates that OPN-i-deficiency does not affect B cell activity. Naïve OT-II CD4 cells from OPN+/− or OPN−/− mice along with OPN or OPN−/− B cells transferred into Rag2−/−Prf1−/− hosts followed by immunization with NP-OVA in CFA. Serum titers were analyzed at d10. n=4 per group. FIG. 12D shows the Bcl6, OPN, and actin expression by enriched CD62L− CD4+ T cells from each mouse strain at the indicated time points after immunization with KLH in CFA. Quantitation of relative Bcl6 protein levels is plotted at the bottom. FIG. 12E is a kinetic analysis of Bcl6 and Prdm1 mRNA levels in CD62L− CD4+ T cells purified from OPN-i KI or OPN KO mice after immunization with KLH in CFA. FIG. 12F shows that an OPN-i-deficiency affected Bcl6 but not other $T_H$-lineage transcription factors (TF) at d3 after infection with LCMV Armstrong. Percent of cells expressing indicated TF in $T_{FH}$ (CD44+CD25$^{med}$ICOS+CXCR5+CD4) and non-$T_{FH}$ (CD44+CD25$^{hi}$CXCR5−CD4) subsets are depicted. n=4 per group.

FIGS. 13A-13C show a microarray analysis. FIG. 13A is a multiplot of genes upregulated in CD4+ T cells post-activation by anti-CD3 and anti-ICOS compared to anti-CD3 alone as described in FIG. 5A. 210 (red) genes are upregulated and 9 (blue) genes downregulated after co-ligation of CD3 and ICOS (cut-off 1.5 fold and ** P<0.01). FIG. 13B shows a functional analysis performed by Ingenuity pathway analysis (IPA) of 210 genes upregulated by ICOS co-stimulation in FIG. 13A. The Spp1-associated functional annotations that are related to T cell activation, differentiation, antibody production and antibody-mediated autoimmune disease are shown. The significance of the association of the gene expression pattern with a biological function and numbers of genes are indicated. FIG. 13C is a heatmap analysis displaying the 31 genes upregulated in ICOS-activated CD4+ T cells that are correlated with systemic autoimmune syndrome revealed by IPA in FIG. 13B.

FIGS. 14A-14F show how OPN-i interacts with p85α but not p110 and does not regulate Akt activation nor IL-6 signals. Co-IP of cell lysates of 293T cells co-transfected with OPN-i and HA-p110α (FIG. 14A) or HA-p110δ (FIG. 14B) and increasing concentrations of OPN-i expression plasmid. FIG. 14C shows the enriched CD62L− CD4+ T cells from OPN-i KI or OPN KO mice 40 hours post-immunization with KLH in CFA treated as in FIG. 6B. ELISA analysis of total Akt or phospho-Akt (pAkt) levels from cell lysates after 30 minutes of crosslinking. Ratios of pAkt to Akt are plotted. FIG. 14D shows OPN-i does not regulate IL-6-STAT1/3 signals. OT-II×OPN-i KI or OPN KO mice were immunized with NP-OVA in CFA. Splenocytes after 3 days of immunization were stimulated with or without IL-6 (20 ng ml$^{-1}$) for 15 minutes followed by pSTAT1 and pSTAT3 staining. Overlaid histograms among CD4+CD44+ T cells are shown. FIG. 14E is an immunoblot of p85α-immunoprecipitates from 293T cells transfected with vectors expressing Flag-tagged p85α and OPN-i and treated with calf intestinal phosphatase (CIP), analyzed with anti-Flag and anti-OPN. FIG. 14F shows a short sequence motif of OPN with a tyrosine at position 166 that may interact with p85α SH2 domain.

FIG. 15A illustrates 293T cells co-transfected with p85α, Flag-Bcl6, and GFP-expressing OPN-i WT or Y166F mutant expression plasmids. 24 h after transfection, soluble nuclear proteins in the cells were pre-extracted with 0.5% Triton X-100 prior to immunostaining as indicated. In the merged image, yellow shows colocalization of Bcl6 and OPN-i WT but not Y166F mutant. Both Bcl6 and OPN-i WT proteins displayed an overlapping punctuate staining throughout the nuclei. OPN-i Y166F mutant proteins locate mainly within the cytosol. FIG. 15B depicts the co-IP of nuclear and cytoplasmic lysates of 293T cells cotransfected with Flag-Bcl6 and OPN-i WT or Y166F mutant expression plasmid. Bcl6 interacts with OPN-i WT but not Y166F mutant in the nucleus. FIG. 15C shows the overexpression of the OPN-i Y166F mutant protein reduced the interaction between OPN-i WT and p85α. IP of 293T cell lysates after co-transfection are shown with indicated plasmids as in FIG. 6A. FHOPNi-YF vector contains a tandem HA-Flag tag at the C-terminus of OPN-i Y166F.

DETAILED DESCRIPTION OF THE INVENTION

Figure 1:
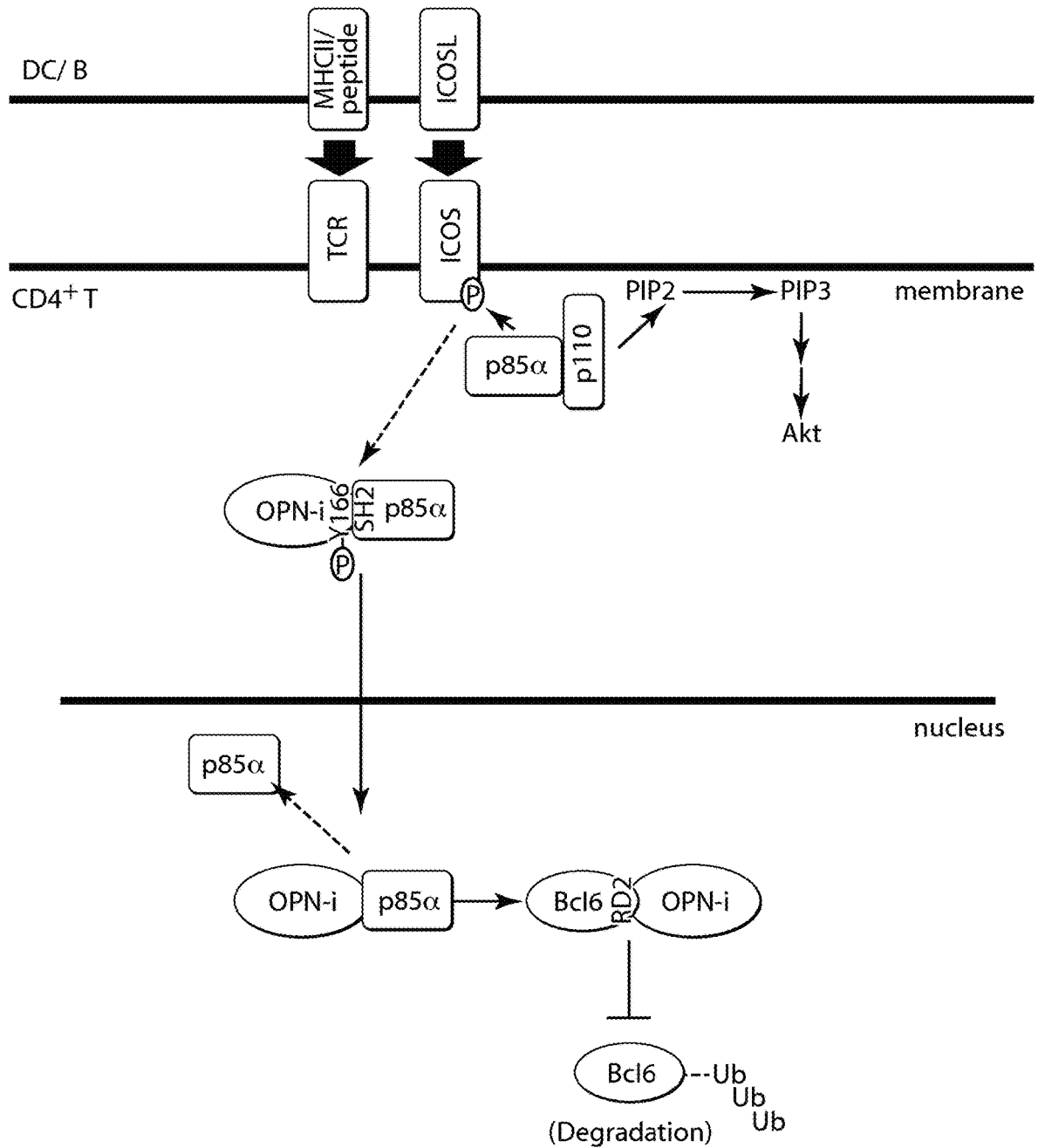
FIG. 1 is a schematic depiction of p85α-OPN-i axis-mediated upregulation of Bcl6-dependent follicular T cell differentiation. Engagement of ICOS and TCR on CD4$^+$ T cells by APC (e.g., DC) promotes p85α-OPN-i complex formation that depends on the tyrosine site 166 of OPN-i. p85α chaperones OPN-i entry into the nucleus, where intranuclear OPN-i interacts with Bcl6 at RD2 region of Bcl6 and protects Bcl6 from ubiquitination-mediated degradation. This p85α-OPN-i axis connects ICOS signals to stable Bcl6 expression (highlighted in blue) and ensures functional follicular T cell differentiation program.

The generation of long-lived high-affinity antibodies after microbial infection or vaccine induction requires precise control of the germinal center (GC) reaction. Follicular helper T ($T_{FH}$) cells are specialized effector CD4+ T cells that provide help for GC formation and induce GC B cells to develop protective antibody responses to invading pathogens. Bcl6, a proto-oncoprotein and a transcriptional repressor belonging to the BTB-POZ family, has been identified as the central transcription factor (TF) that controls $T_{FH}$ differentiation and associated GC responses[1-3]. Since Bcl6 deficiency can result in increased susceptibility to chronic infection, while excessive expression is associated with autoimmunity and lymphocytic transformation, precise control of Bcl6 expression during T-cell differentiation represents an essential component of the $T_{FH}$ cell response[4]. Moreover, recently-defined Foxp3+ follicular regulatory T cells ($T_{FR}$) that inhibit germinal center responses also require Bcl6 expression for their differentiation and suppressive activity[5-7]. However, the mechanisms that govern Bcl6 expression by both $T_{FH}$ and $T_{FR}$ cells were poorly understood. Although engagement of the inducible costimulator (ICOS) receptor by its ligand (ICOSL) represents a key event in a process that culminates in Bcl6 expression and acquisition of the $T_{FH}$ and $T_{FR}$ phenotypes, the essentials of this specialized inductive pathway were previously not well understood.

The present application is based on the discovery of intracellular osteopontin (OPN-i) as a critical molecular bridge that couples ICOS engagement to stable expression of Bcl6 and sustained $T_{FH}$ and $T_{FR}$ responses (FIG. 1) that combine to regulate the germinal center antibody response. Osteopontin (OPN) protein (also known as bone sialoprotein I (BSP-1 or BNSP), early T-lymphocyte activation (ETA-1), secreted phosphoprotein 1 (SPP1), 2ar and Rickettsia resistance (Ric)) is a protein that in humans is encoded by the SPP1 gene (secreted phosphoprotein 1). OPN is expressed as either a secreted (OPN-s) or intracellular (OPN-i) isoform that results from differential usage of OPN translational initiation sites[21]. It was found that ICOS ligation promotes an interaction between the regulatory p85α subunit of phosphatidylinositol-3-OH kinase (PI3K) signaling complex and OPN-i that results in translocation of OPN-i to the nucleus where it interacts with the Bcl6 TF. Binding of intranuclear OPN-i to Bcl6 (via the repression domain 2 [RD2] region)

protects Bcl6 from ubiquitination-mediated proteasome degradation and is essential for sustained Bcl6 protein expression by $T_{FH}$ and $T_{FR}$ cells.

Accordingly, as described in more detail herein, this OPN-i molecular bridge mechanism represents a new avenue for diagnosing and/or prognosing autoimmune disease. Further, the mechanism represents an important new target for identifying activators and inhibitors of the interactions leading to stable Bcl6 protein expression, as such activators and inhibitors can be useful for the treatment of human diseases.

Although elevated plasma levels of the secreted form of OPN (OPN-s) have been used as a surrogate marker for disease activity in certain autoimmune disease, e.g., systemic lupus erythematosus (SLE), psoriasis, inflammatory bowel disease (IBD), Crohn's disease, multiple sclerosis, and asthma (See, e.g., Wong et al., Elevation of plasma osteopontin concentration is correlated with disease activity in patients with systemic lupus erythematosus. *Rheumatology.* 2005; 44 (5): 602-606; Sato et al., Osteopontin/Eta-1 upregulated in Crohn's disease regulates the Th1 immune response. *Gut.* 2005; 54(9):1254-62; Hur et al., Osteopontin-induced relapse and progression of autoimmune brain disease through enhanced survival of activated T cells. *Nature Immunology.* 2006; 8, 74-83; Mishima et al., High plasma osteopontin levels in patients with inflammatory bowel disease. *J Clin Gastroenterol.* 2007; 41(2):167-72; Cehn et al., Elevated plasma osteopontin level is associated with occurrence of psoriasis and is an unfavorable cardiovascular risk factor in patients with psoriasis. *J Am Acad Dermatol.* 2009; 60(2):225-30; Samitas et al., Osteopontin expression and relation to disease severity in human asthma. *Eur. Respir. J.* 2010; 37 (2): 331-41; Rullo et al., Plasma levels of osteopontin identify patients at risk for organ damage in systemic lupus erythematosus. Arthritis Research & Therapy 2013, 15:R18; Iaffaldano et al., The improvement of cognitive functions is associated with a decrease of plasma Osteopontin levels in Natalizumab treated relapsing multiple sclerosis. *Brain Behav Immun.* 2014; 35:96-101), the precise contribution of OPN to disease pathogenesis has not been previously determined. While circulating levels of OPN-s can be detected in the plasma of subjects suffering from autoimmune disease, plasma levels of OPN-s persist for days or weeks after the protein is no longer expressed. Thus, OPN-s is not an accurate representative marker for determining present disease activity or severity, especially in the context of prognosis following treatment. Aspects of the present disclosure relate to the unexpected finding that the intracellular form of OPN (OPN-i), as opposed to secreted form (OPN-s), is responsible for the stabilization of Bcl6 protein expression which regulates the $T_{FH}$ and $T_{FR}$ cell differentiation in normal and abnormal immune responses. Accordingly, methods provided herein of diagnosing and prognosing autoimmune diseases (e.g., involving T cell activation/differentiation such as those described herein) utilizing OPN-i as the biomarker represent a notable improvement over previous methods utilizing plasma OPN-s, as the presence of OPN-i reflects more accurately the current state and/or prognosis of autoimmune disease.

One aspect of the disclosure thus provides a method for diagnosing an autoimmune disease. The method comprises selecting a subject suspected of having an autoimmune disease; measuring expression level of intracellular osteopontin (OPN-i) in a follicular helper T ($T_{FH}$) cells sample obtained from the subject; and identifying the subject as having an autoimmune disease when the expression level of OPN-i is increased as compared to a control level. In some embodiments, methods of diagnosing an autoimmune disease further comprise measuring expression level of inducible T cell costimulator (ICOS) receptor in the follicular helper T ($T_{FH}$) cells sample; and identifying the subject as having an autoimmune disease when the expression levels of both OPN-I and ICOS are increased as compared to a control level for each of OPN-I and ICOS.

Some aspects of the disclosure provide a method for diagnosing an autoimmune disease, the method comprising selecting a subject suspected of having an autoimmune disease; measuring expression level of inducible T cell costimulator (ICOS) receptor in the follicular helper T ($T_{FH}$) cells sample; and identifying the subject as having an autoimmune disease when the expression level of ICOS is increased as compared to a control level. ICOS or CD278 is a CD28-superfamily costimulatory molecule that is expressed on activated T cells. The protein encoded by this gene belongs to the CD28 and CTLA-4 cell-surface receptor family. It forms homodimers and plays an important role in cell-cell signaling, immune responses, and regulation of cell proliferation. Without being bound by theory, it is hypothesized that overexpression of ICOS that is correlated with increased TFH cells and autoimmune phenotype partly reflects an overexpressed OPN-i (or p85α-OPN-i interaction) in $T_{FH}$ cells.

According to some aspects, a method for prognosing an autoimmune disease is provided. The method comprises selecting a subject having or suspected of having an autoimmune disease; measuring expression level of intracellular osteopontin (OPN-i) in a follicular helper T ($T_{FH}$) cells sample obtained from the subject; and identifying the subject as having a less favorable prognosis when the expression level of OPN-i is increased as compared to a control level. In some embodiments, methods of diagnosing an autoimmune disease further comprise measuring expression level of inducible T cell costimulator (ICOS) receptor in the follicular helper T ($T_{FH}$) cells sample; and identifying the subject as having a less favorable prognosis when the expression levels of both OPN-I and ICOS are increased as compared to a control level for each of OPN-I and ICOS.

According to some aspects, a method for prognosing an autoimmune disease is provided, the method comprising selecting a subject having or suspected of having an autoimmune disease; measuring expression level of inducible T cell costimulator (ICOS) receptor in a follicular helper T ($T_{FH}$) cells sample obtained from the subject; and identifying the subject as having a less favorable prognosis when the expression level of OPN-i is increased as compared to a control level.

The term "autoimmune disease" refers to a disease resulting from an immune response against a self-tissue or tissue component, including both autoantibody responses and cell-mediated responses. In some embodiments, autoimmune disease encompasses those diseases or disorders involving excessive or deficient T cell activation (See e.g., King et al., T follicular helper (TFH) cells in normal and dysregulated immune responses. *Annu Rev Immunol.* 2008; 26:741-66; Ma et al., The origins, function, and regulation of T follicular helper cells. *J Exp Med.* 2012; 209(7):1241-53; and Ma and Deenick, Human T follicular helper (Tfh) cells and disease. *Immunol Cell Biol.* 2014; 92(1):64-71) Such diseases include, but are not limited to, systemic lupus erythematosus (SLE), psoriasis, multiple sclerosis, Crohn's disease, inflammatory bowel disease (IBD), asthma, rheumatoid arthritis, psoriatic arthritis, Sjogren's syndrome, Myasthenia, Grave's disease, Hashimoto's thyroiditis, and Juvenile dermatomyositis. One skilled in the art understands that the methods of the invention can be applied to these or other autoimmune diseases, as desired.

Methods involving the prognosis of an autoimmune disease, as described herein, may further involve identifying a less favorable (or conversely a more favorable) prognosis, for example when a subject has increased (or conversely normal or decreased) OPN-i expression as compared to a control or predetermined level.

In the case of SLE, the less favorable prognosis of SLE includes but is not limited to (a) a higher risk of developing central nervous system (CNS) involvement, (b) a higher risk of progressive renal failure and/or (c) a higher risk of cardiovascular diseases, pleurisy and/or abnormalities in the blood. See, e.g., Mok et al., A prospective study of survival and prognostic indicators of systemic lupus erythematosus in a southern Chinese population. *Rheumatology.* 2000; 39 (4): 399-406; and Doria et al., Long-term prognosis and causes of death in systemic lupus erythematosus. *Am J Med.* 2006; 119(8):700-6. In some embodiments, the level of OPN-i expression in a sample obtained from a subject is correlative with one or more SLE prognoses, as described herein.

In some embodiments, the prognosis of psoriasis includes but is not limited to identifying the subject as having an increased likelihood for a mild, moderate or severe disease course, or an increased likelihood of having a prognosis somewhere in between a mild and moderate, or moderate and severe disease course. For example, mild psoriasis has been defined as a percentage of body surface area (BSA) ≤10, a Psoriasis Area Severity Index (PASI) score ≤10, and a dermatology life quality index (DLQI) score ≤10. Moderate to severe psoriasis was defined by the same group as BSA>10 or PASI score >10 and a DLQI score >10. The DLQI is a 10 question tool used to measure the impact of several dermatologic diseases on daily functioning. The DLQI score ranges from 0 (minimal impairment) to 30 (maximal impairment) and is calculated with each answer being assigned 0-3 points with higher scores indicating greater social or occupational impairment. The Psoriasis Area Severity Index is the most widely used measurement tool for psoriasis. PASI assesses the severity of lesions and the area affected and combines these two factors into a single score from 0 (no disease) to 72 (maximal disease). See, e.g., Mrowietz et al., Definition of treatment goals for moderate to severe psoriasis: a European consensus. *Arch Dermatol Res.* 2011; 303 (1): 1-10; and Mease, Measures of psoriatic arthritis: Tender and Swollen Joint Assessment, Psoriasis Area and Severity Index (PASI), Nail Psoriasis Severity Index (NAPSI), Modified Nail Psoriasis Severity Index (mNAPSI), Mander/Newcastle Enthesitis Index (MEI), Leeds Enthesitis Index (LEI), Spondyloarthritis Research Consortium of Canada (SPARCC), Maastricht Ankylosing Spondylitis Enthesis Score (MASES), Leeds Dactylitis Index (LDI), Patient Global for Psoriatic Arthritis, Dermatology Life Quality Index (DLQI), Psoriatic Arthritis Quality of Life (PsAQOL), Functional Assessment of Chronic Illness Therapy-Fatigue (FACIT-F), Psoriatic Arthritis Response Criteria (PsARC), Psoriatic Arthritis Joint Activity Index (PsAJAI), Disease Activity in Psoriatic Arthritis (DAPSA), and Composite Psoriatic Disease Activity Index (CPDAI). *Arthritis Care Res.* 2011; Vol. 63; Supplement 11: S64-S85. In some embodiments, a subject having psoriasis has an increased likelihood of developing psoriatic arthritis. In some embodiments, the level of OPN-i expression in a sample obtained from a subject is correlative with one or more psoriasis prognoses and/or identifies a subject having psoriasis as having an increased risk for psoriatic arthritis, as described herein.

In some embodiments, the prognosis of multiple sclerosis, includes but is not limited to identifying the subject as having an increased likelihood of exhibiting a certain subtype, or pattern of progression of the disease. Several subtypes, or patterns of progression, have been described, including (1) relapsing-remitting; (2) secondary progressive; (3) primary progressive; and (4) progressive relapsing. The relapsing-remitting subtype is characterized by unpredictable relapses followed by periods of months to years of relative quiet (e.g., remission) with no new signs of disease activity. This describes the initial course of about 80% of individuals with MS. The relapsing-remitting subtype typically begins with a clinically isolated syndrome (CIS). In CIS, a subject has an attack indicative of demyelination, but does not fulfill the criteria for multiple sclerosis; 30 to 70% of persons experiencing CIS later develop MS. Secondary progressive MS occurs in about 65% of those subjects with initial relapsing-remitting MS, who eventually have progressive neurologic decline between acute attacks without any definite periods of remission. Occasional relapses and minor remissions may appear. The most common length of time between disease onset and conversion from relapsing-remitting to secondary progressive MS is 19 years. The primary progressive subtype occurs in about 10-20% of individuals, with no remission after the initial symptoms. It is characterized by progression of disability from onset, with no, or only occasional and minor, remissions and improvements. The usual age of onset for the primary progressive subtype is later than of the relapsing-remitting subtype. It is similar to the age that secondary progressive usually begins in relapsing-remitting MS, about 40 years of age. Progressive relapsing MS describes those subjects who, from onset, have a steady neurologic decline but also have clear superimposed attacks. This is the least common of all subtypes. See, e.g., Compston et al., Multiple sclerosis. *Lancet.* 2008; 372 (9648): 1502-17; Lublin et al., Defining the clinical course of multiple sclerosis: results of an international survey. *Neurology.* 1996; 46 (4): 907-11; Tsang et al., Multiple sclerosis—diagnosis, management and prognosis. *Australian family physician.* 2011; 40 (12): 948-55; and Miller et al., Clinically isolated syndromes suggestive of multiple sclerosis, part I: natural history, pathogenesis, diagnosis, and prognosis. *Lancet Neurol.* 2005; 4 (5): 281-8. In some embodiments, the level of OPN-i expression in a sample obtained from a subject is correlative with one or more multiple sclerosis prognoses (e.g., subtypes), as described herein.

In some embodiments, the prognosis of inflammatory bowel disease (IBD), includes but is not limited to identifying the subject as having an increased risk of toxic megacolon, bowel perforation, colorectal cancer, endothelial dysfunction, and coronary artery disease. In some embodiments the IBD is Crohn's disease, and the method may further comprise identifying a subject as having a mild (or benign) to severe course of the disease. Crohn's disease can range from being mild or benign (e.g., when limited Crohn's disease occurs only around the anus in older subjects) or it can be very severe. At the severe end, some patients may experience only one episode and others suffer continuously (e.g., chronic). About 13-20% of patients experience chronic Crohn's disease. Although recurrences are typical, disease-free periods can last for years or decades in some subjects. See, e.g., Roifman et al., Evidence of endothelial dysfunction in patients with inflammatory bowel disease. *Clin.*

*Gastroenterol. Hepatol.* 2009; 7 (2): 175-82; Gandhi et al., Are Patients with Inflammatory Bowel Disease at Increased Risk of Coronary Artery Disease?. *The American Journal of Medicine*. 2012; 125 (10): 956-962; Broome et al., Primary sclerosing cholangitis, inflammatory bowel disease, and colon cancer. *Seminars in Liver Disease*. 2006; 26 (1): 31-41; and Thompson et al., Prognosis and prognostic factors in inflammatory bowel disease. *Saudi J Gastroenterol*. 1995; 1(3):129-37. In some embodiments, the level of OPN-i expression in a sample obtained from a subject is correlative with one or more IBD and/or Crohn's disease prognoses, as described herein.

In some embodiments, the prognosis of asthma, includes but is not limited to identifying the subject as having an increased risk of an intermittent, mild persistent, moderate persistent, or a severe persistent clinical classification. For example, asthma is clinically classified according to the frequency of symptoms, forced expiratory volume in one second ($FEV_1$), and peak expiratory flow rate. Asthma may also be classified as atopic (extrinsic) or non-atopic (intrinsic), based on whether symptoms are precipitated by allergens (atopic) or not (non-atopic). Subjects having an intermittent classification typically have symptom frequency (e.g., wheezing, shortness of breath, chest tightness, and coughing) of ≤2/week; those having mild persistent displaying symptoms >2/week; those having moderate persistent displaying symptoms daily, and those having severe persistent displaying symptoms continuously. See, e.g., Yawn et al., Factors accounting for asthma variability: achieving optimal symptom control for individual patients. *Primary Care Respiratory Journal*. 2008; 17 (3): 138-147; Weinmayr et al., Asthma phenotypes identified by latent class analysis in the ISAAC phase II Spain study. *Clin Exp Allergy*. 2013; 43(2):223-32; and Lang et al., Asthma severity in childhood, untangling clinical phenotypes. *Pediatr Allergy Immunol*. 2010; 21(6):945-53). In some embodiments, the level of OPN-i expression in a sample obtained from a subject is correlative with one or more asthma classifications, as described herein.

In some embodiments, the prognosis of rheumatoid arthritis (RA) includes but is not limited to identifying the subject as having an increased likelihood of having a mild (e.g., prolonged remission), moderate (e.g., intermittent symptoms) or severe disease course (e.g., chronic RA). For example, about 10-20% of subjects having rheumatoid arthritis have sudden onset of the disease, followed by many years with no symptoms; this is considered a prolonged remission. Some subjects having rheumatoid arthritis have symptoms that are intermittent. Periods lasting months when there are few or no symptoms can occur; this is referred to as intermittent symptoms of rheumatoid arthritis. The majority of rheumatoid arthritis patients have the chronic, progressive type of rheumatoid arthritis that requires long-term medical management. Subjects with one or more of the following traits have an increased likelihood of developing a chronic progressive form of RA: flares that are intense and last a long time; diagnosed very young and have had active disease for years; markers for inflammation are elevated on laboratory tests (elevated CRP and ESR); significant joint damage already evident on x-rays when diagnosed; presence of rheumatoid nodules; test positive for rheumatoid factor or anti-CCP. See, e.g., Lindqvist et al., Prognostic laboratory markers of joint damage in rheumatoid arthritis. *Ann Rheum Dis.* 2005; 64:196-201. In some embodiments, the level of OPN-i expression in a sample obtained from a subject is correlative with one or more RA prognoses, as described herein.

The term "subject," as used in any of the methods described herein, refers to an individual organism, for example, an individual mammal. In some embodiments, the subject is a human. In some embodiments, the subject is a non-human mammal. In some embodiments, the subject is a non-human primate. In some embodiments, the subject is a rodent. In some embodiments, the subject is a sheep, a goat, a cattle, a cat, or a dog. In some embodiments, the subject is a research animal. The subject may be of either sex and at any stage of development. As used herein, the term "subject suspected of having an autoimmune disease" refers to a subject that presents one or more symptoms indicative of an autoimmune disease, and/or is a subject having one or more risk factors for autoimmune disease, which include but are not limited to gender, age, ethnicity, genetic predisposition, environmental exposure, previous incidents of autoimmune disease, and previous infection.

A "sample obtained from a subject" as used in any of the methods described herein refers to a biological sample comprising tissue, cells, or body fluid (e.g. blood or lymph node fluid). Typically, the sample comprises T cells (e.g., $T_{FH}$ and/or $T_{FR}$ cells) and the mRNA and/or protein of the relevant gene(s) (e.g., OPN-i). The biological sample can be obtained from any part of a subject that comprises blood cells. In some embodiments, the biological sample comprises peripheral blood or bone marrow. In some embodiments, the biological sample comprises blood cells that are white blood cells. In some embodiments the sample comprises peripheral mononuclear blood cells (PBMCs). In some embodiments, the biological sample is comprised of CXCR5+ CD4+ T cells isolated from peripheral blood or bone marrow. In some embodiments, the sample comprises $T_{FH}$ and/or $T_{FR}$ cells isolated from peripheral blood or bone marrow. In some embodiments, the sample comprises an isolated population of $T_{FH}$ and/or $T_{FR}$ cells. By an "isolated population" it is meant that the cells are physically separated from an environment in which they normally exist, or in which they originally or previously existed. Isolation may refer to physical separation (e.g., by FACS, centrifugation, or the like) of cells from a from a naturally occurring environment or source (e.g., peripheral blood, bone marrow, etc.) or from a culture. In some embodiments, an isolated population will contain at least 80% T cells (e.g., $T_{FH}$ and/or $T_{FR}$ cells), e.g., at least 85%, 90%, 95%, 98%, 99% and above. In some embodiments, the cells in a sample will be 100% T cells (e.g., $T_{FH}$ and/or $T_{FR}$ cells). In some embodiments, a population of cells that is at least 80% T cells (e.g., $T_{FH}$ and/or $T_{FR}$ cells) can be termed a "purified" population. Isolation of T cells (e.g., $T_{FH}$ and/or $T_{FR}$ cells) can be achieved using methods known in the art, e.g., the methods described herein, including but not limited to FACS and magnetic assisted separation. See e.g., Bamumjohann and Ansel, Identification of T follicular helper (Tfh) cells by flow cytometry. *Protocol Exchange*. 2013; doi:10.1038/protex.2013.060. Additionally, commercially available kits can be used to isolate T cells such as $T_{FH}$ and/or $T_{FR}$ cells (e.g., STEMCELL TECHNOLOGIES™ Kits including EASYSEP™ Human T cell Enrichment Kit, Cat.#19051; EASYSEP™ Human CD4+ T cell Enrichment Kit, Cat.#19052; EASYSEP™ Mouse T cell Enrichment Kit, Cat.#19851; and EASYSEP™ Mouse CD4+ T cell Enrichment Kit, Cat.#19752).

The term "measuring expression level" as used in any of the methods described herein refers to measuring the expression level of a gene or gene product (e.g., OPN-i and/or ICOS), and therefore includes measuring mRNA and/or protein levels in cells, for example cells obtained from a subject. In some embodiments, the mRNA expression levels that are measured are those of the human OPN gene (e.g., genomic NCBI Accession NG_030362.1; mRNA NCBI Accessions NM_000582.2, NM_001040058.1, NM_001040060.1, NM_001251829.1, and/or NM_001251830.1) In some embodiments, the methods comprise measuring mRNA expression levels of the human ICOS gene (e.g., genomic NCBI Accession NG_011586.1; mRNA NCBI Accession NM_012092.3). Methods of measuring mRNA are well known in the art, and include methods based on hybridization analysis of polynucleotides as well as methods based on sequencing of polynucleotides. These methods include, but are not limited to, northern blotting, in situ hybridization, RNase protection assays, reverse transcription polymerase chain reaction (RT-PCR), real-time PCR (QPCR), as well as sequence-based gene expression analysis and gene expression analysis by massively parallel signature sequencing. In some embodiments, the mRNA expression levels are measured by using reverse transcription PCR (RT-PCR). Commonly used reverse transcriptases are avilo myeloblastosis virus reverse transcriptase (AMV-RT) and Moloney murine leukemia virus reverse transcriptase (MLV-RT). The reverse transcription step is typically primed using specific primers, random hexamers, or oligo-dT primers. The RT-PCR reaction reverse transcribes the RNA template into cDNA. In some embodiments, the mRNA expression levels are measured by using reverse transcription PCR (RT-PCR) followed by real-time PCR (Q-PCR). In the Q-PCR reaction, the cDNA produced from the RT-PCR is amplified and simultaneously quantified. The PCR step can use a variety of thermostable DNA-dependent DNA polymerases, such as Taq DNA polymerase. Generally, primer design or determining which sequences to use for making a primer is well known in the art. Computer programs are available to determine if a set of nucleotides in a polynucleotide is optimal for initiating a PCR reaction. Therefore, different primers can be used to initiate a PCR reaction and to detect a specific gene product. As such, the expression products of the presently disclosed subject matter can be detected using different primers and the presently disclosed subject matter is not limited to a specific set of primers.

Methods for measuring protein levels (e.g., of OPN-i and/or ICOS) are well known, and include, but are not limited to, immunohistochemical assays, Western blot analyses, ELISAs, polyacrylamide gels, and protein activity assays. Other methods for measuring protein expression levels are well known in the art and the instant disclosure is not limited to any particular method. In some embodiments, OPN-i refers to human OPN-i corresponding to NCBI Accessions NP_001035147.1, NP_000573.1, NP_001035149.1, NP_001238759.1, and/or NP_001238758.1.

In some embodiments, the expression level of variants or fragments of OPN-i, and/or ICOS are measured. Therefore, a gene or gene product comprising variants of polynucleotides or polypeptides according to the presently disclosed subject matter include, but are not limited to, sequences which are at least 70% identical, e.g., at least 75%, 80%, 85%, 90%, 91%, 92%, 93%, 94%, 95%, 96%, 97%, 98%, or 99% identical to the nucleotide or amino acid sequence of OPN-i, and/or ICOS. In some embodiments, the fragment of OPN-i is SEQ ID NO: 2 (FQVSDEQYPDATDED).

The term "identifying" as used in any of the methods described herein refers to a process of determining whether a subject has a certain disease or disorder, or a subject's likelihood of having, or risk of developing a certain disease or disorder, e.g., as described herein. As used herein, identifying a subject at risk of developing an autoimmune disease and/or T cell lymphoma, includes identifying a subject at risk of progressing to a more severe form of the disease state. Accordingly, the methods provided herein can be used to detect or monitor the appearance and progression of autoimmune disease and/or T cell lymphomas in a subject.

The methods provided herein involve identifying subjects as having a disease or disorder (e.g., an autoimmune disease and/or T cell lymphoma), or as having a less favorable prognosis of a disease or disorder, when the expression level of a gene or gene product (e.g., OPN-i, ICOS) is increased as compared to a control level. As used in any of the methods described herein, a "control level" of expression refers, in some embodiments, to a level of expression (e.g., of OPN-i and/or ICOS) in a cell or cell population from an individual who does not suffer from the reference disease or disorder. A control level can also be determined by analysis of a population of individuals. In some embodiments, the control level of expression is from the same individual for whom a diagnosis and/or prognosis is sought or whose disease or disorder is being monitored, but is obtained at a different time and/or from a different source of cells or tissue. As used herein, an "increased" or "decreased" level of expression (e.g., of OPN-i and/or ICOS) as compared to a control level typically refers to a statistically significant difference between a control level of expression from an individual for whom diagnosis and/or prognosis or other information is sought, e.g., an experimental level. Those of ordinary skill in the art will recognize that many methods are available to determine whether a difference is statistically significant and the particular method used is not limiting to the invention. In some embodiments, an increased or decreased level refers to a 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, 200%, 225%, 250%, 275%, 300%, 350%, 400%, 450%, 500%, 550%, 600%, 700%, 800%, 900%, or a 1000% increase or decrease in expression (e.g., of OPN-i and/or ICOS). In some embodiments, an increased or decreased level refers to a greater than 50% increase or decrease in expression (e.g., of OPN-i and/or ICOS).

According to another aspect of the disclosure, methods for diagnosing and/or prognosing T cell lymphomas are provided. As described herein, Bcl6 is a proto-oncoprotein and a transcriptional repressor that has been identified as the central transcription factor that controls $T_{FH}$ differentiation and associated GC responses, and excessive Bcl6 expression is associated with autoimmunity and lymphocytic transformation[4]. The inventors have identified OPN-i as the critical factor that leads to stabilization of Bcl6 protein expression. Without being bound to any particular mechanism, excessive or increased OPN-i expression is therefore likely to contribute to the excessive Bcl6 expression associated with lymphocytic transformation. Accordingly, methods for diagnosing and/or prognosing T cell lymphomas are provided which involve measuring OPN-i in subjects having or suspected of having a T cell lymphoma.

In one aspect, methods for diagnosing T cell lymphomas are provided. The methods comprise selecting a subject suspected of having T cell lymphomas; measuring expression level of intracellular osteopontin (OPN-i) in a follicular helper T (TFH) cells sample obtained from the subject; and identifying the subject as having T cell lymphomas when the expression level of OPN-i is increased as compared to a control level. In some embodiments, methods of diagnosing T cell lymphomas further comprise measuring expression level of inducible T cell costimulator (ICOS) receptor in the follicular helper T ($T_{FH}$) cells sample; and identifying the subject as having a T cell lymphoma when the expression levels of both OPN-I and ICOS are increased as compared to a control level for each of OPN-I and ICOS.

According to some aspects, methods for diagnosing T cell lymphomas are provided, the methods comprising selecting a subject suspected of having T cell lymphomas; measuring expression level of inducible T cell costimulator (ICOS) receptor in a follicular helper T (TFH) cells sample obtained from the subject; and identifying the subject as having T cell lymphomas when the expression level of ICOS is increased as compared to a control level.

In another aspect, methods for prognosing T cell lymphomas are provided. The methods comprise selecting a subject having or suspected of having T cell lymphomas; measuring expression level of intracellular osteopontin (OPN-i) in a follicular helper T (TFH) cells sample obtained from the subject; and identifying the subject as having a less favorable prognosis when the expression level of OPN-i is increased as compared to a control level. In some embodiments, methods of prognosing T cell lymphomas further comprise measuring expression level of inducible T cell costimulator (ICOS) receptor in the follicular helper T ($T_{FH}$) cells sample; and identifying the subject as having a less favorable prognosis when the expression levels of both OPN-I and ICOS are increased as compared to a control level for each of OPN-I and ICOS.

According to some aspects, methods for prognosing T cell lymphomas are provided, the methods comprising selecting a subject having or suspected of having T cell lymphomas; measuring expression level of inducible T cell costimulator (ICOS) receptor in a follicular helper T (TFH) cells sample obtained from the subject; and identifying the subject as having a less favorable prognosis when the expression level of ICOS is increased as compared to a control level.

As used herein, the term "subject suspected of having a T cell lymphoma" refers to a subject that presents one or more symptoms indicative of a T cell lymphoma, and/or is a subject having one or more risk factors for T cell lymphoma. Symptoms of T cell lymphomas include swelling of lymph nodes (which may or may not be painless), fever, unexplained weight loss, sweating (often at night), chills, lack of energy and itching. Risk factors for developing a T cell lymphoma include gender, age, ethnicity, genetic predisposition, body weight and diet, environmental exposure, radiation exposure, immune system deficiency, autoimmune disease (e.g., rheumatoid arthritis, SLE, and celiac disease), infections that directly transform lymphocytes (e.g., human T-cell leukemia/lymphoma virus (HTLV-1) infection, Epstein-Barr virus (EBV) infection, and human herpes virus 8 (HHV8) infection), infections that weaken the immune system (e.g., human immunodeficiency virus (HIV) infection), and infections that cause chronic immune stimulation (e.g., *Helicobacter pylori* infection, *Chlamydophila psittaci* infection, *Campylobacter jejuni* infection, and hepatitis C virus (HCV) infection).

In some embodiments, the methods are used to diagnose and/or prognose any T cell lymphoma, including angiocentric lymphoma, cutaneous T cell lymphoma (CTCL), anaplastic large-cell lymphoma (ALCL), and/or angioimmunoblastic T-cell lymphoma (AITL). The methods are also used for diagnosing and/or prognosing various subtypes of CTCL, including mycosis fungoides, pagetoid reticulosis, Sézary syndrome, granulomatous slack skin, lymphomatoid papulosis, pityriasis lichenoides chronica, pityriasis lichenoides et varioliformis acuta, CD30+ cutaneous T-cell lymphoma, secondary cutaneous CD30+ large cell lymphoma, non-mycosis fungoides CD30-cutaneous large T-cell lymphoma, pleomorphic T-cell lymphoma, Lennert lymphoma, subcutaneous T-cell lymphoma, angiocentric lymphoma, and blastic NK-cell lymphoma (See Willemze et al., WHO-EORTC classification for cutaneous lymphomas. *Blood.* 2005; 105 (10): 3768-85). In some embodiments, the methods are used for diagnosing and/or prognosing various subtypes of ALCL, including systemic ALCL, extranodal ALCL, and cutaneous ALCL (See Medeiros et al., Anaplastic Large Cell Lymphoma. *Am J Clin Pathol.* 2007; 127(5): 707-22).

In some embodiments concerning the prognosis of T cell lymphomas, increased levels of OPN-i and/or ICOS expression may correlate with an increased risk of progressing through one or more clinical stages of the disease. T cell lymphomas can be staged according to the Ann Arbor staging system, which is used to stage both Hodgkin's and non-Hodgkin lymphomas (See Carbone et al., Report of the Committee on Hodgkin's Disease Staging Classification. *Cancer Res.* 1971; 31 (11): 1860-1; and Lister et al., Report of a committee convened to discuss the evaluation and staging of patients with Hodgkin's disease: Cotswolds meeting. *J. Clin. Oncol.* 1989; 7 (11): 1630-6). Stage I indicates that the T cell lymphoma is located in a single region, typically one lymph node and the surrounding area. Stage II indicates that the T cell lymphoma is located in two separate regions, an affected lymph node or organ and a second affected area, and both affected areas are confined to one side of the diaphragm (e.g., both are above the diaphragm, or both are below the diaphragm). Stage III indicates that the T cell lymphoma has spread to both sides of the diaphragm, including one organ or area near the lymph nodes or the spleen. Stage IV indicates diffuse or disseminated involvement of one or more extralymphatic organs, including any involvement of the liver, bone marrow, or nodular involvement of the lungs. Accordingly, in some embodiments an increased expression level of OPN-i and/or ICOS expression (e.g., as compared to a control level) identifies a subject as having an increased risk or progressing from any clinical stage to another (e.g., from I to II, III, or IV; from II to III or IV; or from III to IV). Conversely, in some embodiments, a decreased level of OPN-i and/or ICOS expression can identify a subject as having a decreased risk or progressing from any clinical stage to another. Methods for evaluating the stage of T cell lymphoma are well known, and include, but are not limited to, X-ray computed tomography (x-ray CT), positron emission tomography (PET), and bone marrow biopsy.

According to another aspect of the disclosure, methods for identifying inhibitors of Bcl6 are provided. As described herein, some autoimmune diseases and T cell lymphomas are characterized by excessive Bcl6 expression and/or activity. Accordingly, inhibitors of Bcl6 are useful in the treatment of such autoimmune diseases and T cell lymphomas. Thus, use of the methods described herein can allow for the identification of compounds useful for treating such diseases by screening for compounds having a desired activity, for example from a library of thousands of compounds.

As used herein, a "Bcl6 inhibitor" is a compound or agent (e.g., a small molecule) capable of inhibiting the expression, stabilization, and/or the activity of Bcl6. In some embodiments, because OPN-i was found to be responsible for stabilizing Bcl6 protein expression by preventing the ubiquitin-mediated degradation of Bcl6, a Bcl6 inhibitor includes compounds and agents capable of inhibiting the OPN-i-mediated stabilization of Bcl6. In some embodiments, such methods involve identifying compounds that inhibit the p-85α-mediated translocation of OPN-i to the nucleus of a cell, and/or identifying compounds that inhibit the interaction between OPN-i and Bcl6.

Accordingly, in one embodiment a method for identifying Bcl6 inhibitors comprises (a) combining regulatory p-85α subunit of phosphatidylinositol-3-OH kinase or a fragment thereof with OPN-i or fragment thereof in presence or absence of a test compound; (b) labelling p-85α or fragment thereof with a fluorescence donor and labelling OPN-i or fragment thereof with a fluorescent acceptor, wherein binding of OPN-i to p-85α is detected by proximity-based luminescence detection; and (c) identifying the test compound as a Bcl6 inhibitor when the proximity-based luminescence detection signal is decreased in the presence of the test compound relative to the signal in the absence of the test compound. In some embodiments, the p-85α or fragment thereof and the OPN-i or fragment thereof are labelled with the fluorescence donor and acceptor before combining them in the presence or absence of the test compound.

In some embodiments (e.g., concerning any of the methods described herein for identifying inhibitors, activators, and/or modulators of Bcl6) a "fragment" of p-85α refers to a fragment capable of interacting with OPN-i, e.g., as determined by a binding assay. In some embodiments, a fragment of p-85α refers to a polypeptide comprising the SH2 domain of p-85α. In some embodiments, a fragment of p-85α comprises amino acid residues 333-428 or amino acid residues 624-718 of SEQ ID NO:1. In some embodiments, a fragment of p-85α comprises amino acid residues 333-428 or amino acid residues 624-718 of SEQ ID NO:7. In some embodiments, a fragment of p-85α comprises a sequence that is at least 80%, at least 85%, at least 90%, at least 95%, at least 98%, or at least 99% identical to amino acid residues 333-428 or amino acid residues 624-718 of SEQ ID NO:1 or SEQ ID NO: 7. Similarly, in some embodiments (e.g., concerning any of the methods described herein for identifying inhibitors, activators, and/or modulators of Bcl6), a "fragment" of OPN-i refers to a fragment capable of interacting with p-85α and/or Bcl6, e.g., as determined by a binding assay. In some embodiments, a fragment of OPN-i comprises amino acid residues 159-173 of SEQ ID NO:3 (e.g., the amino acid sequence of SEQ ID NO:2: FQVSDEQYPDATDED), wherein the polypeptide comprises residue Y166 of OPN-i and is optionally phosphorylated at the residue corresponding to Y166. In some embodiments, a fragment of OPN-i comprises amino acid residues 160-174 of SEQ ID NO: 5 (e.g., the amino acid sequence of SEQ ID NO: 6: FRRPDIQYPDATDED), wherein the polypeptide comprises residue Y167 of OPN-i. In some embodiments, a fragment of OPN-i comprises a sequence that is at least 80%, at least 85%, at least 90%, at least 95%, at least 98%, or at least 99% identical to SEQ ID NO:2 or SEQ ID NO: 6.

p85α (amino acid; mouse; UniProt P26450) (SEQ ID NO: 1):

```
                                              (SEQ ID NO: 1)
MSAEGYQYRALYDYKKEREEDIDLHLGDILTVNKGSLVALGFSDGQEARP

EDIGWLNGYNETTGERGDFPGTYVEYIGRKRISPPTPKPRPPRPLPVAPG

SSKTEADTEQQALPLPDLAEQFAPPDVAPPLLIKLLEAIEKKGLECSTLY

RTQSSSNPAELRQLLDCDAASVDLEMIDVHVLADAFKRYLADLPNPVIPV

AVYNEMMSLAQELQSPEDCIQLLKKLIRLPNIPHQCWLTLQYLLKHFFKL

SQASSKNLLNARVLSEIFSPVLFRFPAASSDNTEHLIKAIEILISTEWNE

RQPAPALPPKPPPKPTTVANNSMNNNMSLQDAEWYWGDISREEVNEKLRDT

ADGTFLVRDASTKMHGDYTLTLRKGGNNKLIKIFHRDGKYGFSDPLTFNS

VVELINHYRNESLAQYNPKLDVKLLYPVSKYQQDQVVKEDNIEAVGKKLH

EYNTQFQEKSREYDRLYEEYTRTSQEIQMKRTAIEAFNETIKIFEEQCQT

QERYSKEYIEKFKREGNEKEIQRIMHNHDKLKSRISEIIDSRRRLEEDLK

KQAAEYREIDKRMNSIKPDLIQLRKTRDQYLMWLTQKGVRQKKLNEWLGN

ENTEDQYSLVEDDEDLPHHDEKTWNVGSSNRNKAENLLRGKRDGTFLVRE

SSKQGCYACSVVVDGEVKHCVINKTATGYGFAEPYNLYSSLKELVLHYQH

TSLVQHNDSLNVTLAYPVYAQQRR
``` p85α (amino acid; human; UniProt P27986) (SEQ ID NO: 7):

```
MSAEGYQYRALYDYKKEREEDIDLHLGDILTVNKGSLVALGFSDGQEARP

EEIGWLNGYNETTGERGDFPGTYVEYIGRKKISPPTPKPRPPRPLPVAPG

SSKTEADVEQQALTLPDLAEQFAPPDIAPPLLIKLVEAIEKKGLECSTLY

RTQSSSNLAELRQLLDCDTPSVDLEMIDVHVLADAFKRYLLDLPNPVIPA

AVYSEMISLAPEVQSSEEYIQLLKKLIRSPSIPHQYWLTLQYLLKHFFKL

SQTSSKNLLNARVLSEIFSPMLFRFSAASSDNTENLIKVIEILISTEWNE

RQPAPALPPKPPPKPTTVANNGMNNNMSLQDAEWYWGDISREEVNEKLRDT

ADGTFLVRDASTKMHGDYTLTLRKGGNNKLIKIFHRDGKYGFSDPLTFSS

VVELINHYRNESLAQYNPKLDVKLLYPVSKYQQDQVVKEDNIEAVGKKLH

EYNTQFQEKSREYDRLYEEYTRTSQEIQMKRTAIEAFNETIKIFEEQCQT

QERYSKEYIEKFKREGNEKEIQRIMHNYDKLKSRISEIIDSRRRLEEDLK

KQAAEYREIDKRMNSIKPDLIQLRKTRDQYLMWLTQKGVRQKKLNEWLGN

ENTEDQYSLVEDDEDLPHHDEKTWNVGSSNRNKAENLLRGKRDGTFLVRE

SSKQGCYACSVVVDGEVKHCVINKTATGYGFAEPYNLYSSLKELVLHYQH

TSLVQHNDSLNVTLAYPVYAQQRR
```

OPN-i (amino acid; mouse; UniProt P10923) (SEQ ID NO: 3):

```
MRLAVICFCLFGIASSLPVKVTDSGSSEEKLYSLHPDPIATWLVPDPSQK

QNLLAPQNAVSSEEKDDFKQETLPSNSNESHDHMDDDDDDDDDGDHAES

EDSVDSDESDESHHSDESDETVTASTQADTFTPIVPTVDVPNGRGDSLAY

GLRSKSRSFQVSDEQYPDATDEDLTSHMKSGESKESLDVIPVAQLLSMPS

DQDNNGKGSHESSQLDEPSLETHRLEHSKESQESADQSDVIDSQASSKAS

LEHQSHKFHSHKDKLVLDPKSKEDDRYLKFRISHELESSSSEVN
```

OPN-i (amino acid; human; GenBank: AAC28619.1) (SEQ ID NO: 5):

```
MRIAVICFCLLGITCAIPVKQADSGSSEEKQLYNKYPDAVATWLNPDPSQ

KQNLLAPQTLPSKSNESHDHMDDMDDEDDDDHVDSQDSIDSNDSDDVDDT

DDSHQSDESHHSDESDELVTDFPTDLPATEVFTPVVPTVDTYDGRGDSVV

YGLRSKSKKFRRPDIQYPDATDEDITSHMESEELNGAYKAIPVAQDLNAP

SDWDSRGKDSYETSQLDDQSAETHSHKQSRLYKRKANDESNEHSDVIDSQ

ELSKVSREFHSHEFHSHEDMLVVDPKSKEEDKHLKFRISHELDSASSEVN
```

In some embodiments (e.g., concerning any of the methods described herein for identifying inhibitors, activators, and/or modulators of Bcl6), p-85α (or a fragment thereof) is labeled with a fluorescence acceptor and OPN-i (or a fragment thereof) is labeled with a fluorescence donor. Methods for labeling proteins with fluorescence donors and/or acceptors are well known, and the methods are not limited to a specific type of labeling reaction (See, e.g., Modesti, Fluorescent labeling of proteins. *Methods Mol Biol.* 2011; 783: 101-20). In some embodiments, either or both of the proteins in any of the methods described herein (e.g., p-85α or a fragment thereof; OPN-I or a fragment thereof; polypeptides comprising a Bcl6 RD2 domain; Bcl6 fusion proteins, etc.) are labeled using glutathione-S-transferase (GST) fusions and/or streptavidin/biotin interactions. For example, in some embodiments, either protein (or fragments thereof) are fused to GST, and the proteins are labeled with a florescence donor or acceptor using anti-GST antibodies that comprise a florescence donor or acceptor or using fluorescent glutathione analogs which bind to GST (See, e.g., Huff et al., A fluorescent glutathione analog for monitoring interactions of GST fusion proteins. *The FASEB Journal.* 2012; 26:613.6). In some embodiments, either protein (or fragments thereof) are linked (e.g., conjugated) to biotin, and the proteins are labeled with a florescence donor or acceptor using streptavidin analogs that comprise a florescence donor or acceptor (See, e.g., Diamandis and Christopoulos, The biotin-(strept) avidin system: principles and applications in biotechnology. *Clinical Chemistry.* 1991; vol. 37; no. 5; 625-636; Hirsch et al., Easily reversible desthiobiotin binding to streptavidin, avidin, and other biotin-binding proteins: uses for protein labeling, detection, and isolation. *Anal Biochem.* 2002; 308(2):343-57; and McMahon, Avidin-Biotin Interactions: Methods and Applications. Springer Science & Business Media, 2008).

The methods described herein for identifying inhibitors or activators of Bcl6 involve the use of proximity-based luminescence detection assays to determine whether a test compound inhibits the binding of p-85α with OPN-i. For example, in the absence of a test compound, the two proteins (or fragments thereof) would exhibit maximum binding to one another, and in some embodiments this level of binding (e.g., as determined by the luminescence resulting from the interaction between the fluorescence donor and acceptor molecules which are in close proximity to one another) is used to compare the luminescence that is detected in the presence of a test compound. If a test compound inhibits the interaction (e.g., binding) between the proteins (or fragments thereof), a decrease in luminescence (including no detection of luminescence) is observed, which identifies the compound as an inhibitor of Bcl6. A "decrease" in luminescence, in some embodiments, means a statistically significant decrease in luminescence. In some embodiments, the decrease refers to a 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or a 100% (e.g., no detection) decrease in luminescence. Methods for proximity-based luminescence detection are well known, and in some embodiments include, but are not limited to, fluorescence resonance energy transfer ("FRET"), luminescence resonance energy transfer ("LRET"), fluorescence cross-correlation spectroscopy ("FCCS"), scintillation proximity ("SPA"), chemiluminescence energy transfer ("CRET"), bioluminescence energy transfer ("BRET"), and excimer formation (See, e.g., Goedhart et al., An introduction to fluorescence imaging techniques geared towards biosensor applications. *Methods Mol Biol.* 2014; 1071:17- 28; Arai and Nagai, Extensive use of FRET in biological imaging. *Microscopy (Oxf).* 2013; 62(4):419-28; Aoki et al., Fluorescence resonance energy transfer imaging of cell signaling from in vitro to in vivo: basis of biosensor construction, live imaging, and image processing. *Dev Growth Differ.* 2013; 55(4):515-22; Deshayes and Divita, Fluorescence technologies for monitoring interactions between biological molecules in vitro. *Prog Mol Biol Transl Sci.* 2013; 113:109-43; and Zeug et al., Quantitative intensity-based FRET approaches—a comparative snapshot. *Biophys J.* 2012; 103(9):1821-7). In some embodiments, the proteins used in the proximity-based luminescence detection assays described herein are linked to a solid substrate, including, but not limited to, a microtiter plate, membrane, or bead. In some embodiments, the proteins are linked to the solid substrate via a biotin/(strep)avidin interaction. Methods for linking proteins to solid substrates are well known in the art (See, e.g., Duk et al., The biotin/avidin-mediated microtiter plate lectin assay with the use of chemically modified glycoprotein ligand. *Anal Biochem.* 1994; 221(2):266-72; McMahon, Avidin-Biotin Interactions: Methods and Applications. Springer Science & Business Media, 2008; and Nahar, Covalent immobilization of proteins onto photoactivated polystyrene microtiter plates for enzyme-linked immunosorbent assay procedures. *Protocol Exchange.* 2013 doi:10.1038/protex.2013.090).

A "test compound" as used in any of the methods described herein refers to an agent comprising or consisting of a compound, molecule, or complex, that is being tested for its ability to inhibit or activate Bcl6, as described herein. Test compounds can be any agent, including, but not restricted to, peptides, peptoids, proteins, lipids, metals, nucleotides, nucleosides, small molecules and combinations and derivatives thereof. Small molecules typically have a molecular weight between 50 and about 2,500 daltons, and in some embodiments in the range 200-800 daltons. Test compounds can be derived or selected from large libraries of synthetic or natural compounds. For example, synthetic compound libraries are commercially available from Maybridge Chemical Co. (Trevillet, Cornwall, UK) or Aldrich (Milwaukee, Wis.). Alternatively, libraries of natural compounds in the form of bacterial, fungal, plant and animal extracts may be used. Additionally, test compounds can be synthetically produced using combinatorial chemistry either as individual compounds or as mixtures.

In some embodiments, methods for identifying Bcl6 inhibitors comprise (a) combining OPN-i or a fragment thereof (e.g., as described herein) with a polypeptide comprising a Bcl6 RD2 domain in presence or absence of a test compound; labelling OPN-i or fragment thereof with a fluorescence donor and labelling Bcl6 RD2 domain with a fluorescent acceptor; detecting binding of OPN-i to Bcl6 RD2 domain by proximity-based luminescence detection; performing an assay to determine whether the test compound binds to OPN-i; and identifying the test compound as a Bcl6 inhibitor when the proximity-based luminescence detection signal is decreased in the presence of the test compound relative to the signal in the absence of the test compound, and the test compound binds to OPN-i. In some embodiments, the OPN-i or fragment thereof and the polypeptide comprising a Bcl6 RD2 domain are labelled are labelled with the fluorescence donor or acceptor before combining them in the presence or absence of the test compound. In some embodiments, the test compound binds to the RD2 domain of Bcl6. In some embodiments, OPN-i is labeled with a fluorescence acceptor, and the Bcl6 RD2 domain is labeled with a fluorescence donor. In some embodiments, the Bcl6 RD2 domain comprises amino acid residues 121-300 of SEQ ID NO:4 or SEQ ID NO: 8. In some embodiments, the Bcl6 RD2 domain comprises an amino acid sequence that is at least 80%, at least 85%, at least 90%, at least 95%, at least 98%, or at least 99% identical to amino acid residues 121-300 of SEQ ID NO:4 or SEQ ID NO: 8.

```
Bcl6 (amino acid; mouse; UniProt P41183) (SEQ ID
NO: 4):
MASPADSCIQFTRHASDVLLNLNRLRSRDILTDVVIVVSREQFRAHKTVL

MACSGLFYSIFTDQLKCNLSVINLDPEISPEGFCILLDFMYTSRLNLREG

NIMAVMTTAMYLQMEHVVDTCRKFIKASEAEMAPALKPPREEFLNSRMLM

PHDIMAYRGREVVENNMPLRNTPGCESRAFAPPLYSGLSTPPASYPMYSH

LPLSTFLFSDEELRDAPRMPVANPFPKERALPCDSARQVPNEYSRPAMEV

SPSLCHSNIYSPKEAVPEEARSDIHYSVPEGPKPAVPSARNAPYFPCDKA

SKEEERPSSEDEIALHFEPPNAPLNRKGLVSPQSPQKSDCQPNSPTESCS

SKNACILQASGSPPAKSPTDPKACNWKKYKFIVLNSLNQNAKPEGSEQAE

LGRLSPRAYPAPPACQPPMEPANLDLQSPTKLSASGEDSTIPQASRLNNL

VNRSLAGSPRSSSESHSPLYMHPPKCTSCGSQSPQHTEMCLHTAGPTFPE

EMGETQSEYSDSSCENGTFFCNECDCRFSEEASLKRHTLQTHSDKPYKCD

RCQASFRYKGNLASHKTVHTGEKPYRCNICGAQFNRPANLKTHTRIHSGE

KPYKCETCGARFVQVAHLRAHVLIHTGEKPYPCEICGTRFRHLQTLKSHL

RIHTGEKPYHCEKCNLHFRHKSQLRLHLRQKHGAITNTKVQYRVSAADLP

PELPKAC

Bcl6 (amino acid; human; UniProt P41182) (SEQ ID
NO: 8):
MASPADSCIQFTRHASDVLLNLNRLRSRDILTDVVIVVSREQFRAHKTVL

MACSGLFYSIFTDQLKCNLSVINLDPEINPEGFCILLDFMYTSRLNLREG

NIMAVMATAMYLQMEHVVDTCRKFIKASEAEMVSAIKPPREEFLNSRMLM

PQDIMAYRGREVVENNLPLRSAPGCESRAFAPSLYSGLSTPPASYSMYSH

LPVSSLLFSDEEFRDVRMPVANPFPKERALPCDSARPVPGEYSRPTLEVS

PNVCHSNIYSPKETIPEEARSDMHYSVAEGLKPAAPSARNAPYFPCDKAS

KEEERPSSEDEIALHFEPPNAPLNRKGLVSPQSPQKSDCQPNSPTESCSS

KNACILQASGSPPAKSPTDPKACNWKKYKFIVLNSLNQNAKPEGPEQAEL

GRLSPRAYTAPPACQPPMEPENLDLQSPTKLSASGEDSTIPQASRLNNIV

NRSMTGSPRSSSESHSPLYMHPPKCTSCGSQSPQHAEMCLHTAGPTFPEE

MGETQSEYSDSSCENGAFFCNECDCRFSEEASLKRHTLQTHSDKPYKCDR

CQASFRYKGNLASHKTVHTGEKPYRCNICGAQFNRPANLKTHTRIHSGEK

PYKCETCGARFVQVAHLRAHVLIHTGEKPYPCEICGTRFRHLQTLKSHLR

IHTGEKPYHCEKCNLHFRHKSQLRLHLRQKHGAITNTKVQYRVSATDLPP

ELPKAC
```

In some embodiments, methods for identifying Bcl6 inhibitors comprise cell-based assays. For example, in some embodiments methods for identifying Bcl6 inhibitors comprise (a) combining cells expressing fluorescently labelled Bcl6 fusion protein and p-85α subunit with OPN-i or fragment thereof in the presence or absence of a test compound; and (b) identifying the test compound as a Bcl6 inhibitor when fluorescence signal is decreased in the presence of the test compound relative to the signal in the absence of the test compound. As described herein, OPN-i translocates to the nuclease with the aid of p-85α, where it stabilizes Bcl6 protein by inhibiting the ubiquitination and subsequent degradation of Bcl6. Accordingly, in the absence of a test compound which inhibits the translocation of OPN-i to the nuclease (e.g., by interfering with the binding between p-85α and OPN-i) and/or inhibits the interaction between OPN-i and Bcl6, the fluorescent Bcl6 protein will not be ubiquitinated and degraded (or will only be minimally ubiquitinated and degraded). The amount of fluorescence measured in this condition is the reference, or control level of fluorescence. Conversely, in the presence of a compound which inhibits one or both of the above activities, fluorescent Bcl6 will be ubiquitinated and subsequently degraded, in turn producing a decreased (including no) level of fluorescence, which identifies the compound as an inhibitor of Bcl6. In some embodiments, the decrease in fluorescence refers to a 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or a 100% (e.g., no detection) decrease in fluorescence.

The cells can be any cells capable of expressing the proteins, and are typically eukaryotic cells including yeast cells. In some embodiments the cells are mammalian cells. In some embodiments, the cells are T cells (e.g., $T_{FH}$ and/or $T_{FR}$ cells). In some embodiments, the cells are immortalized T cells, for example Jurkat cells (e.g., Jurkat Clone E6-1 (ATCC® TIB-152™).

Methods for producing fluorescent fusion proteins are well known, and the disclosure is not limited to a particular method. The fluorescent protein fused to Bcl6 can be any fluorescent protein, including, but not limited to Azurite, EBFP2, mKalama1, mTagBFP2, TagBFP, ECFP, Cerulean, mCerulean3, SCFP3A, CyPet, mTurquoise, mTurquoise2, TagCFP, mTFP1, monomeric Midoriishi-Cyan, Aquamarine, TurboGFP, TagGFP2, mUKG, Superfolder GFP, Emerald, EGFP, Monomeric Azami Green, mWasabi, Clover, mNeonGreen, TagYFP, EYFP, Topaz, Venus, SYFP2, Citrine, Ypet, lanRFP-ΔS83, mPapayal, Monomeric Kusabira-Orange, mOrange, mOrange2, mKOκ, mKO2, TagRFP, TagRFP-T, mRuby, mRuby2, mTangerine, mApple, mStrawberry, FusionRed, mCherry, mNectarine, mKate2, HcRed-Tandem, mPlum, mRaspberry, mNeptune, NirFP, TagRFP657, TagRFP675, mCardinal, iFP1.4, iRFP713 (iRFP), iRFP670, iRFP682, iRFP702, iRFP720, Sapphire, T-Sapphire, mAmetrine, mKeima Red, mBeRFP, LSS-mKate2, LSS-mKate1, and LSSmOrange. In some embodiments, an amino acid linker joins the two segments of the fusion protein. In some embodiments, a non-peptidic linker joins Bcl6 to a fluorescent protein or a fluorophore.

According to another aspect of the disclosure, methods for identifying activators of Bcl6 are provided. As described herein, Bcl6 deficiency has been linked to immunodeficiency and susceptibility to chronic infection. Accordingly, activators of Bcl6 are useful in the treatment of such conditions. Thus, use of the methods described herein can allow for the identification of compounds useful for treating such conditions by screening for compounds having a desired activity, for example from a library of thousands of compounds.

As used herein, a "Bcl6 activator" is a compound or agent (e.g., a small molecule) capable of increasing or enhancing the expression, stabilization, and/or the activity of Bcl6. In some embodiments, because OPN-i was found to be responsible for stabilizing Bcl6 protein expression by preventing the ubiquitin-mediated degradation of Bcl6, a Bcl6 activator includes compounds and agents capable of enhancing or promoting the OPN-i-mediated stabilization of Bcl6.

Accordingly, in one embodiment the methods comprise (a) combining regulatory p-85α subunit of phosphatidylinositol-3-OH kinase or a fragment thereof with OPN-i or fragment thereof in presence or absence of a test compound; (b) labelling p-85α or fragment thereof with a fluorescence donor and labelling OPN-i or fragment thereof with a fluorescent acceptor, wherein binding of OPN-i to p-85α is detected by proximity-based luminescence detection; and (c) identifying the test compound as a Bcl6 activator when the proximity-based luminescence detection signal is increased in the presence of the test compound relative to the signal in the absence of the test compound.

In another embodiment, methods for identifying activators of Bcl6 comprise (a) combining OPN-i or a fragment thereof with Bcl6 RD2 domain in presence or absence of a test compound; (b) labelling OPN-i or fragment thereof with a fluorescence donor and labelling Bcl6 RD2 domain with a fluorescent acceptor, wherein binding of OPN-i to Bcl6 RD2 domain is detected by proximity-based luminescence detection; and (c) identifying the test compound as a Bcl6 inhibitor when the proximity-based luminescence detection signal is increased in the presence of the test compound relative to the signal in the absence of the test compound.

In some embodiments, an "increase" in luminescence means a statistically significant increase in luminescence. In some embodiments, the increase is a 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 100%, 150%, 200%, 250%, 300%, 350%, 400%, 450%, or a 500% or more increase in luminescence. In some embodiments, the increase is a 2-fold, 3-fold, 4-fold, 5-fold, 6-fold, 7-fold, 8-fold, 9-fold, or 10-fold or more increase in luminescence.

According to another aspect, methods for identifying modulators of Bcl6 are provided. As used herein, a "modulator" of Bcl6 is a compound or agent capable of increasing or decreasing Bcl6 protein expression or stabilization. In some embodiments, the methods comprise (a) combining OPN-i or a fragment thereof with Bcl6 RD2 domain in presence or absence of a test compound, wherein binding of OPN-i to Bcl6 RD2 domain is detected by an enzyme-linked immunosorbent assay-(ELISA-) based assay; and (b) identifying the test compound as a Bcl6 modulator when the ELISA signal is decreased or increased in the presence of the test compound relative to the signal in the absence of the test compound. ELISA-based assays for detecting the binding between proteins are well known, and include those described in Lequin, Enzyme immunoassay (EIA)/enzyme-linked immunosorbent assay (ELISA). *Clin. Chem.* 2005; 51 (12): 2415-8; and Sandhu et al., Enzyme-Linked Immuno-Sorbent Assay (ELISA), basics and its application: A comprehensive review. *Journal of Pharmacy Research.* 2011, Vol. 4 Issue 12, p4581. In some embodiments, a "decreased" or "increased" signal means a statistically significant decrease or increase. For example, in some embodiments, the decrease or increase is a 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 100%, 150%, 200%, 250%, 300%, 350%, 400%, 450%, or a 500% or more decrease or increase in signal. In some embodiments, the decrease or increase is a 2-fold, 3-fold, 4-fold, 5-fold, 6-fold, 7-fold, 8-fold, 9-fold, or 10-fold or more decrease or increase in signal.

In some embodiments, any of the compounds identified by the methods provided herein for identifying Bcl6 inhibitors, activators, and modulators, can be further validated using T cell activation assays, which are routine in the art. Such methods include those described in the Examples, as well as those described in Karttunen et al., Detection of rare antigen-presenting cells by the lacZ T-cell activation assay suggests an expression cloning strategy for T-cell antigens. *Proc Natl Acad Sci USA.* 1992; 89(13): 6020-6024; and Sasaki et al., Function of PI3Kγ in Thymocyte Development, T Cell Activation, and Neutrophil Migration. *Science.* 2000; Vol. 287 no. 5455 pp. 1040-1046.

According to another aspect of the disclosure, methods for enhancing adoptive T cell transfer in a subject are provided. Such methods are useful for the treatment of autoimmune disease and/or cancer such as T cell lymphomas, such as those described herein. Methods for adoptive T cell transfer, e.g., for treating autoimmune disease and cancers are well known, and include those described by Tamer et al., Treatment of autoimmune disease by adoptive cellular gene therapy. *Ann N Y Acad Sci.* 2003; 998:512-9; Wieczorek and Uharek, Genetically modified T cells for the treatment of malignant disease. *Transfus Med Hemother.* 2013; 40(6):388-402; Tey et al., Adoptive T-cell transfer in cancer immunotherapy. *Immunology and Cell Biology.* 2006; 84, 281-289; and June, Principles of adoptive T cell cancer therapy. *J Clin Invest.* 2007; 117(5):1204-1212.

In some embodiments, the method comprises isolating CD4+ T cells from peripheral blood from a subject in need thereof; transducing the isolated CD4+ T cells by contacting the CD4+ T cells with retroviral vectors expressing OPN-i; expanding the transduced CD4+ T cells by growing them in a culture medium until the number of transduced CD4+ T cells increases by at least 5%; and administering the expanded transduced CD4+ T cells to the subject. In some embodiments, the method further comprises transducing the isolated CD4+ T cells by contacting the CD4+ T cells with retroviral vectors expressing p85α. In some embodiments, the T cells are expanded by at least 1%, at least 2%, at least 3%, at least 4%, at least 5%, at least 6%, at least 7%, at least 8%, at least 9%, at least 10%, at least 12%, at least 15%, or at least 20% or more.

The term "transducing" as used herein refers to a process by which exogenous nucleic acid is transferred or introduced into the T cell. Methods for transducing cells are well known, and typically involves the use of a vector, including viral vectors (e.g., retroviral vectors). The term "vector" refers to a polynucleotide comprising one or more recombinant polynucleotides encoding a protein described herein (e.g., OPN-i, p-85α, Bcl6, and/or RD2 of Bcl6). Vectors include, but are not limited to, plasmids, viral vectors, cosmids, artificial chromosomes, and phagemids. The vector is able to replicate in a host cell (e.g., T cell) and is further characterized by one or more endonuclease restriction sites at which the vector may be cut and into which a desired nucleic acid sequence may be inserted. Methods for generating vectors capable of expressing a protein, such as OPN-i, are well known, and include those described in Green and Sambrook, Molecular Cloning: A Laboratory Manual (4th ed., Cold Spring Harbor Laboratory Press, Cold Spring Harbor, N.Y. (2012)). In some embodiments, the T cells are activated T cells, e.g., the T cells are activated in vitro or in vivo prior to being administered. Methods for activating T cells are known, and include those described by Hedfors and Brinchman, Long-term proliferation and survival of in vitro-activated T cells is dependent on Interleukin-2 receptor signaling but not on the high-affinity IL-2R. *Scand J Immu-* nol. 2003; 58(5):522-32. In some embodiments, the T cells are modified to express a chimeric antigen receptor (CAR). In general, a CAR and CAR modified T cells are described in PCT/US2011/064191, which is incorporated herein by reference in its entirety. As would be understood by those skilled in the art, CAR modified T cells can be generated by any method known in the art. For example, the CAR modified T cells can be generated by introducing an expression vector encoding the CAR to a T cell, as described herein. In some embodiments, the T cells are modified to express p-85α, e.g., as described herein.

In some embodiments, the method comprises treating the isolated CD4+ T cells with cell-permeable OPN-i or fragments thereof, e.g., as opposed to transducing the cells with a vector expressing OPN-i. By "cell-permeable" OPN-i it is meant that the protein is modified or formulated in such a way as to penetrate the cell membrane without adversely affecting the cell, while delivering active OPN-i to the interior of the cell. Methods for engineering cell-permeable proteins are known, and include those described by Rojas et al., Genetic engineering of proteins with cell membrane permeability. *Nature Biotechnology.* 1998; 16, 370-375; Munst et al., Engineering cell-permeable protein. *Journal of Visualized Experiments.* January 2009; DOI:10.3791/1627; and in U.S. Pat. No. 6,780,843 entitled "Sequence and method for genetic engineering of proteins with cell membrane translocating activity." In some embodiments, the cell-permeable OPN-i or fragments thereof comprise OPN-i or fragments thereof fused to protein transduction domains (PTD) in order to facilitate entry into a T cell (See, e.g., Beerens et al., Protein transduction domains and their utility in gene therapy. *Curr Gene Ther.* 2003; 3(5):486-94; and van den Berg and Dowdy, Protein transduction domain delivery of therapeutic macromolecules. *Curr Opin Biotechnol.* 2011; 22(6):888-93. In some embodiments, the PTD comprises transportan, AntHD, TAT, VP22, or cationic prion protein domains, or functional fragments thereof. In some embodiments, the OPN-i is formulated in a liposome in order to permeate the cells. In some embodiments, the OPN-i is formulated with a carrier in order to permeate the cells.

Methods for administering T cells to a subject are well known, and typically involve intravenous administration, though the methods provided herein are not limited to intravenous administration. In some embodiments, the T cells are administered in an amount effective to provide a therapeutic effect. The term "effective amount" as provided herein, refer to a sufficient amount of the agent (e.g., T cells) to provide an immunological response and corresponding therapeutic effect. The exact amount required will vary from subject to subject, depending on the species, age, and general condition of the subject, the severity of the condition being treated, and the particular agent, mode of administration, and the like. An appropriate "effective" amount in any individual case may be determined by one of ordinary skill in the art using routine experimentation.

The present invention is further illustrated by the following Example, which in no way should be construed as further limiting. The entire contents of all of the references (including literature references, issued patents, published patent applications, and co-pending patent applications) cited throughout this application are hereby expressly incorporated by reference.

Example

Overview

The antagonistic follicular CD4+ T cell pair—helper $T_{FH}$ and regulatory $T_{FR}$ cells—regulates the quantity and quality of humoral immunity. Although both cell types express high levels of the inducible costimulator (ICOS) receptor and require Bcl6 for their functional differentiation, the essentials of the ICOS-dependent pathway that coordinates their opposing responses are not well understood. It is reported that engagement of the ICOS receptor promotes an interaction between the regulatory p85α subunit of PI3K and intracellular osteopontin (OPN-i) that results in nuclear translocation of OPN-i where it interacts with Bcl6 and protects it from ubiquitin-dependent proteasome degradation. Post-translational protection of Bcl6 expression by intranuclear OPN-i is essential for sustained $T_{FH}$ and $T_{FR}$ cell responses and for regulation of the germinal center B cell responses to antigen. Identification of the p85α-OPN-i axis as a molecular bridge that couples ICOS to Bcl6 expression and Bcl6-dependent functional differentiation of $T_{FH}$ and $T_{FR}$ cells provides new molecular insight into the regulation of humoral immunity and suggests new therapeutic avenues to manipulate the $T_{FH}$ and $T_{FR}$ cell response.

Materials and Methods

Mice

C57BL/6J (B6), Pi3kr1$^{fl}$, TCRα$^{-/-}$, OT-II transgenic (Jackson Labs), Rag2$^{-/-}$Prf1$^{-/-}$, CD45.1$^{+}$ C57BL/6 (Taconic Farms), B6. Foxp3GFP mice (kindly provided by Dr. H. von Boehmer), OPN-i$^{+/+}$, OPN-i$^{flstop}$ Cre$^{+}$ and Cre$^{-}$ littermates (FIG. 11) were housed in pathogen-free conditions. Deletion of loxP-flanked Pi3kr1 gene in hematopoietic cells was achieved by crossing Pi3kr1$^{fl}$ mice with Vav1-iCre (Jackson Labs) that express Cre under the Vav1 promoter. All experiments were performed in compliance with federal laws and institutional guidelines as approved by DFCI's Animal Care and Use Committee.

Antibodies and Flow Cytometry

Fluorescence dye labeled Abs specific for CD4 (L3T4), B220 (RA3-6B2), CD44 (IM7), Fas (15A7), IgM (II/41), T- and B-cell activation antigen (GL7), ICOS(C398.4A), PD-1 (J43), CXCR5 (2G8), Bcl6 (K112-91), GATA-3 (L50-823), FoxP3 (FJK-16s), RORγt (B2D), and T-bet (4B10) were purchased from BD, eBioscience and Biolegend. Intracellular staining for Bcl6, FoxP3, RORγt, GATA-3 and T-bet was performed using the FoxP3 staining buffer set (eBioscience). Intracellular staining of phospho-S473-AKT (M89-61), pSTAT1 (14/P-STAT1), pSTAT3 (4/P-STAT3) was conducted according to manufacturer's instruction (BD Bioscience). Cells were acquired on a FACSCantoII using FACSDIva software (BD Biosciences) and analyzed with FlowJo software (Tristar).

Adoptive Transfer

Purified B cells and CD25-depleted CD4+ T cells (>95%) that were separately negatively selected using B cell and CD4 T lymphocyte enrichment set (BD Bioscience) were transferred into Rag2$^{-/-}$Prf1$^{-/-}$ hosts before immunization with NP-OVA in CFA at day 0 and reimmunization with NP-OVA in IFA at the indicated times, as described in legends. Serum was prepared at the indicated time for measurement of primary and secondary responses, respectively.

Enzyme-Linked Immunosorbent Assay (ELISA)

Detection of NP-specific antibodies was performed as described[47]. Analysis of anti-mouse collagen antibody was performed as described[48]. Determination of pAkt and Akt levels was conducted using InstantOne™ ELISA kit (eBioscience).

Plasmids and Generation of Retroviral OPN-i Expression Vectors

OPN-i expression vectors, pMLS5, OPN-i-Flag, and OPN-i-GFP were described previously[21]. The BamHI-XhoI OPN-i cDNA was introduced into pcDNA™6/myc-His vector (Invitrogen) to yield the OPN-i-Myc construct. A tandem HA-Flag tag was introduced at the C-terminus of OPN-i cDNA by PCR using primers containing BamHI and EcoRI sites followed by cloning into pBABE-GFP vector. Bcl6 cDNA was obtained from Open Biosystems (Bcl6 Clone ID: 6309948), sequenced in full, before complete coding region sequences were cloned in frame with a Flag tag at the N-terminus into retroviral expression vector MSCV-IRES-GFP. The following plasmids were obtained from Addgene: p85α (plasmid 1399 and 1407), HA-p110 (plasmid 12522 and 15691)[49, 50] and HA-Ub (plasmid 17608)[51]. Deletion constructs of Bcl6, Flag-Bcl6, and OPN-i Y166F mutants were generated by PCR-mediated mutagenesis with the QuickChange II XL Site-Directed Mutagenesis Kit (Agilent). The accuracy of all plasmids was confirmed by DNA sequencing. Retroviral stocks were generated by transfection of 293T cells with pBABE-GFP control or OPN-i WT or mutant vector along with pCL-Eco packaging vector using TransIT-LT1 transfection reagent (Mirus). Viral supernatants were collected 72 hours later before infection of CD4$^+$ T cells, as described below.

Retroviral Infection.

Purified naive CD4$^+$ T cells from indicated mice strains were stimulated with plate-coated anti-CD3 (5 μg ml$^{-1}$) and anti-CD28 (5 μg ml$^{-1}$) in the presence of 10 ng ml$^{-1}$ human IL-2 (hIL-2). 24-36 hours post-stimulation, CD4$^+$ T blasts were infected with retrovirus expressing GFP and the indicated genes in the presence of 8 μg ml$^{-1}$ of polybrene before 1 h centrifugation at 2000 rpm followed by 6-8 hours at 37° C. and subsequent replacement of three quarters of hIL2-containing fresh medium. After a total of 3 day stimulation, CD4$^+$ T cells were rested in the presence of hIL-2 for 1-2 days before sorting for GFP$^+$ CD4$^+$ T cells and adoptive transfer into Rag2$^{-/-}$Prf1$^{-/-}$ mice followed by immunization as described above. In FIG. 9, 1×10$^5$ sorted GFP$^+$ CII-immune CD4$^+$ T cells and 2×10$^6$ B cells were transferred before immunization with chicken CII in CFA and boosting with CII in IFA, as described previously[48]. Retroviral infection of CD25$^+$CD4$^+$ T cells was adapted from Haxhinasto et al[28]. Briefly, purified CD25$^+$CD4$^+$ T cells were stimulated with plate-coated anti-CD3 (5 μg ml$^{-1}$) and anti-CD28 (5 μg ml$^{-1}$) in the presence of 1,000 U ml$^{-1}$ human IL-2 (hIL-2) and 20 ng ml$^{-1}$ TGFβ. Three days post-stimulation, cells were infected with retrovirus expressing GFP and the indicated genes, as described above, for a total of 2 days before sorting GFP$^+$ cells and transfer.

Immunoprecipitation and Immunoblot

The procedure was performed as described previously[20]. The following antibodies were used: p85α and Bcl6 (Santa Cruz); Flag, actin (Sigma), OPN (IBL American), Myc, tubulin, lamin B1 (Invitrogen) and HA (Cellsignal). Band intensity was quantified using ImageJ software, version 1.45b (NIH).

Immunofluorescence Staining

CD62L$^-$ CD4$^+$ T cells (>95%) from the indicated mouse strains 40 h post-immunization with KLH in CFA using MACS CD4$^+$ CD62L$^+$ T cell isolation kit (Miltenyi) were stimulated with anti-ICOS for the indicated times before fixation, permeabilization and immunostaining. Antibodies or dyes used include: rabbit Bcl6 (N-3), anti-rabbit Alexa Fluor 568 (for Bcl6); mouse OPN (AKm2A1), anti-mouse Alexa Fluor 647 (for OPN) and nuclear dye DAPI. Images were captured through a 63× objective lens with a Leica SPSX laser scanning confocal microscope and analyzed using ImageJ software, version 1.45b (NIH).

Gene Expression Profiling

Naïve CD4$^+$ T cells (>95%) were purified from single cell suspensions of B6 spleen using the MACS CD4$^+$ CD62L$^+$ T cell isolation kit (Miltenyi) and stimulated with anti-CD3 (5 μg ml$^{-1}$) and anti-CD28 (2 μg ml$^{-1}$) for 2 days followed by resting overnight before 20 minutes of incubation with anti-CD3 (0.2 μg ml$^{-1}$) and/or anti-ICOS (5 μg ml$^{-1}$) and cross-linking with goat anti-hamster Ab (20 μg ml$^{-1}$) for 8 h. RNA was prepared with the RNeasy plus micro kit according to manufacturer's instructions (Qiagen). RNA amplification, labeling and hybridization to Mouse Gene 1.0 ST Array (Affymetrix) were performed at the Microarray Core Facility of Dana Farber Cancer Institute.

Quantitative RT-PCR

RNA was extracted using RNeasy plus micro kit (Qiagen). Relative quantification real time PCR was performed with TaqMan gene expression assays [Spp1 (Mm00436767_m1), Bcl6 (Mm00477633_m1), Prdm1 (Mm00476128_m1), Rps18 (Mm02601777_g1)] and RNA-to-CT™ 1-Step Kit (Life Technologies). All results were first normalized to those of the Rps18 control and are presented as normalized expression for the sample relative to the appropriate comparison condition as indicated in legends.

LCMV-Armstrong Infection

Mice were infected i.p. with 2×10$^5$ PFU LCMV-Armstrong, as described previously[47]. Spleens were harvested at the indicated time post-infection and analyzed by flow cytometry.

Statistical Analyses

Statistical analyses were performed using Student's t-test or Mann-Whitney test with GraphPad Prism V6 as indicated. Error bars indicate mean±SEM. A P value <0.05 was considered to be statistically significant (*=<0.05, =<0.01, *=<0.001).

Results

Figure 2A:
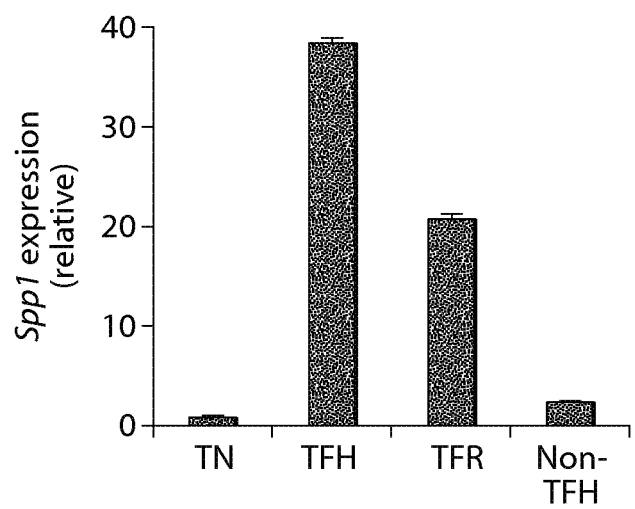
FIGS. 2A-2D show OPN-i-deficiency impairs generation of GC B cells and $T_{FH}$-dependent Ab response.
Figure 2A:
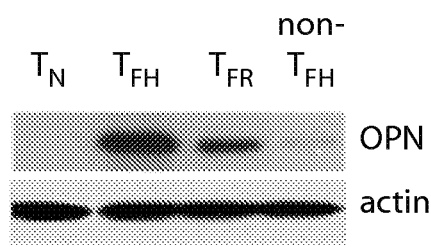
Figure 10:
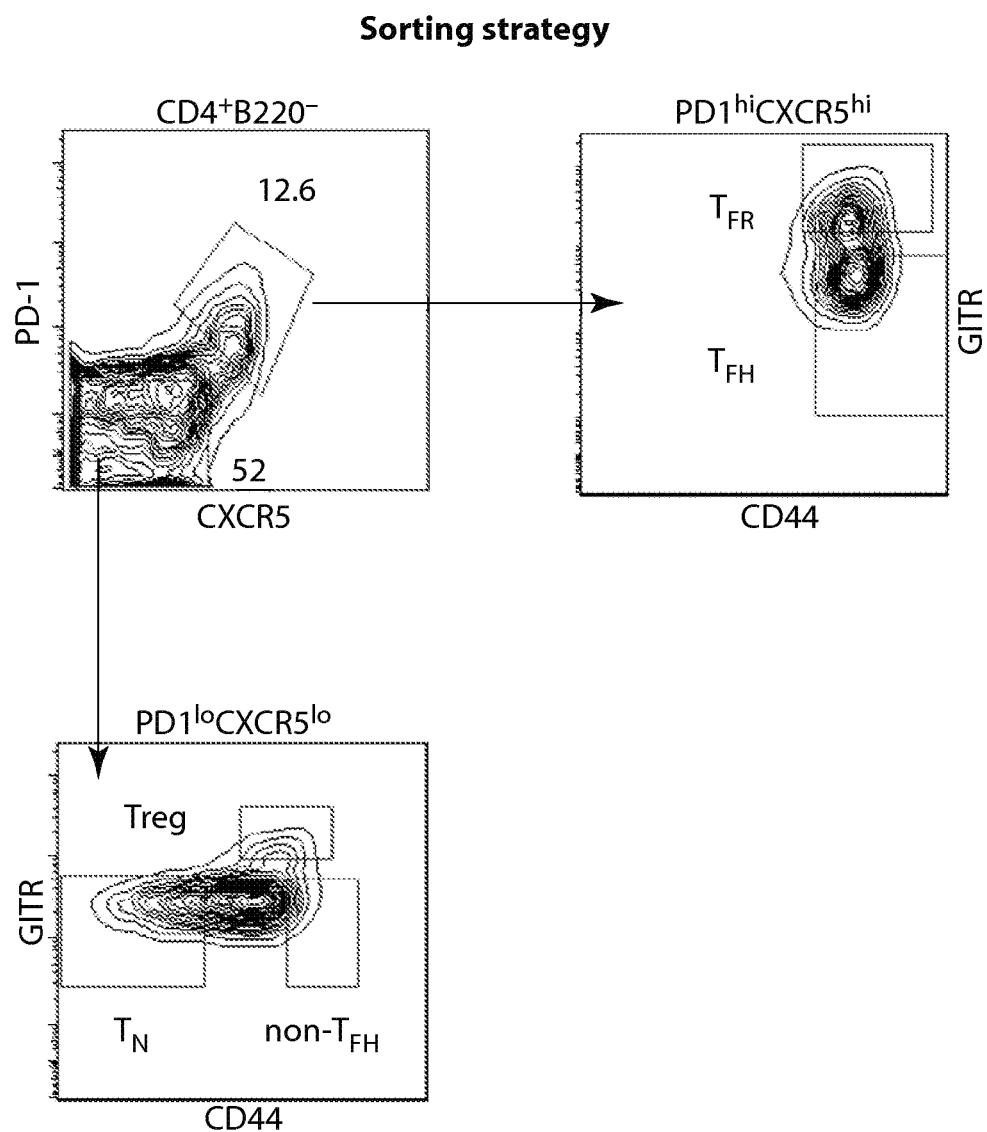
FIG. 10 shows the sorting strategy. FACS plots showed how to isolate different CD4⁺ $T_H$ populations from B6 or OPN-i KI mice after immunization with KLH in CFA. $T_N$: CD4⁺CD44$^{lo}$ CXCR5$^{lo}$ PD-1$^{lo}$ GITR⁻ naïve cells; $T_{FH}$: CD4⁺CD44$^{hi}$CXCR5⁺PD-1⁺GITR⁻ cells; $T_{FR}$: CD4⁺CD44$^{hi}$CXCR5⁺PD-1⁺GITR⁺ cells; Non-$T_{FH}$: CD4⁺CD44$^{hi}$CXCR5$^{lo}$ PD-1$^{lo}$ GITR⁻ cells; Treg: CD4⁺CD44$^{med}$CXCR5⁻PD-1⁻GITR⁺ cells.

OPN-i-Deficiency Impairs Generation of GC B Cells and T$_{FH}$-Dependent Ab Responses Although dysregulation of OPN has been strongly correlated with autoantibody production[17, 23], the underlying mechanism has not been clearly defined. Because OPN is expressed in activated T cells, the OPN RNA and protein expression by different CD4$^+$ T subsets after immunization with Keyhole limpet hemocyanin (KLH) precipitated in complete Freund's adjuvant (CFA) was initially analyzed. It was noted that OPN was expressed most abundantly by the T$_{FH}$ and T$_{FR}$ CD4$^+$ subsets compared with other CD4$^+$ T-cell subsets (FIG. 2A and FIG. 10), suggesting a potential contribution of OPN to the development of these follicular effector and regulatory T cells.

Figure 11A:
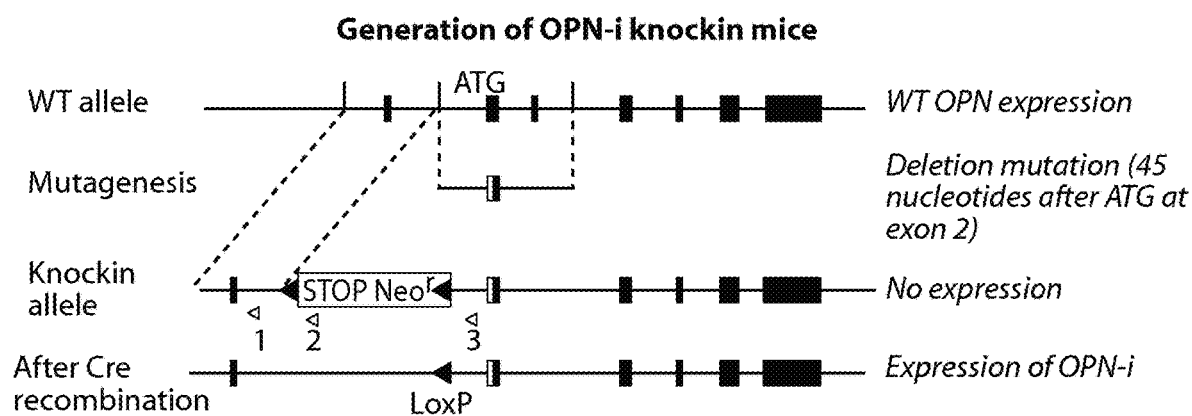
FIGS. 11A-11E depict the generation and confirmation of OPN-i knock-in mice.
Figure 11B:
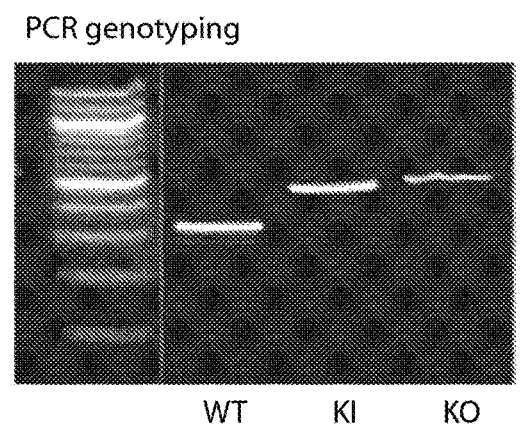
Figure 11C:
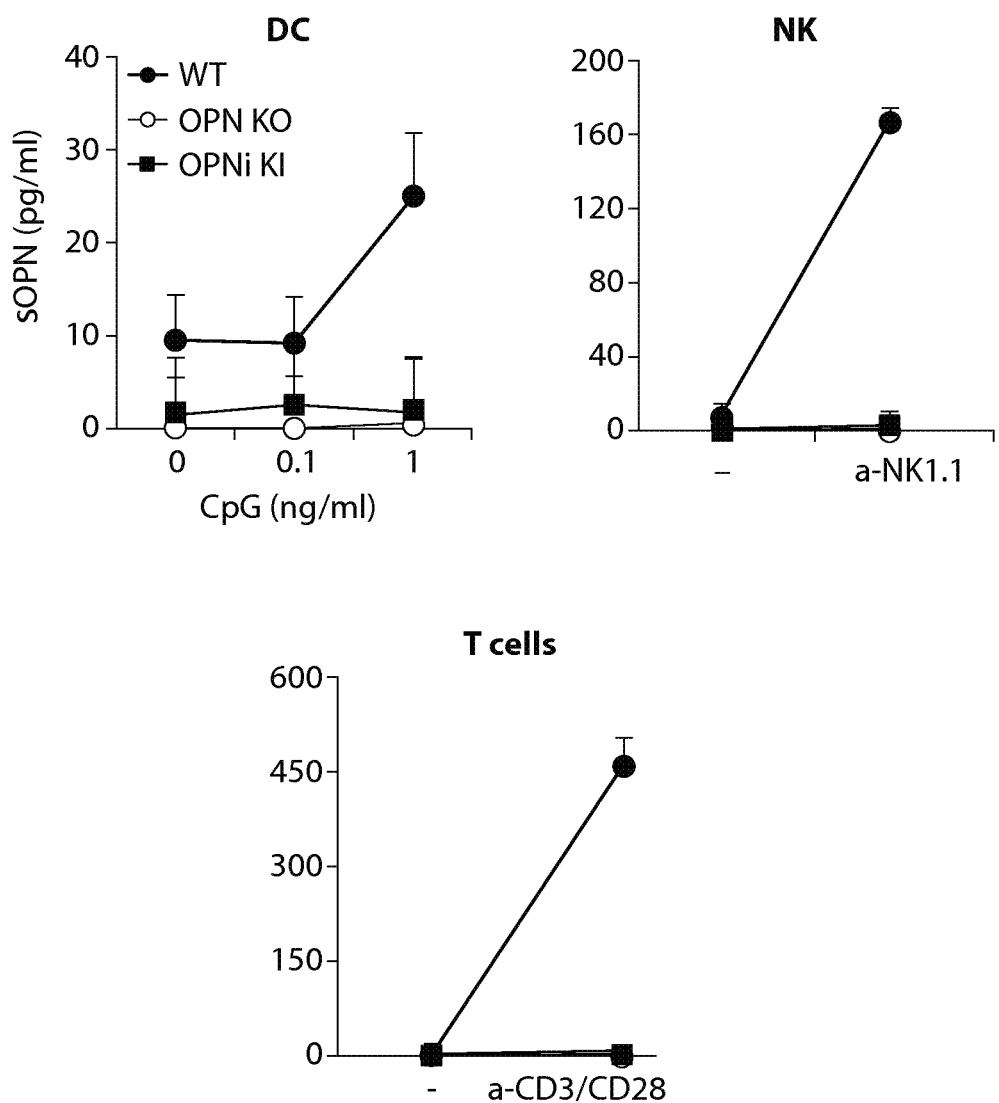

To define the contribution of OPN isoforms, a knock-in allele that allows expression of the OPN-i isoform[24] after excision of a STOP cassette following Cre/loxP-mediated recombination (OPN-i$^{flstop}$) was generated (FIG. 11A). Both the OPN-i$^{flstop}$ P Cre$^+$ and Cre$^-$ mice were developmentally indistinguishable from OPN-i$^{+/+}$ (WT) littermates and PCR analysis confirmed expression of WT and mutant Spp1 alleles (FIG. 11B). Secreted OPN was not detectable in supernatants of freshly isolated or activated T-cells, DC, and NK cells from either OPN-i$^{flstop}$ P Cre$^+$ (i.e., OPN-i KI) mice or OPN-i$^{flstop}$ P Cre$^-$ (i.e., OPN KO) mice (FIG. 11C).

Figure 11D:
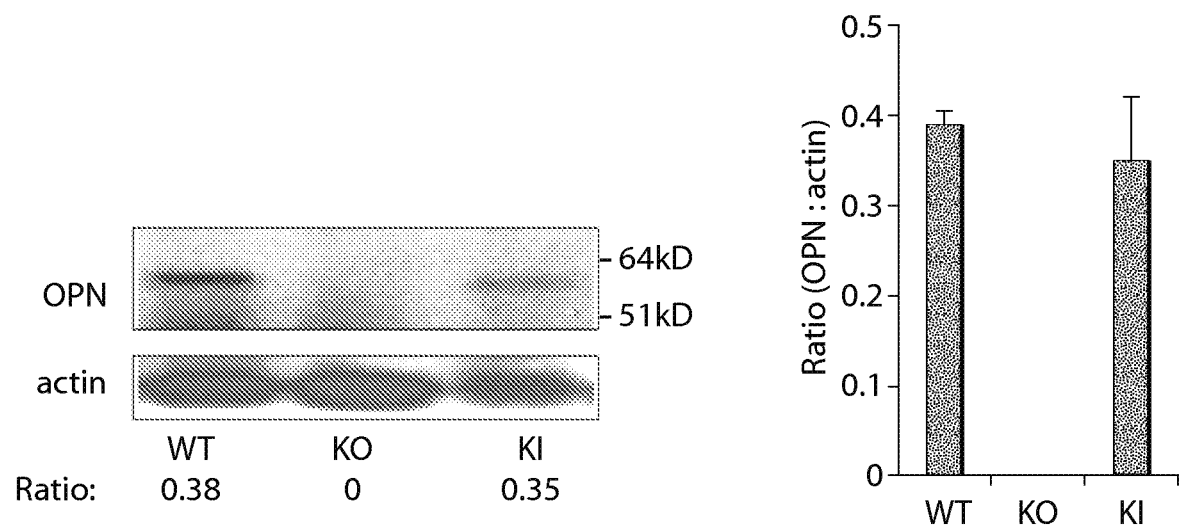
Figure 11E:
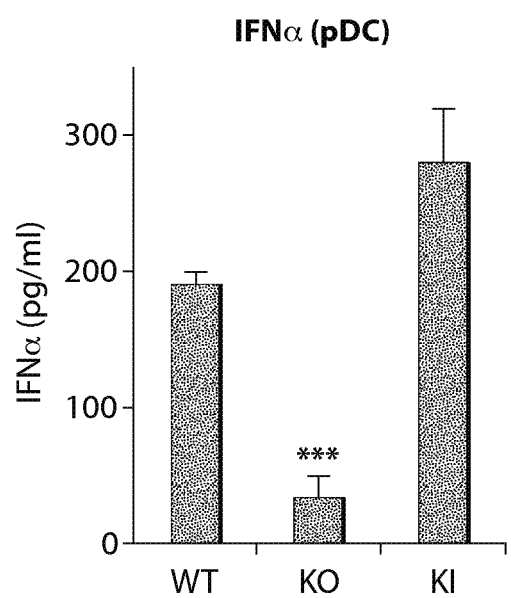

Moreover, immunoblot analysis of splenocyte lysates revealed equivalent intracellular expression of OPN protein by cells from OPN-i KI and OPN WT donors (FIG. 11D). Expression of intracellular (OPN-i) but not secreted (OPN-s) OPN by plasmacytoid dendritic cells (pDC) is essential for efficient production of IFN-α after TLR ligation[20]. Activated pDC from OPN-i KI and WT mice produced similar high levels of IFN-α while pDC from OPN KO donors produced virtually no IFN-α (FIG. 11E), confirming the functional OPN-i KI phenotype.

Figure 2B:
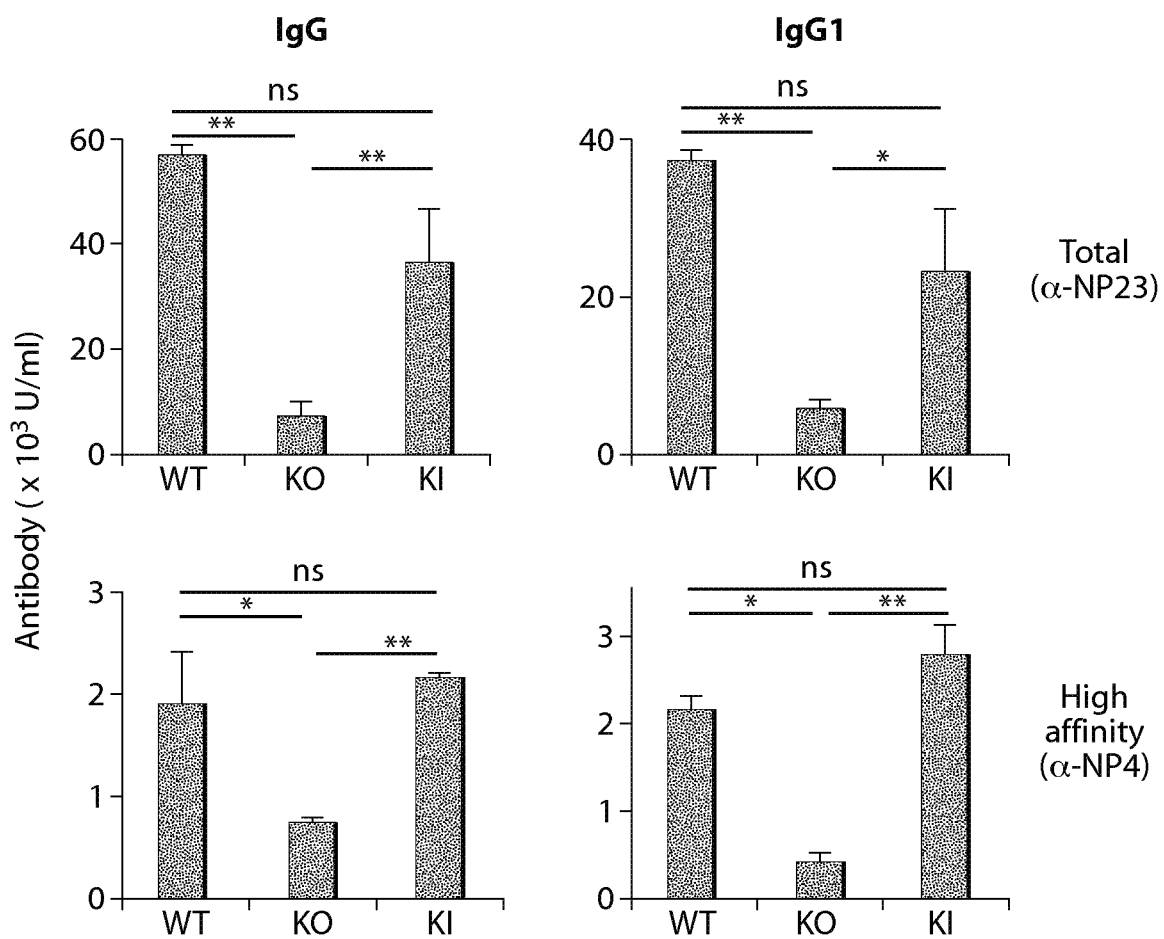
Figure 2C:
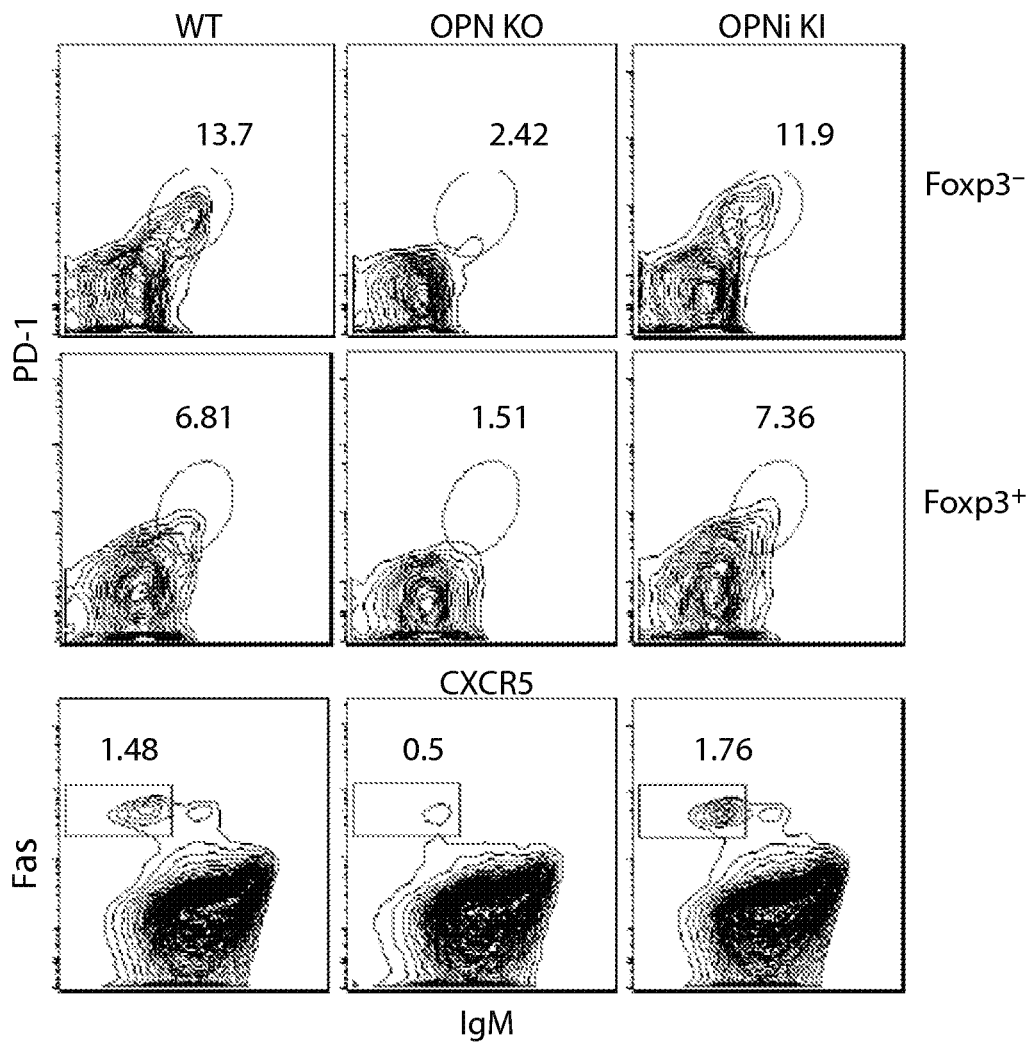
Figure 2D:
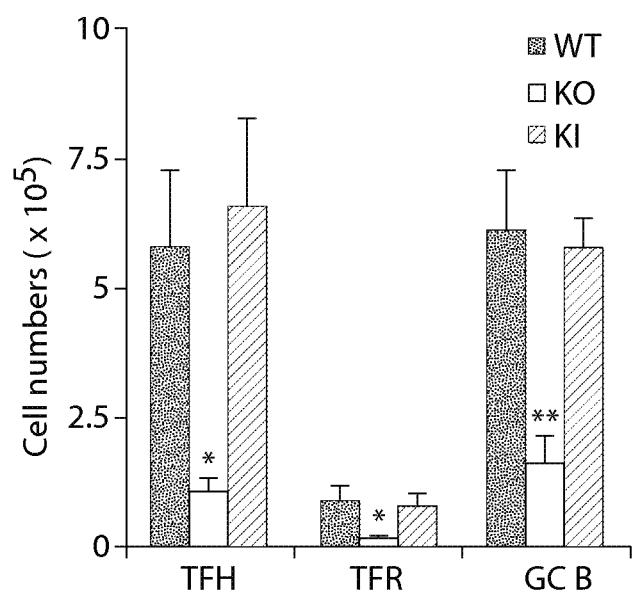
Figure 12A:
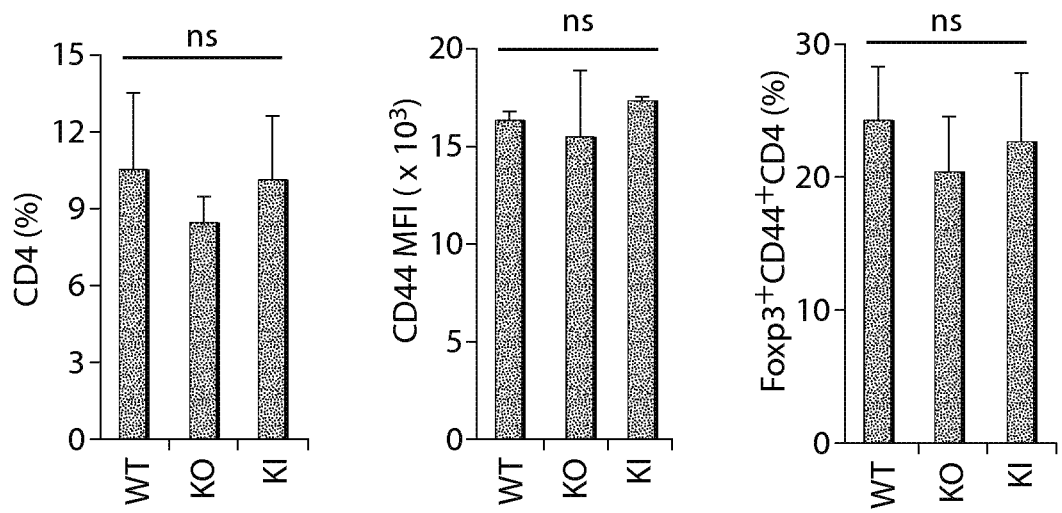
FIGS. 12A-12F show that OPN-i-deficiency does not affect B cell activity nor other $T_H$ cell differentiation. FIG.

Next, the $T_{FH}$ and $T_{FR}$ cell profiles of OPN WT, OPN KO and OPN-i KI mice that expressed an OT-II TCR transgene specific for an OVA peptide after immunization with 4-hydroxy-3-nitrophenyl linked to OVA (NP-OVA) were compared. Both total and high-affinity antibody responses of OPN-deficient mice were reduced by 80-90% compared with the OPN WT response (FIG. 2B) and OPN-i expression by OPN-i KI mice restored antibody titers to levels similar to WT littermates. Although T cell activation was not obviously impaired according to CD44 expression (FIG. 12A), OPN-i deficiency was associated with defective formation of $T_{FH}$ (but not non-$T_{FH}$ CD4) and $T_{FR}$ cells (but not FoxP3+ Treg (FIG. 12A) and GC B cells (FIG. 2C, 2D). These findings suggest that expression of the intracellular OPN isoform is essential for both $T_{FH}$ and $T_{FR}$ cell formation and for $T_{FH}$-associated high affinity antibody responses.

The OPN-i-Deficient $T_{FH}$ and $T_{FR}$ Phenotype is Cell-Intrinsic

Figure 3A:
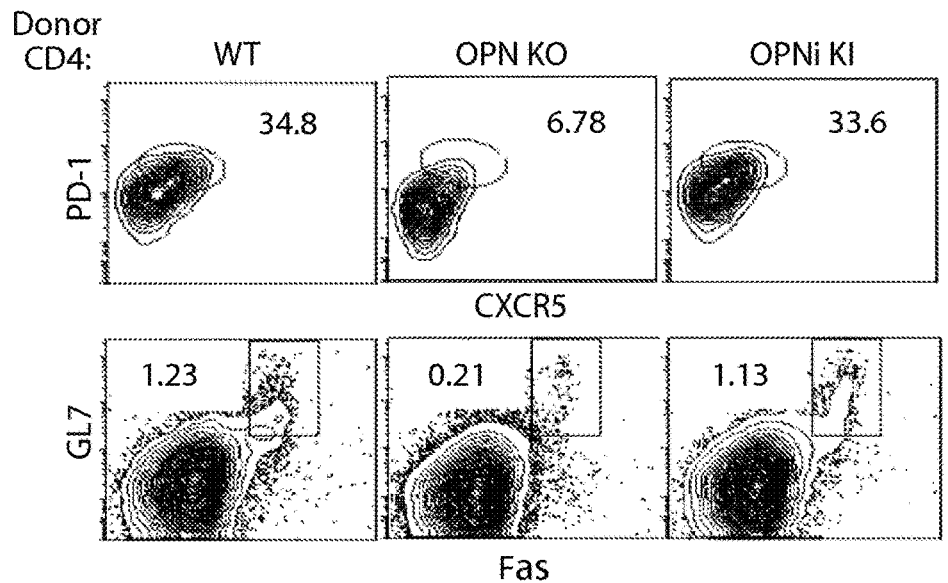
FIGS. 3A-3F show that the OPN-i-deficient $T_{FH}$ and $T_{FR}$ phenotype is cell-intrinsic.
Figure 3B:
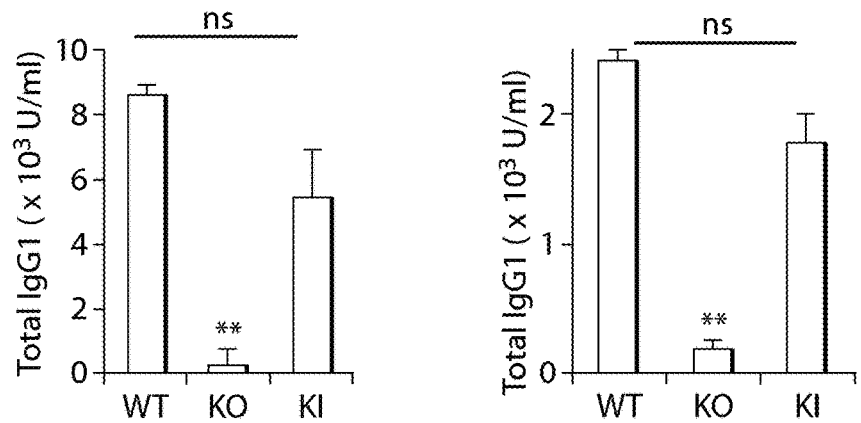
Figure 3C:
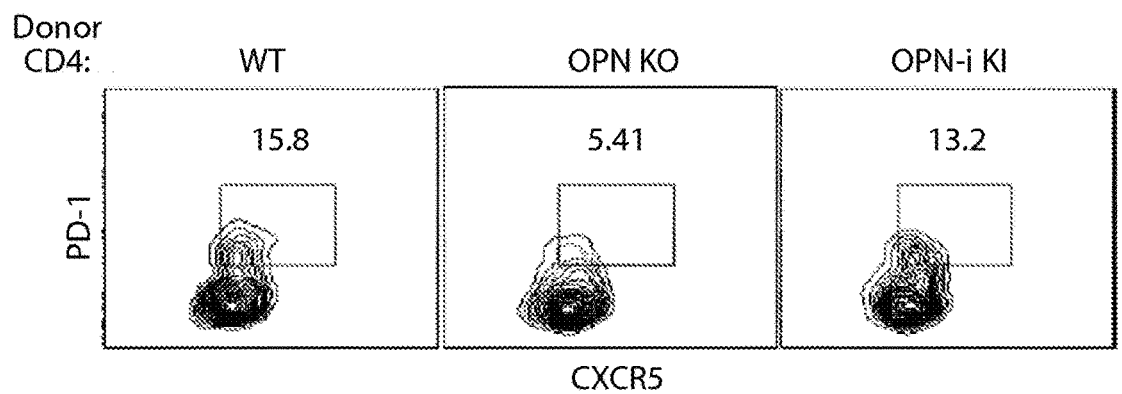
Figure 3D:
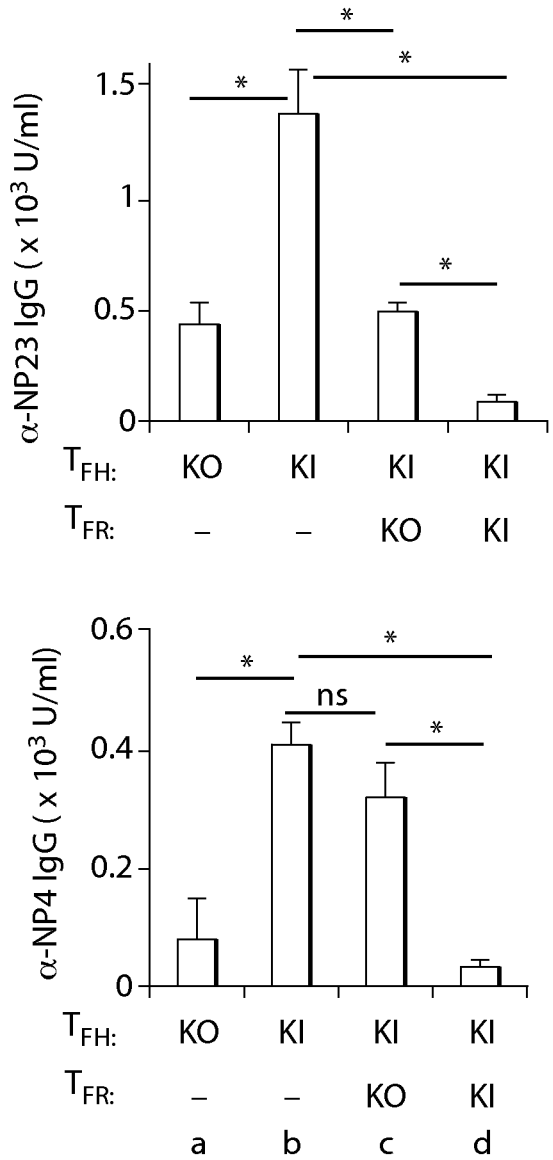
Figure 3E:
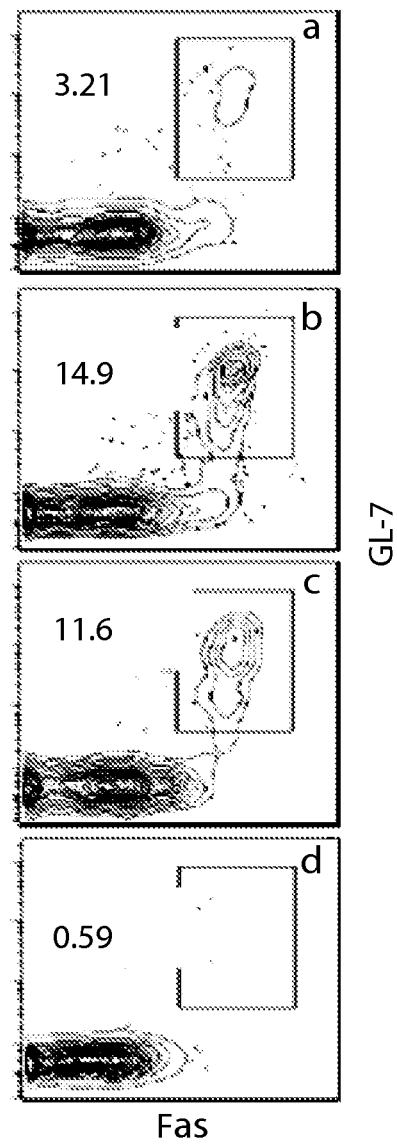
Figure 3F:
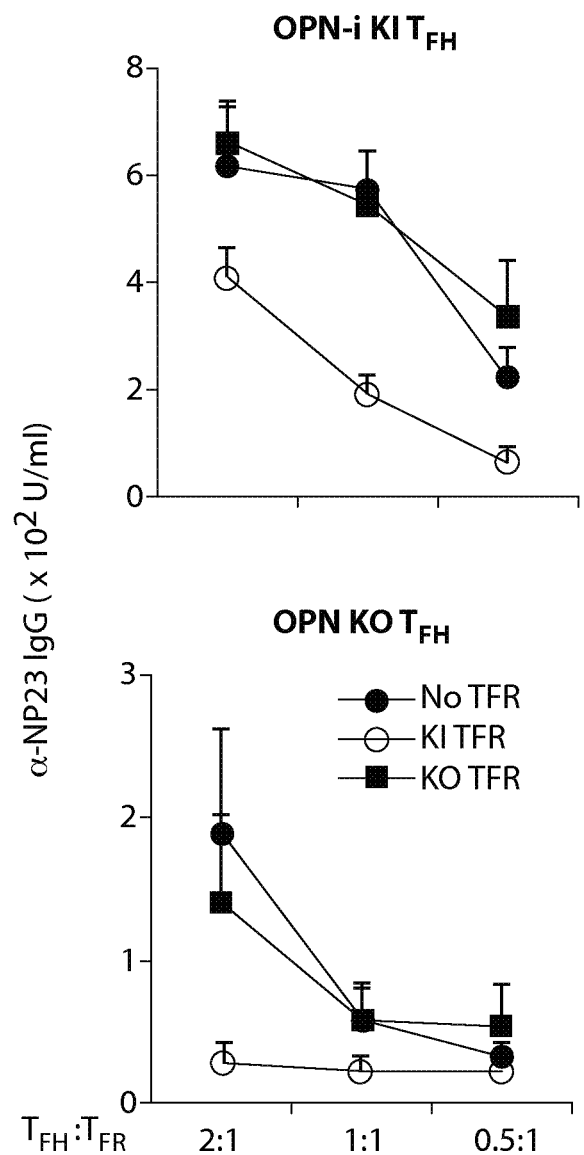
Figure 12B:
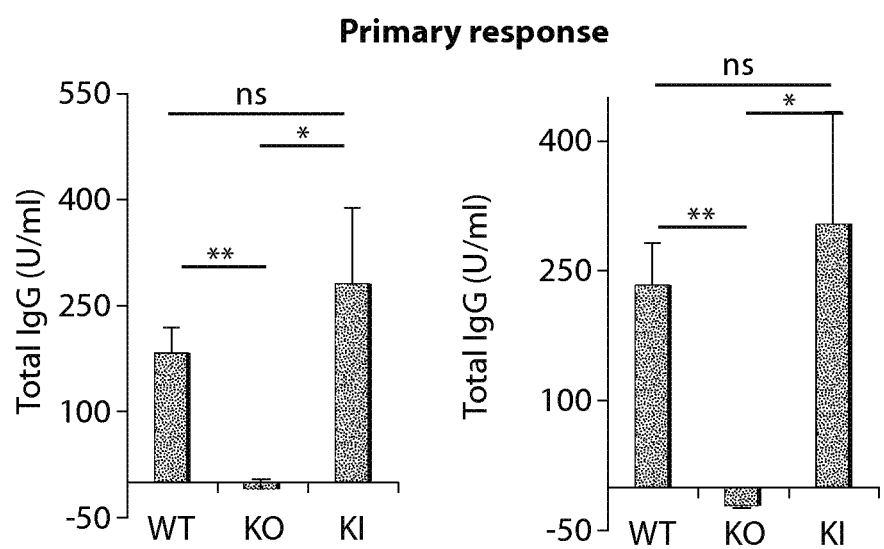
Figure 12C:
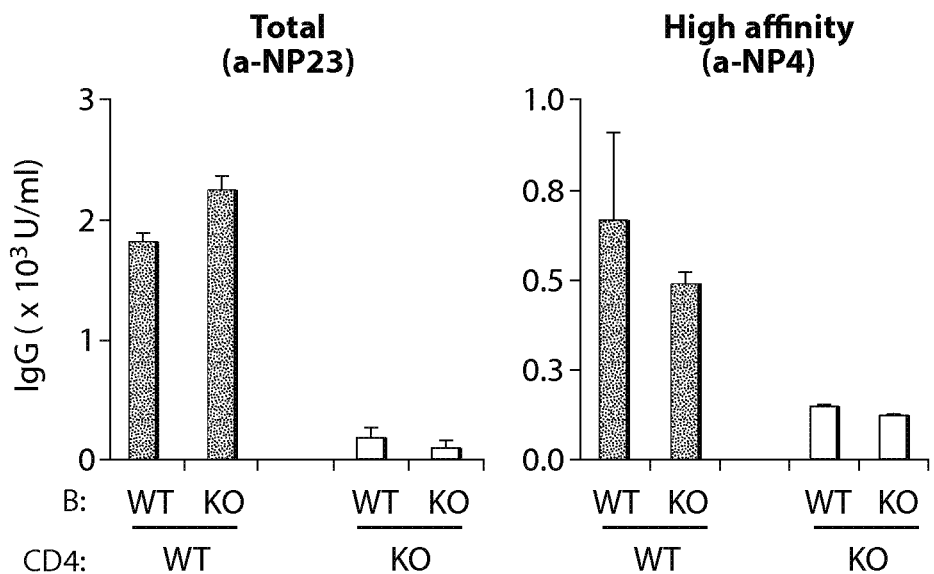

The OPN KO phenotype represents a $T_{FH}$ cell intrinsic defect, since OT-II×OPN$^{-/-}$ CD4+ T cells were defective in helper activity after adoptive transfer with B cells into Rag2$^{-/-}$Prf1$^{-/-}$ hosts and immunization with NP-OVA. Substantially reduced anti-NP primary and secondary responses and diminished $T_{FH}$ and GC B cell formation in hosts reconstituted with OPN KO CD4+ T cells compared to the response of Rag2$^{-/-}$Prf1$^{-/-}$ hosts reconstituted with OPN-i KI or OPN WT CD4+ T cells were observed (FIG. 3A, 3B; FIG. 12B). Defective antibody responses of OPN KO mice did not reflect impaired B cell responses secondary to diminished OPN-i expression: OPN KO and WT B cells produced equivalent antibody responses after co-transfer with WT CD4+ T cells (FIG. 12C). Transfer of CD25+ CD4+ T cells that contain natural Foxp3+ Treg into TCRα$^{-/-}$ mice revealed a reduction of $T_{FR}$ cell formation in OPN KO mice after immunization with KLH and CFA (FIG. 3C). Further analysis showed that transfer of OPN-deficient $T_{FR}$ cells resulted in a greater expansion of GL7+Fas+ GC B cells and significantly higher amounts of NP-specific total and high-affinity IgG compared with transfer of the same numbers of $T_{FR}$ cells from OPN-i knock-in mice (FIG. 3D, 3E), suggesting that OPN-i deficiency impaired $T_{FR}$ suppressive activity on a per-cell basis in vivo. Impaired $T_{FR}$ regulatory activity was not apparent from the dramatically reduced antibody response of intact OPN KO mice, which reflected the marked defect in $T_{FH}$ cell-mediated GC responses (FIG. 1B-1D), indicating that the ratio of $T_{FH}$ cells to $T_{FR}$ cells, not the individual cell type, is more critical in determining the extent of antibody responses. Transfer experiments using different ratios of $T_{FH}$ cells to $T_{FR}$ cells further confirmed that the magnitude of $T_{FR}$ cell-mediated suppression depended on the extent of $T_{FH}$-driven antibody responses (FIG. 3F). Taken together these results indicate that the contribution of OPN-i to follicular T cell-dependent activity reflects a CD4+ T cell-intrinsic function.

OPN-i-Deficiency Results in Impaired Bcl6 Protein Expression

Figure 4A:
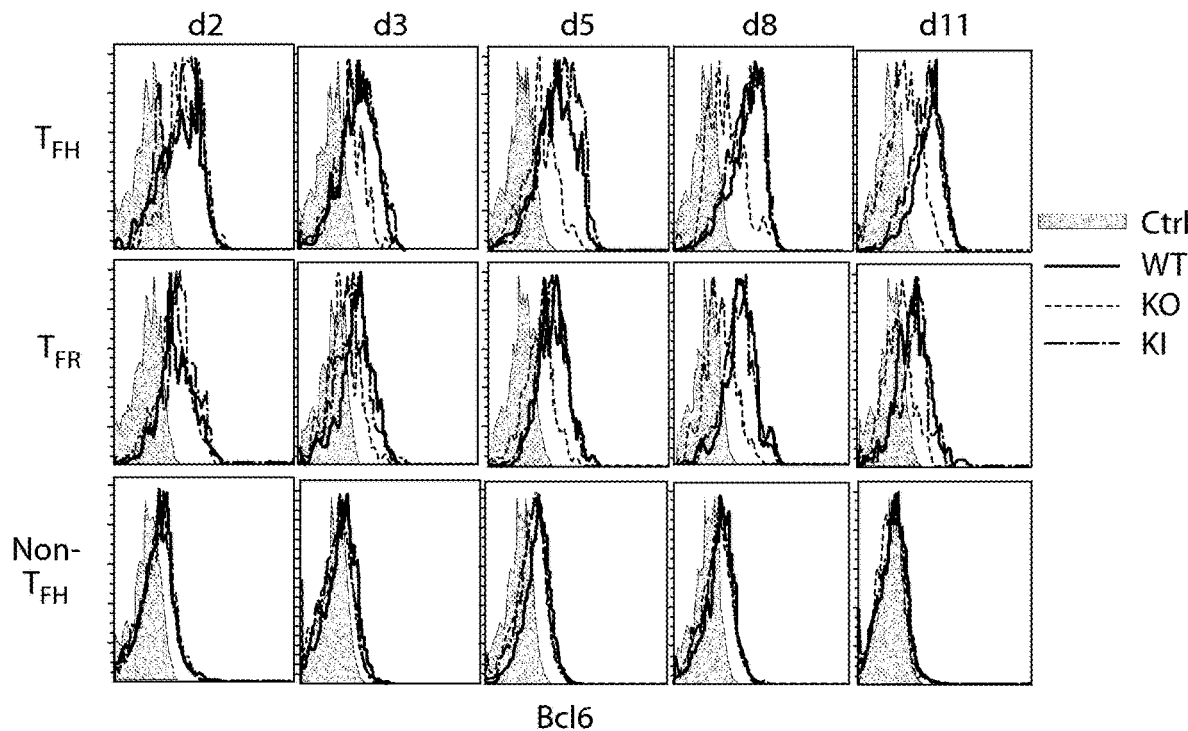
FIGS. 4A-4E comprise the OPN-i-deficiency results in impaired Bcl6 protein expression.
Figure 4B:
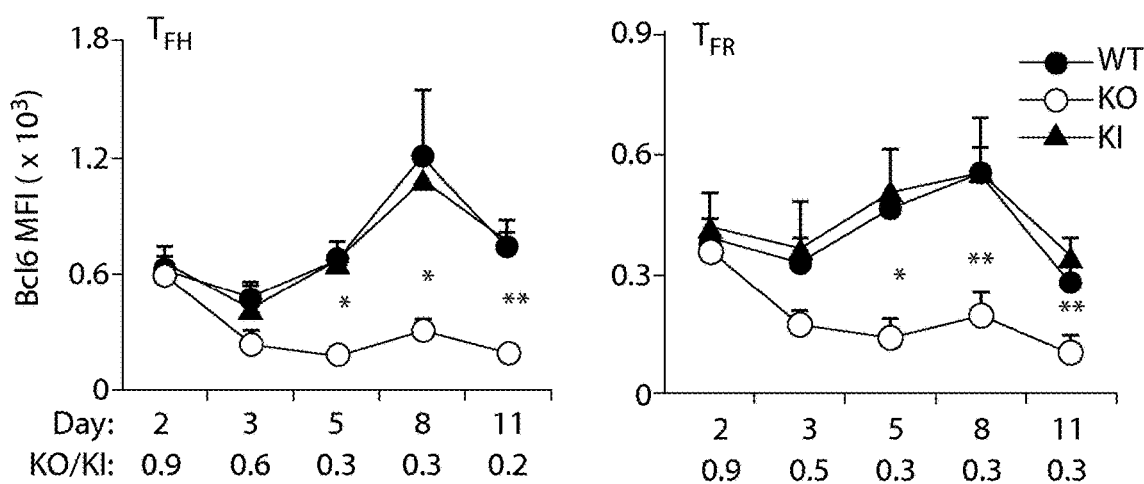
Figure 12D:
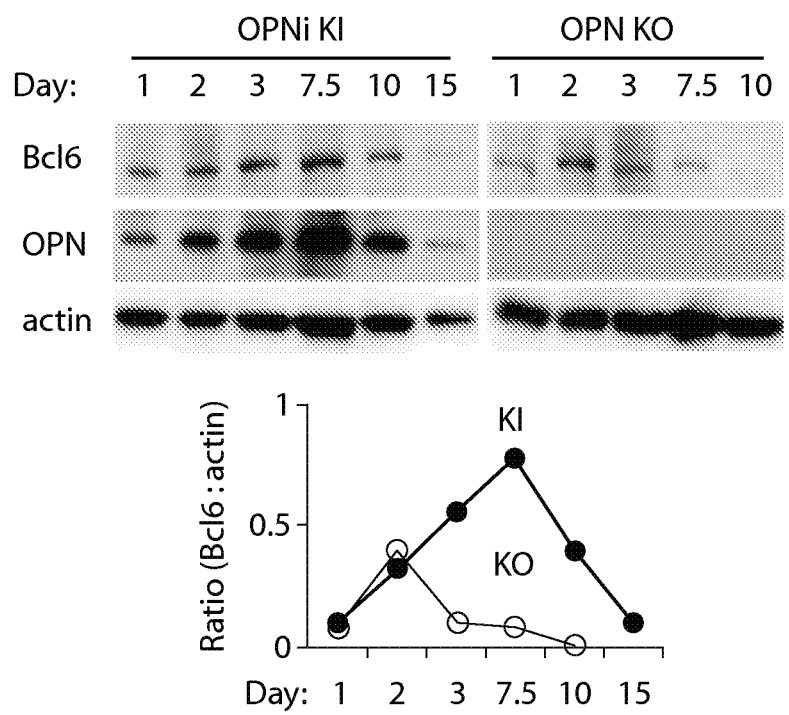

Bcl6 is the central transcription factor that directs $T_{FH}$ and $T_{FR}$ cell differentiation. It was investigated whether the impaired follicular T cell response of OPN-i-deficient CD4+ T cells was associated with reduced Bcl6 expression. Analysis of Bcl6 protein expression during $T_{FH}$ cell development in vivo after KLH immunization revealed that Bcl6 was detectable by day 1, peaked at day 7.5 and waned by day 10 (FIG. 4A, 4B; FIG. 12D), consistent with a previous study[25]. Expression of Bcl6 during $T_{FR}$ cell formation followed similar kinetics, albeit at a lower level (FIG. 4A, 4B). Although OPN deficiency did not alter Bcl6 mRNA levels (FIG. 12E), the OPN deficient response was marked by severely reduced expression of Bcl6 protein that was associated with the decreased frequency of both $T_{FH}$ and $T_{FR}$ cells by day 3 and thereafter (FIG. 4A-4D; FIG. 12D). Notably, OPN-i-deficiency did not affect expression of other $T_H$ lineage-specific transcription factors including Blimp1 expression[1] (FIG. 12E, 12F), suggesting that OPN-i may selectively regulate early commitment and differentiation of follicular T cells but not other $T_H$ subsets. These findings suggest that although OPN-i does not contribute to Bcl6 expression at the mRNA level, it may contribute to expression of Bcl6 protein after early commitment of $T_{FH}$ and $T_{FR}$ cells.

ICOS Co-Stimulation Upregulates OPN-i Expression

Figure 4C:
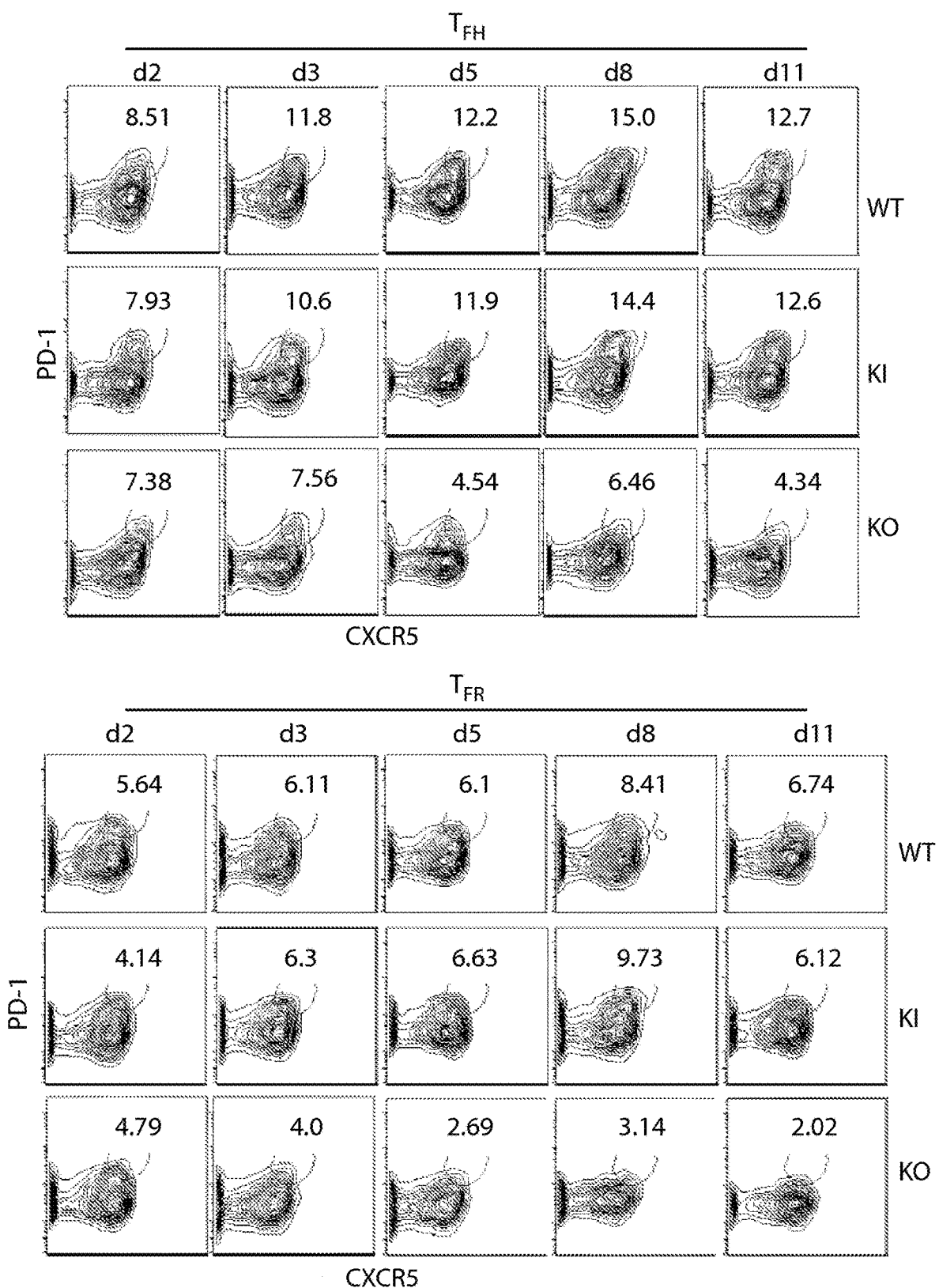
Figure 4D:
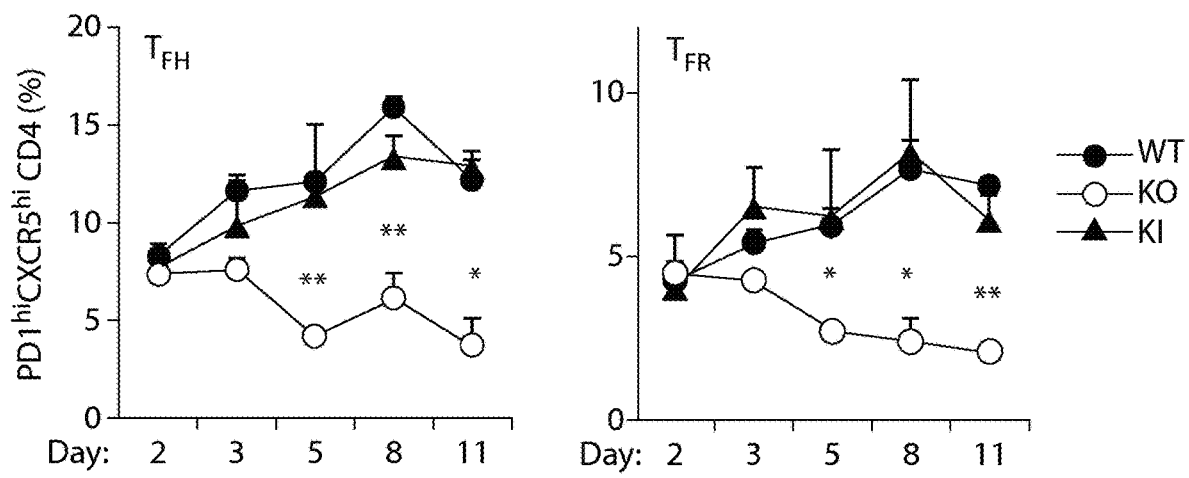
Figure 4E:
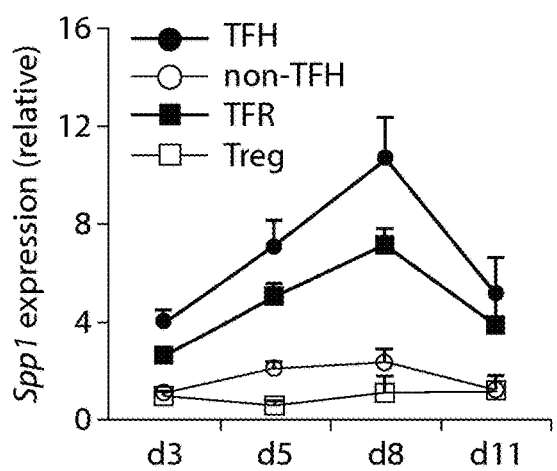
Figure 13A:
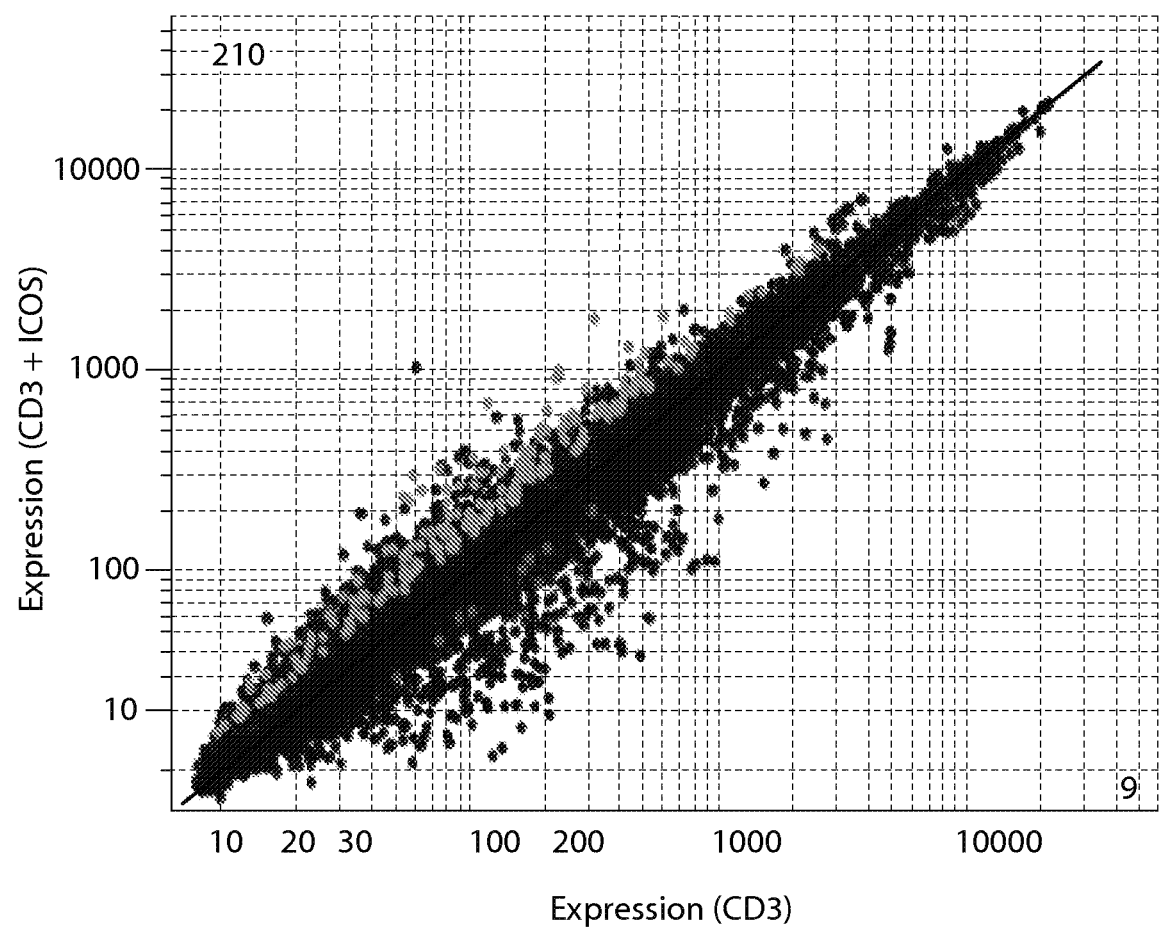
Figure 13C:
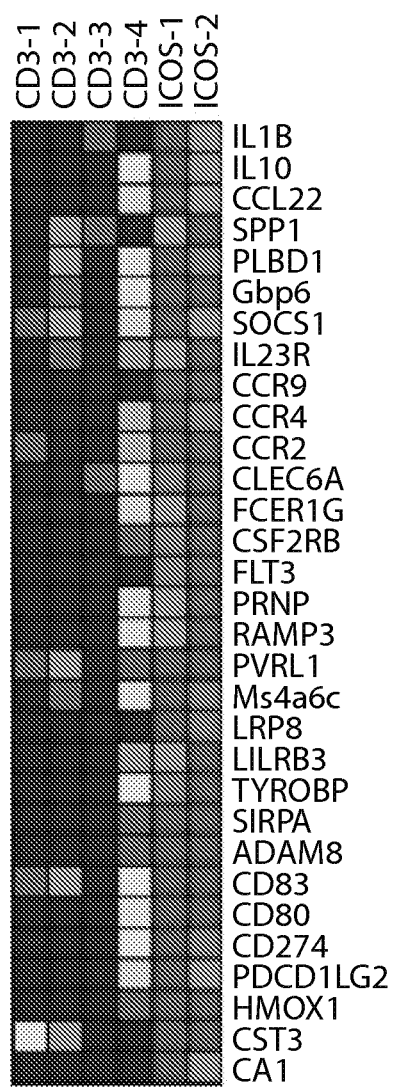
Figure 14A:
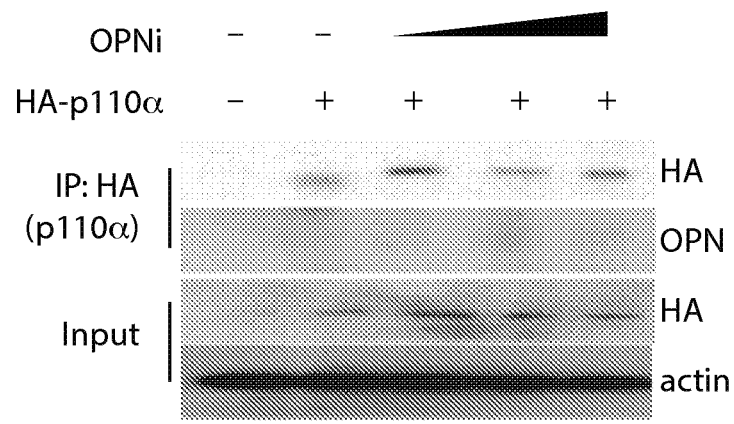
Figure 14B:
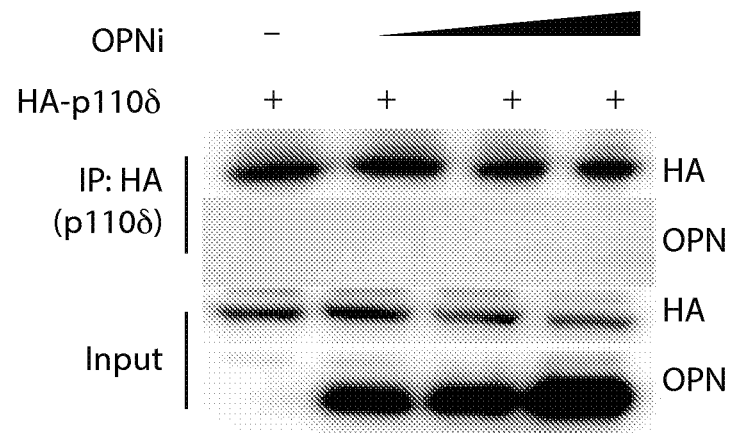

ICOS co-stimulation is essential for the induction and maintenance of Bcl6 expression during $T_{FH}$ cell differentiation and is required for $T_{FR}$ cell formation[5, 26, 27]. Expression of OPN-i and Bcl6 by $T_{FH}$ cells and $T_{FR}$ cells followed similar kinetics and Bcl6 was expressed at reduced levels by residual CXCR5+PD-1+ cells generated in OPN-deficient mice (FIG. 4A, 4B, 4E; FIG. 12D). These findings opened the possibility that enhanced Bcl6 expression secondary to ICOS signals might require an OPN-i intermediary. A gene profile analysis identified ~210 genes, including OPN (Spp1), that were significantly upregulated by CD4+ T cells 8 h after CD3 and ICOS ligation compared to the expression profile after CD3 ligation alone (FIG. 13A). Pathway analysis (Ingenuity®) of these genes revealed that Spp1 was involved with many biological functions that were related to T-cell activation, antibody production and significantly associated with systemic autoimmune disease (FIG. 13A, 13C). It was confirmed that Spp1 was upregulated at the RNA and protein levels after engagement of ICOS and CD3 compared to CD3 ligation by in vitro-activated CD4+ T cells (FIG. 4A, 4B). Moreover, ICOS$^{-/-}$ CD4+ T cells (both effector and regulatory compartments) failed to upregulate OPN-i as well as Bcl6 compared with ICOS$^{+/+}$ CD4+ T cells after in vivo immunization (FIG. 4C, 4D). The latter finding is consistent with a previous report that ICOS is essential for upregulation of Bcl6 expression[26]. These findings suggested a close relationship of ICOS ligation to increased OPN-i expression during T cell functional differentiation.

ICOS Ligation Promotes an Interaction Between OPN-i and p85α

The PI3K signaling pathway is the major signaling pathway that has been coupled to ICOS ligation. Possibly, upregulation of the OPN-i intracellular protein after ICOS ligation may also facilitate association of OPN-i with the p110/p85 components of the PI3K complex and ICOS-dependent Bcl6 regulation. It was found that OPN-i did not interact with p110α or p110δ and OPN-i deficiency did not affect PI3K-Akt activation as measured by phosphorylated Akt (pAkt) levels nor did it affect the activation of IL-6 signals (FIG. 14A-14D). However, coimmunoprecipitation analysis revealed that (a) OPN-i bound to p85α in transfected cell lines and after activation of primary CD4 cells (FIG. 6A, B) and (b) co-ligation of TCR and ICOS substantially increased the association between p85α and OPN-i (FIG. 6B), suggesting an ICOS-dependent interaction between p85α and OPN-i that might regulate differentiation of Bcl6+ CD4 cells.

Figure 5A:
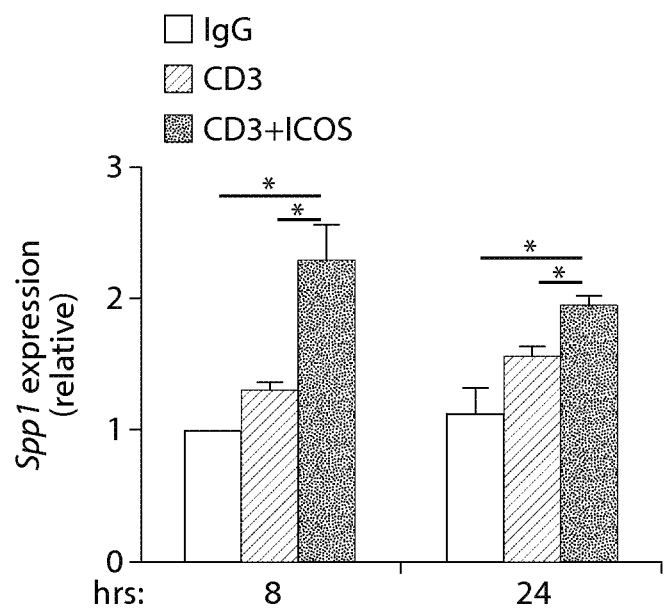
FIGS. 5A-5D show that ICOS co-stimulation upregulates OPN-i expression.
Figure 5B:
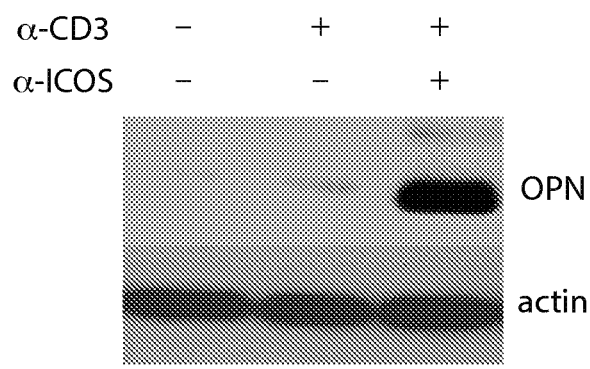
Figure 5C:
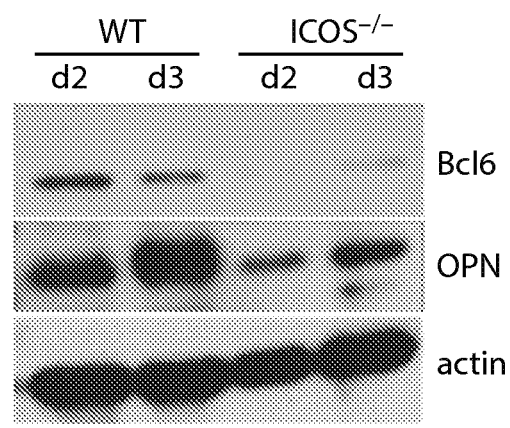
Figure 5D:
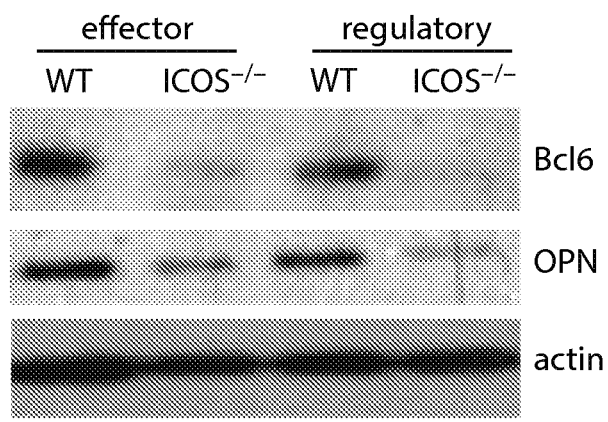

A requirement of p85α as a link between ICOS and Bcl6 upregulation during follicular T cell differentiation was further tested by analysis of p85α-deficient mice. Deletion of the p85α component of PI3K impaired Bcl6 upregulation and $T_{FH}$ development after protein immunization (FIG. 5C, 5D). Moreover, p85α deficiency also diminished Bcl6 expression by $T_{FR}$ cells and impaired $T_{FR}$ cell formation (FIG. 6C, 6D). Possibly, defective p85α expression diminished Bcl6 expression secondary to destabilization of p110 and reduced p110-Akt activation[14]. To test this possibility, in vitro-activated p85α KO CD4+ T cells with retrovirus that expressed a constitutively-active Akt (cAkt) mutant[28] before cell transfer and protein immunization were reconstituted (FIG. 6E, 6F). Although the proportion of CD4+ T cells expressing phosphorylated Akt (pAkt) was increased substantially in cAkt-reconstituted CD4+ T cells (~25% compared to 2% in control vector-expressing CD4 cells) (FIG. 6E), cAkt reconstitution did not significantly increase expression of Bcl6 and CXCR5 by CD4+ T cells compared to cells infected with a control virus (FIG. 6E, 6F). These findings supported the view that ICOS initiated a PI3K (p85α-dependent pathway leading to Bcl6 expression and follicular T cell differentiation that is independent of p110.

p85α Chaperones Nuclear Translocation of OPN-i

Figure 6A:
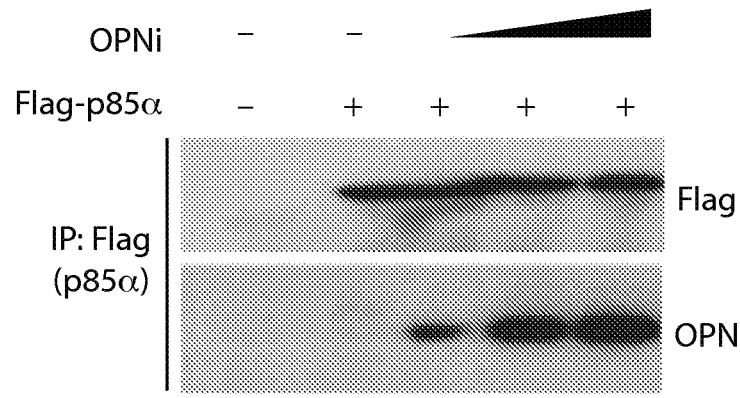
FIGS. 6A-6G show that ICOS ligation promotes an interaction between OPN-i and p85α.
Figure 6B:
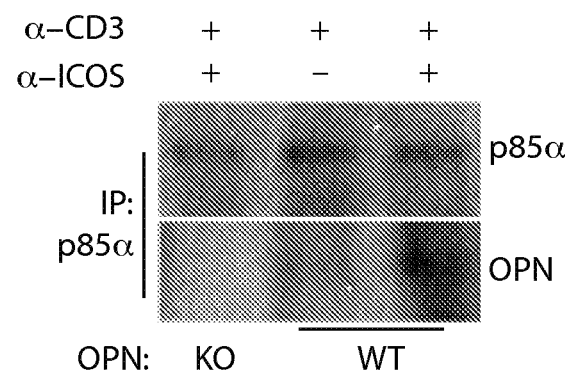
Figure 6C:
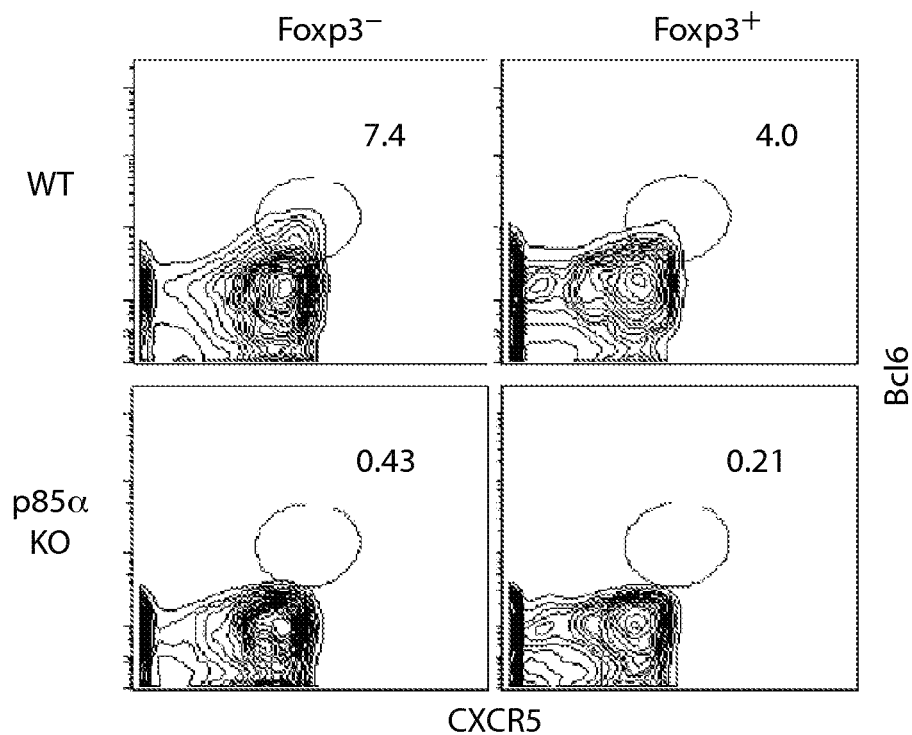
Figure 6D:
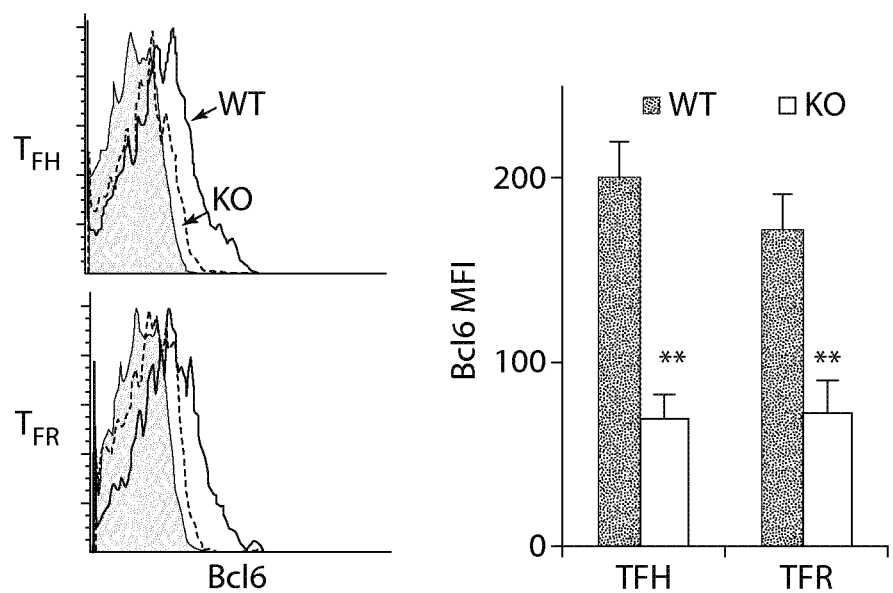
Figure 6E:
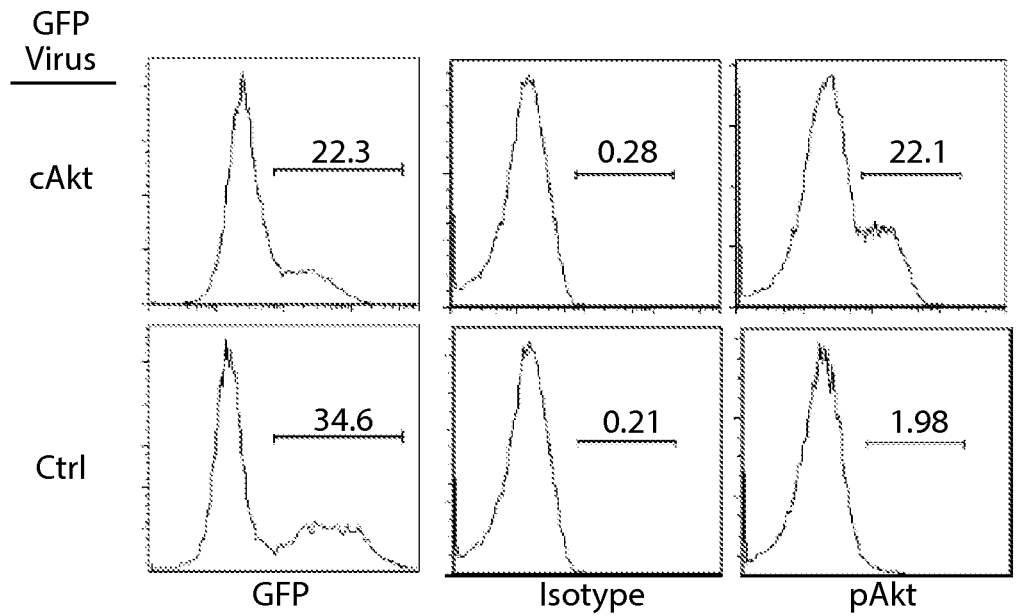
Figure 6F:
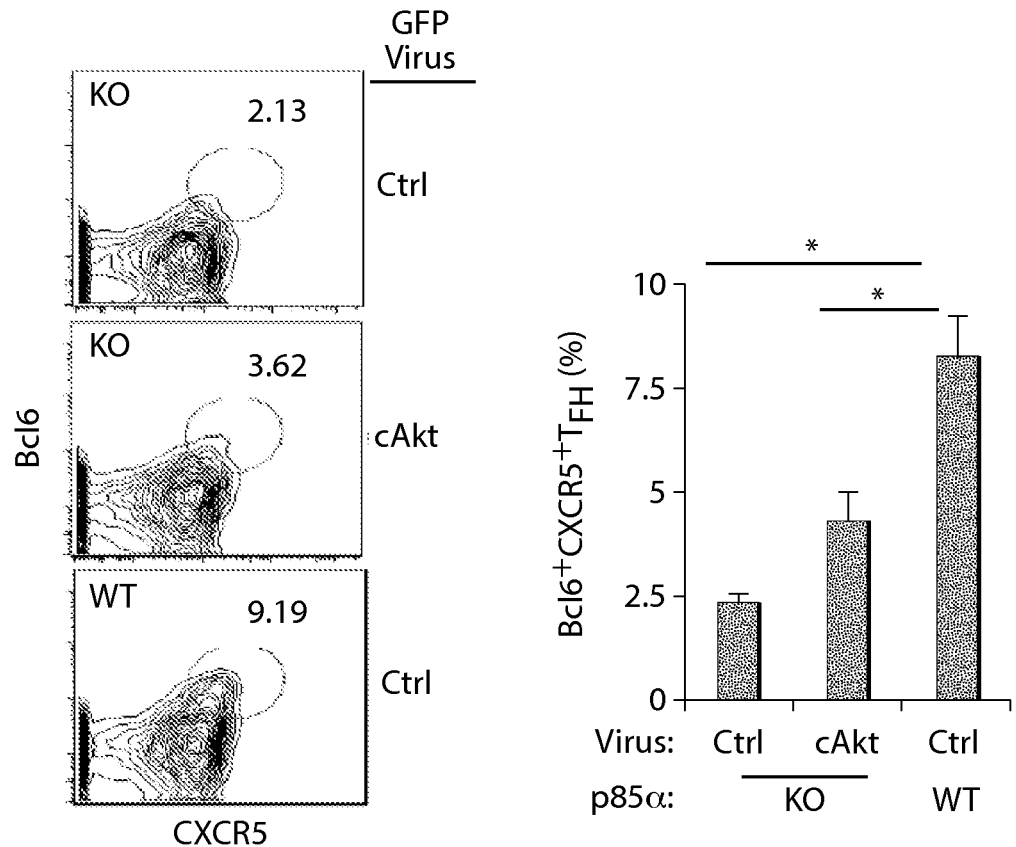
Figure 6G:
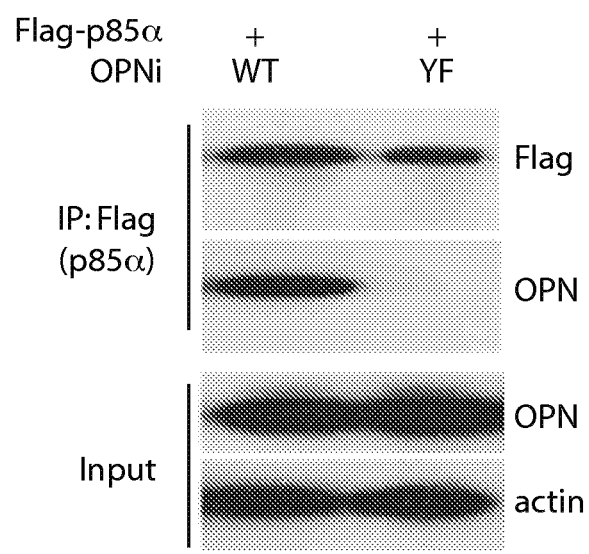

The above findings suggested that a) both p85α and OPN-i contributed to Bcl6-dependent follicular T cell differentiation and b) the two proteins might interact according to immunoprecipitation studies (FIG. 6A, 6B). Next further definition of the potential interaction between p85α and OPN-i was sought. It was found that the p85α-bound fraction of OPN underwent a shift in migration after treatment with protein phosphatases (FIG. 14E), consistent with reports that p85α can recognize phosphorylated proteins. A web-based program (Scansite)[29, 30] suggested an OPN sequence (UniProtKB: P10923) that might interact with the p85α SH2 domain through a tyrosine at OPN position 166 (Y166) (FIG. 14F). It was found that the interaction of p85α with OPN-i required an intact OPN-i Y166 site, since p85α bound to an OPN-i Y166F mutant at substantially reduced levels compared to the OPN-i WT protein (FIG. 6G).

Figure 7A:
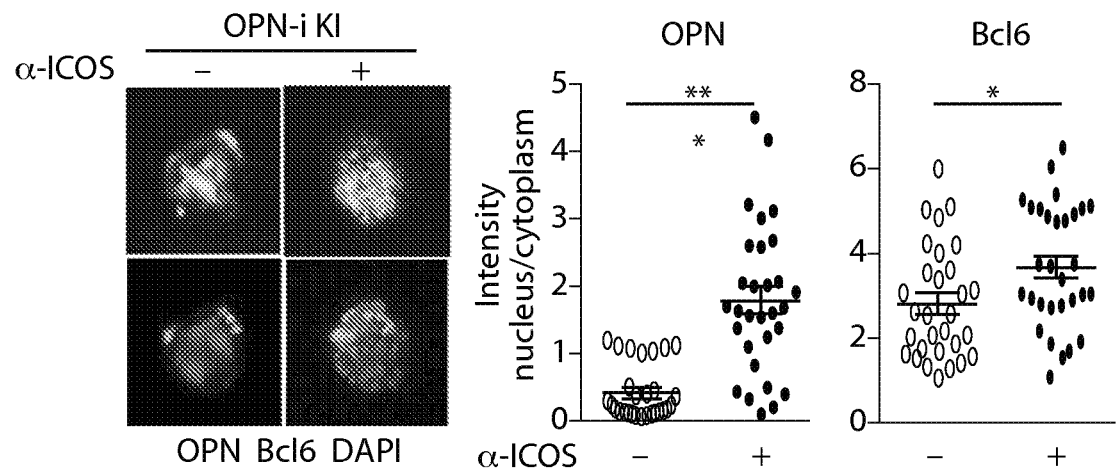
FIGS. 7A-7D depict p85α chaperones nuclear translocation of OPN-i.
Figure 7B:
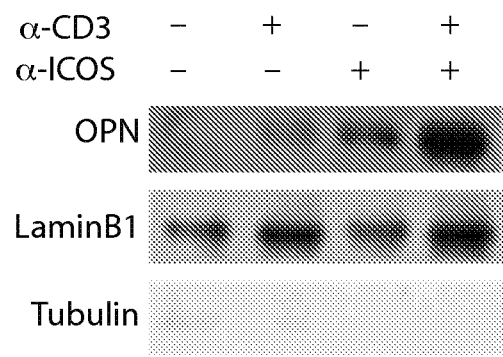
Figure 7C:
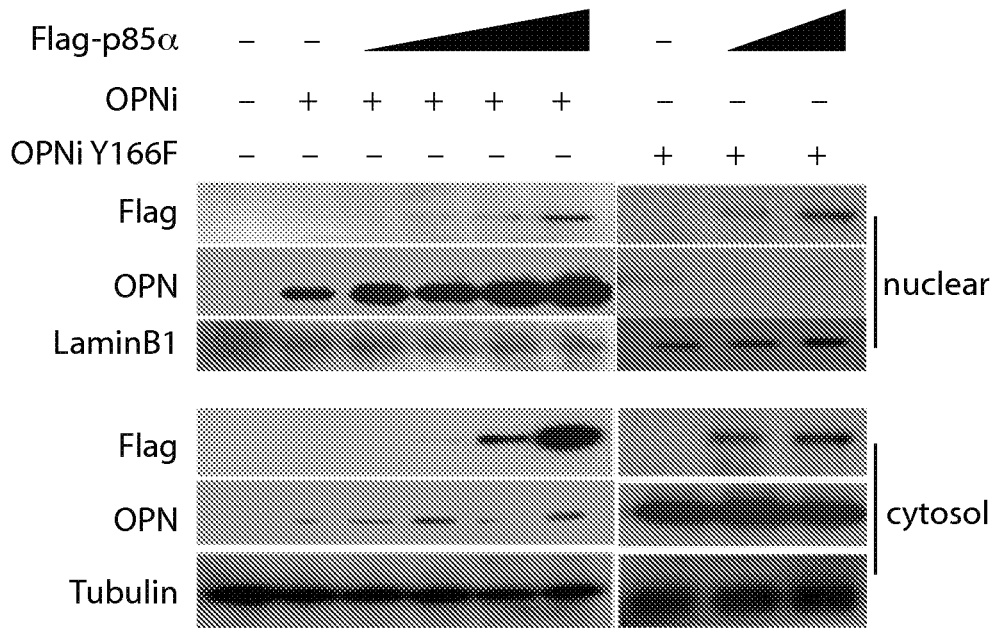
Figure 7D:
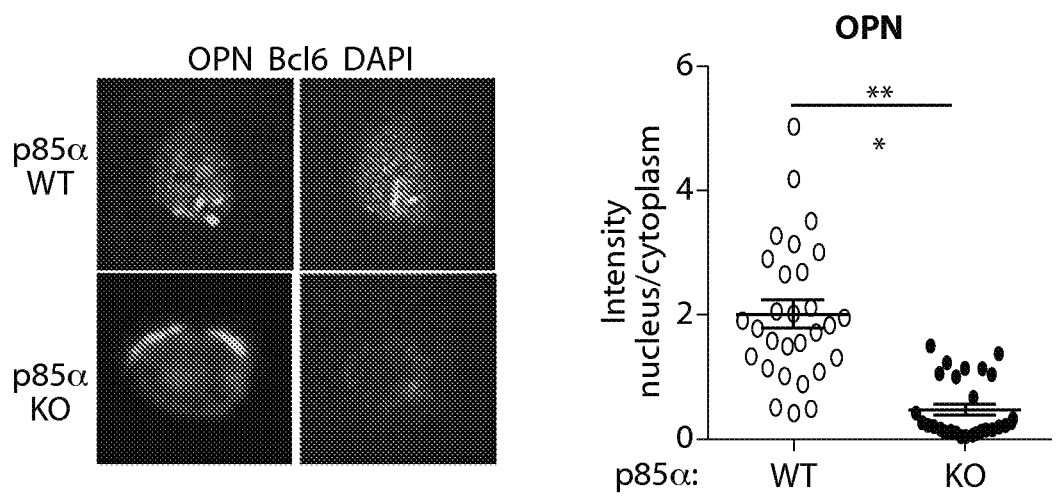
Figure 15A:
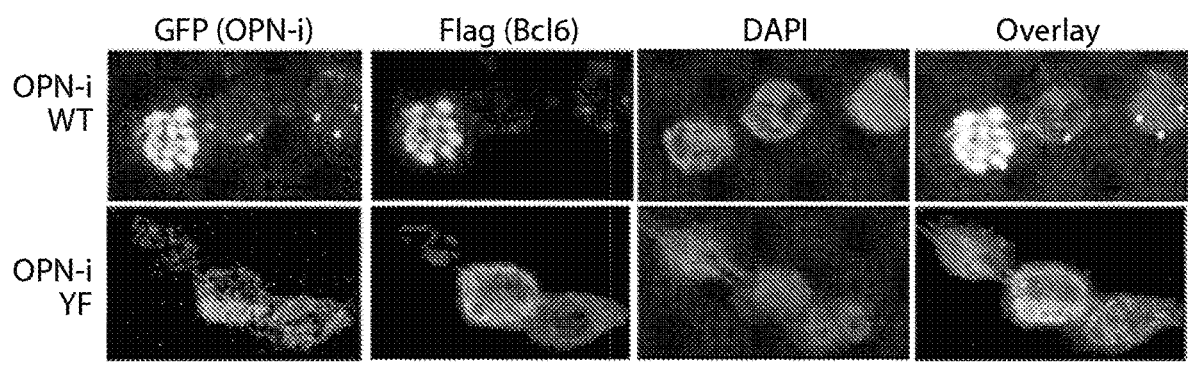
FIGS. 15A-15C show that OPN-i WT, but not Y166F mutant, interacts with Bcl6 in the nucleus.
Figure 15B:
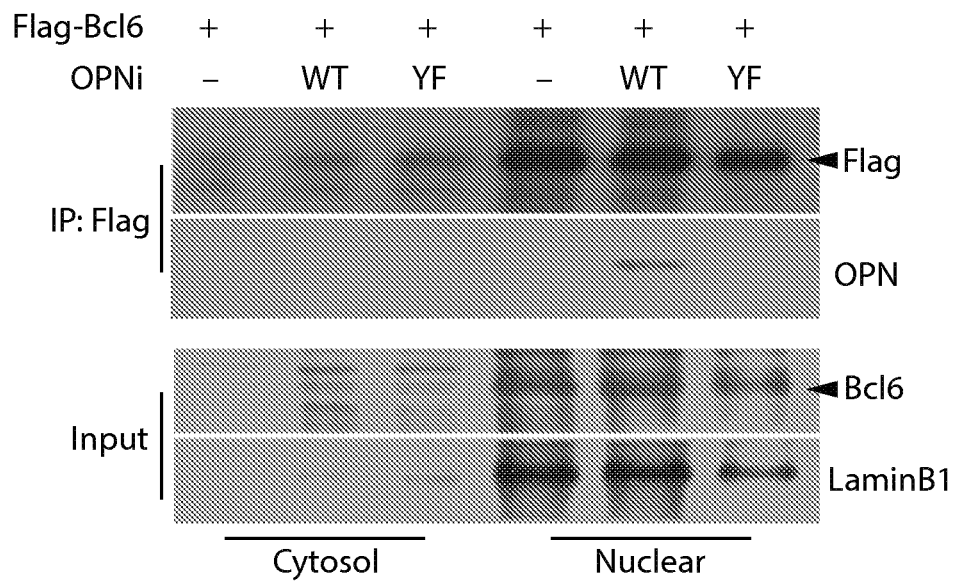

Next, the molecular consequence of the p85α-OPN-i interaction was analyzed. Although OPN-i protein was located mainly within the cytosol of CD4+ T cells in the steady state, the majority of OPN-i protein was detected within the nucleus of CD4+ T cells after ICOS ligation (FIG. 7A, 7B). Since the p85α protein can function as a chaperone to facilitate nuclear translocation of associated partner proteins[15, 16], it was asked whether p85α might assist in the nuclear translocation of OPN-i. Indeed, nuclear accumulation of OPN-i increased in direct proportion to levels of p85α after co-transfection (FIG. 7C), and OPN protein failed to relocate to the nucleus after ICOS ligation of p85α KO CD4+ T cells (FIG. 7D). The interaction between p85α and OPN-i resulting in enhanced nuclear translocation required an intact OPN-i Y166 site, because an OPN-i Y166F mutant remained mainly in the cytosol despite co-transfection with increased concentrations of p85α (FIG. 7C; FIG. 15A). These findings suggest that nuclear translocation of OPN-i is facilitated by a specific interaction with p85α and OPN-i.

Intranuclear OPN-i Interacts with Bcl6

Figure 8A:
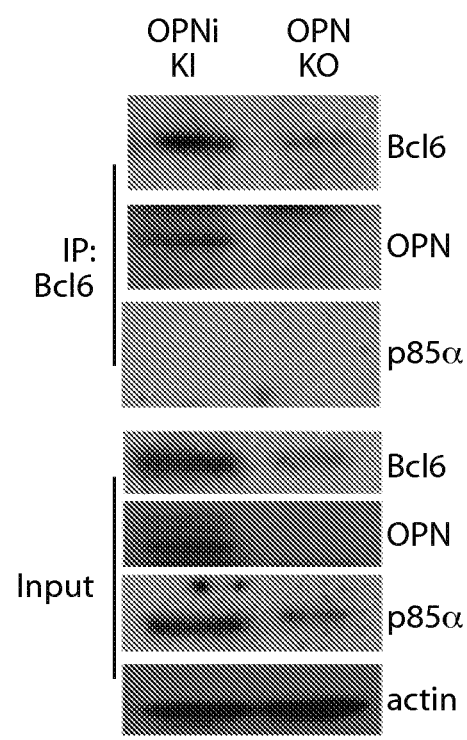
FIGS. 8A-8G show that the intranuclear interaction of Bcl6 and OPN-i protects Bcl6 from ubiquitination-mediated degradation.
Figure 8B:
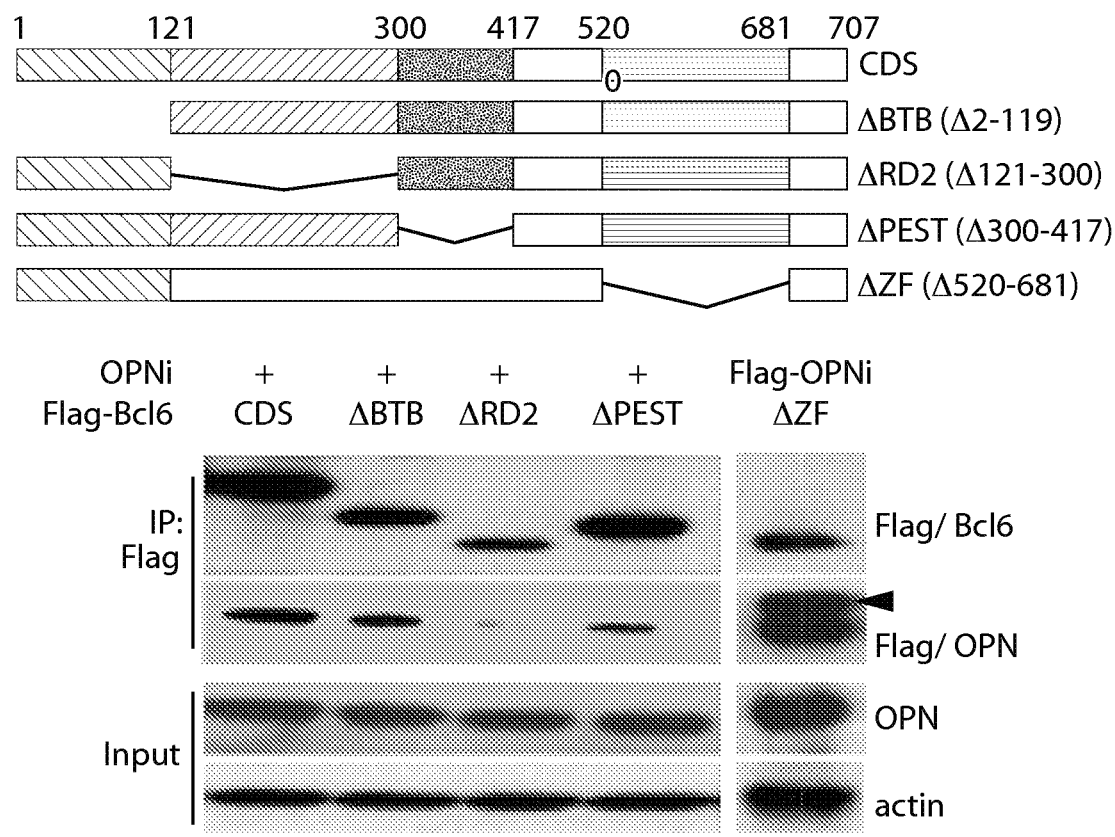

ICOS activation was associated with both increased nuclear localization of OPN-i and co-localization of intranuclear OPN-i with Bcl6 (FIG. 7A, 7B; FIG. 15A). These findings led the further characterization of a potential interaction between OPN-i and Bcl6. Bcl6-OPN-i complexes were detected after immunoprecipitation of Bcl6 protein in purified CD62L− CD4+ T cells from OPN-i KI mice 3 d post-immunization with KLH and CFA (FIG. 8A). Cellular fractionation revealed that the majority of Bcl6-OPN-i complexes were found in the nucleus (FIG. 8B), consistent with the results of confocal analysis described above (FIG. 7A, 7D; FIG. 15A). Analysis of Bcl6 deletion mutants suggested that sequences within the Bcl6 repression domain 2 (RD2), but not the BTB (for BR-C, ttk and bab), PEST or ZF (for Zinc finger) domains of Bcl6, were required for interaction between Bcl6 and OPN-i (FIG. 8B). These findings, taken together, indicate that intranuclear OPN-i may interact with Bcl6 via the Bcl6 RD2 domain (amino acids 120-300).

Intranuclear OPN-i Stabilizes Bcl6 Expression

Figure 8C:
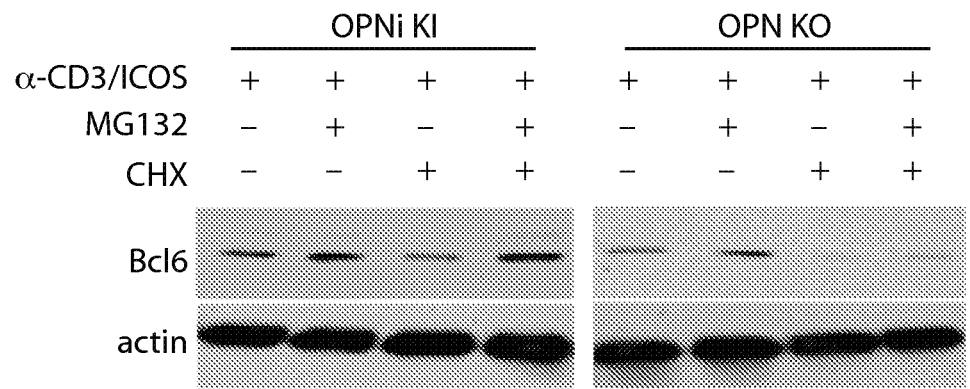
Figure 8C:
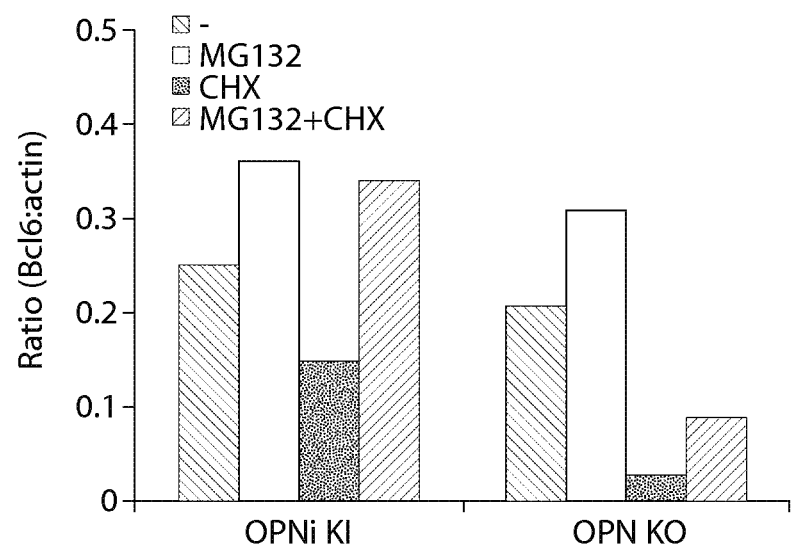
Figure 8D:
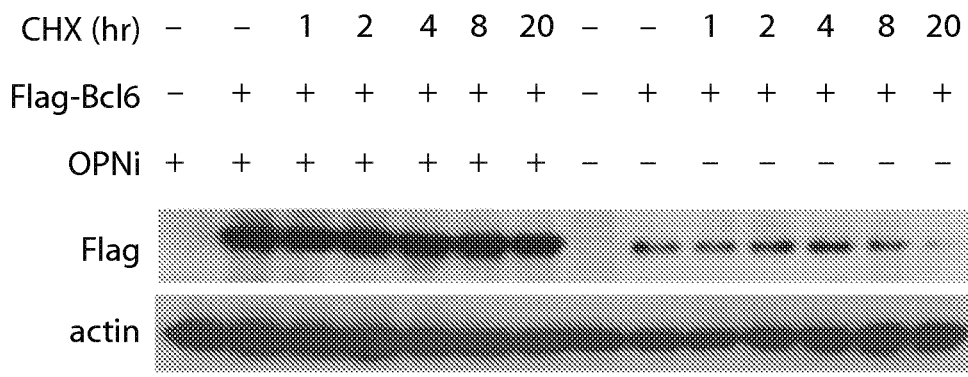
Figure 8D:
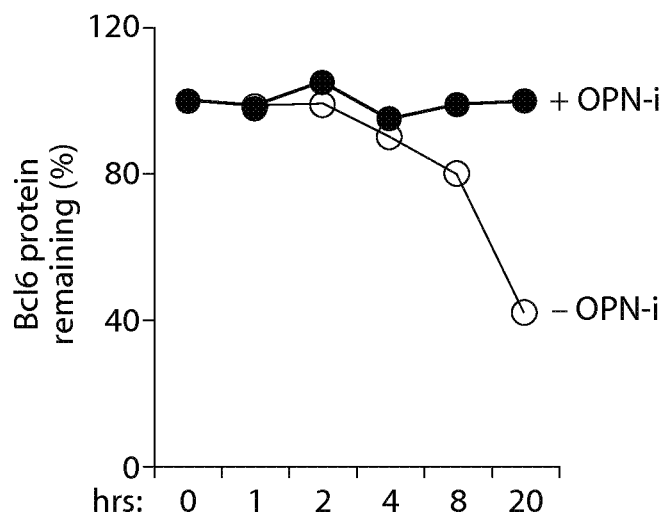
Figure 8E:
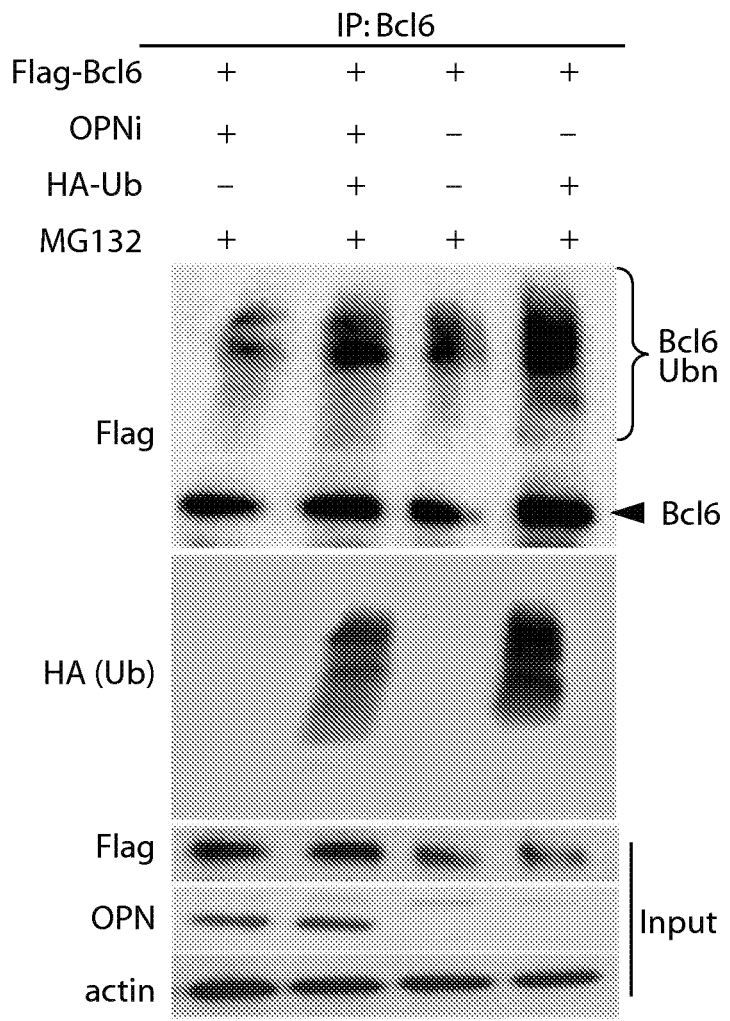
Figure 8F:
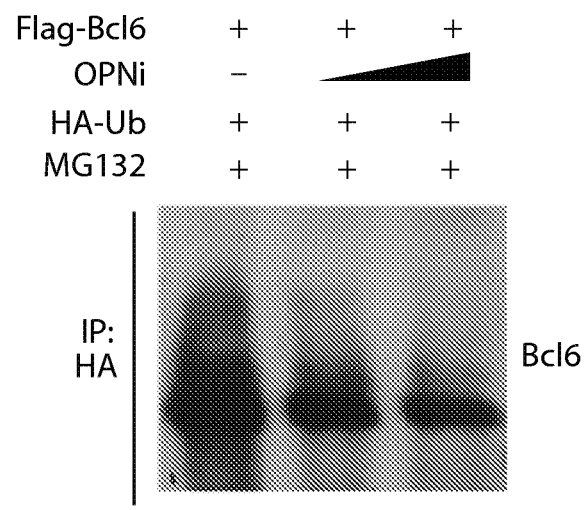
Figure 8G:
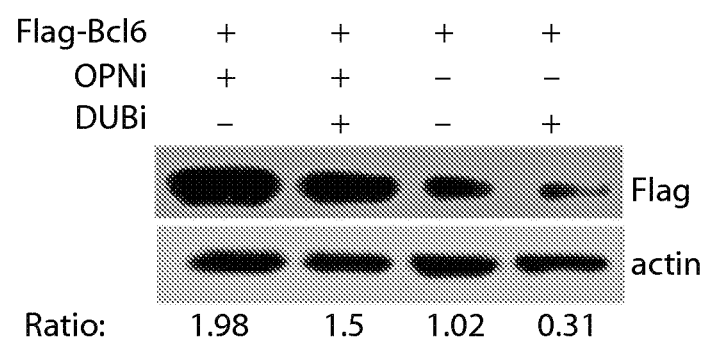
Figure 12E:
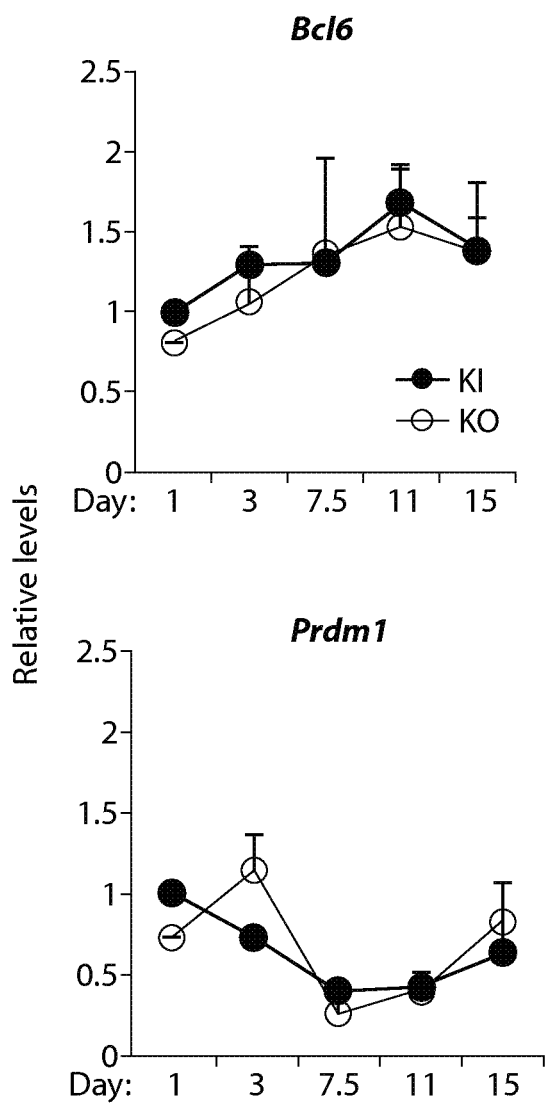
Figure 12F:
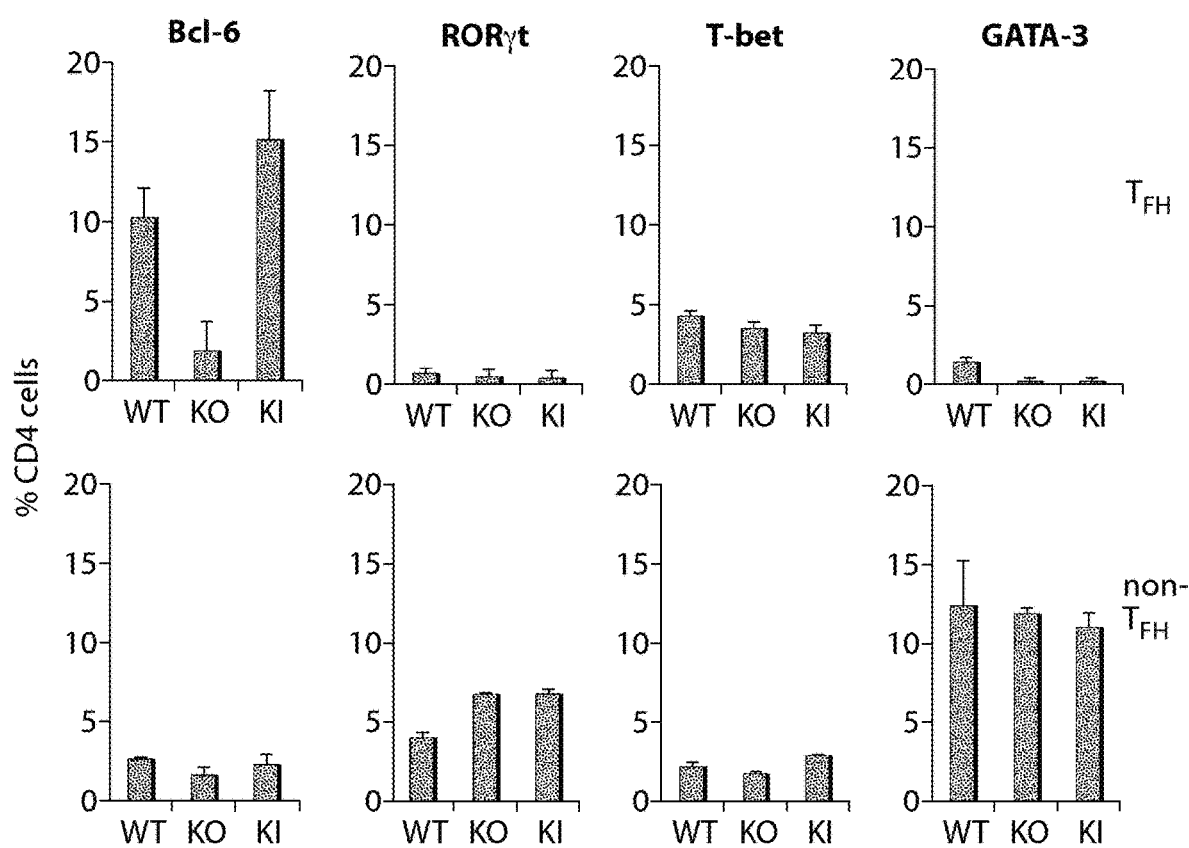

OPN-deficient CD4+ T cells express substantially reduced levels of Bcl6 protein but not mRNA at day 3-10 post-immunization (FIG. 4A, 4B; FIG. 12D, 12E), suggesting that Bcl6 protein expression might be unstable in the absence of OPN-i. Reduced Bcl6 levels were remedied by the addition of the proteasome inhibitor MG132 (FIG. 8C), suggesting Bcl6 instability was proteasome-dependent. It was therefore asked whether OPN-i might protect Bcl6 from degradation in CD4+ T cells. It was found that expression of OPN-i in CD4+ T cells substantially prevents proteasome-dependent reduction of Bcl6 protein after TCR and ICOS co-ligation (FIG. 8C) and overexpression of OPN-i prolonged the stability of Bcl6 protein in cycloheximide (CHX)-treated cells (FIG. 8D). Moreover, treatment of cells with the MG132 proteasome inhibitor to reduce degradation of ubiquitin-conjugated proteins, results in the appearance of high molecular mass species of Bcl6 in denatured extracts (FIG. 8E, 8F). These high molecular forms of Bcl6 (a) corresponded to ubiquitinated forms of Bcl6, since they were increased in the presence of overexpressed ubiquitin, and (b) were reduced by the expression of OPN-i (FIG. 8E, 8F). Protein ubiquitination can be counterbalanced by deubiquitination that inhibits protein degradation. Addition of a pan deubiquitination inhibitor (DUbi) accelerated Bcl6 degradation that was substantially remedied by co-expression of OPN-i (FIG. 8G). These findings are congruent with reports of an interaction between the Bcl6 RD2 domain and the Hsp90 chaperone enhances Bcl6 protein stability in B cell lymphomas[4, 31]. Taken together, they suggest that OPN-i stabilizes Bcl6 through interference with ubiquitin-mediated degradation of Bcl6.

The p85α-OPN-i Interaction Regulates $T_{FH}$ and $T_{FR}$ Responses In Vivo

Figure 9A:
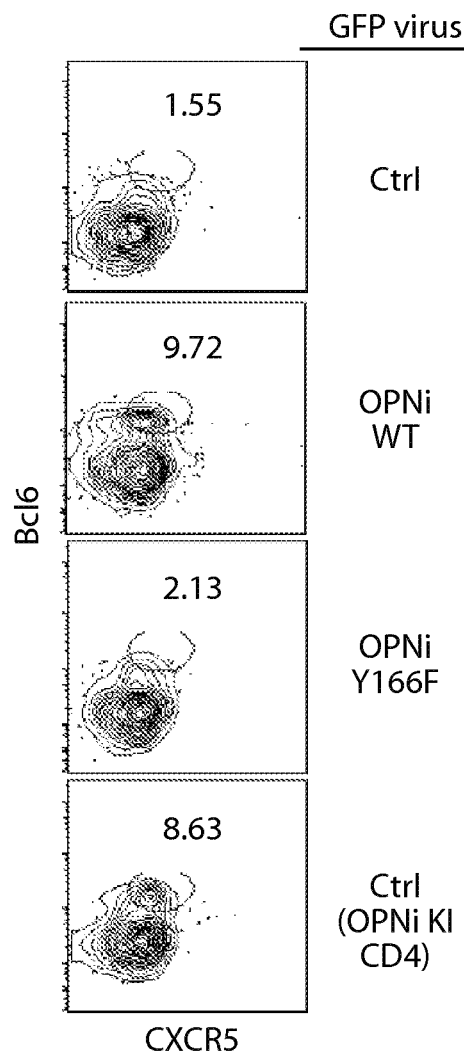
FIGS. 9A-9E show that the p85α-OPN-i interaction regulates $T_{FH}$ and $T_{FR}$ responses in vivo.
Figure 9B:
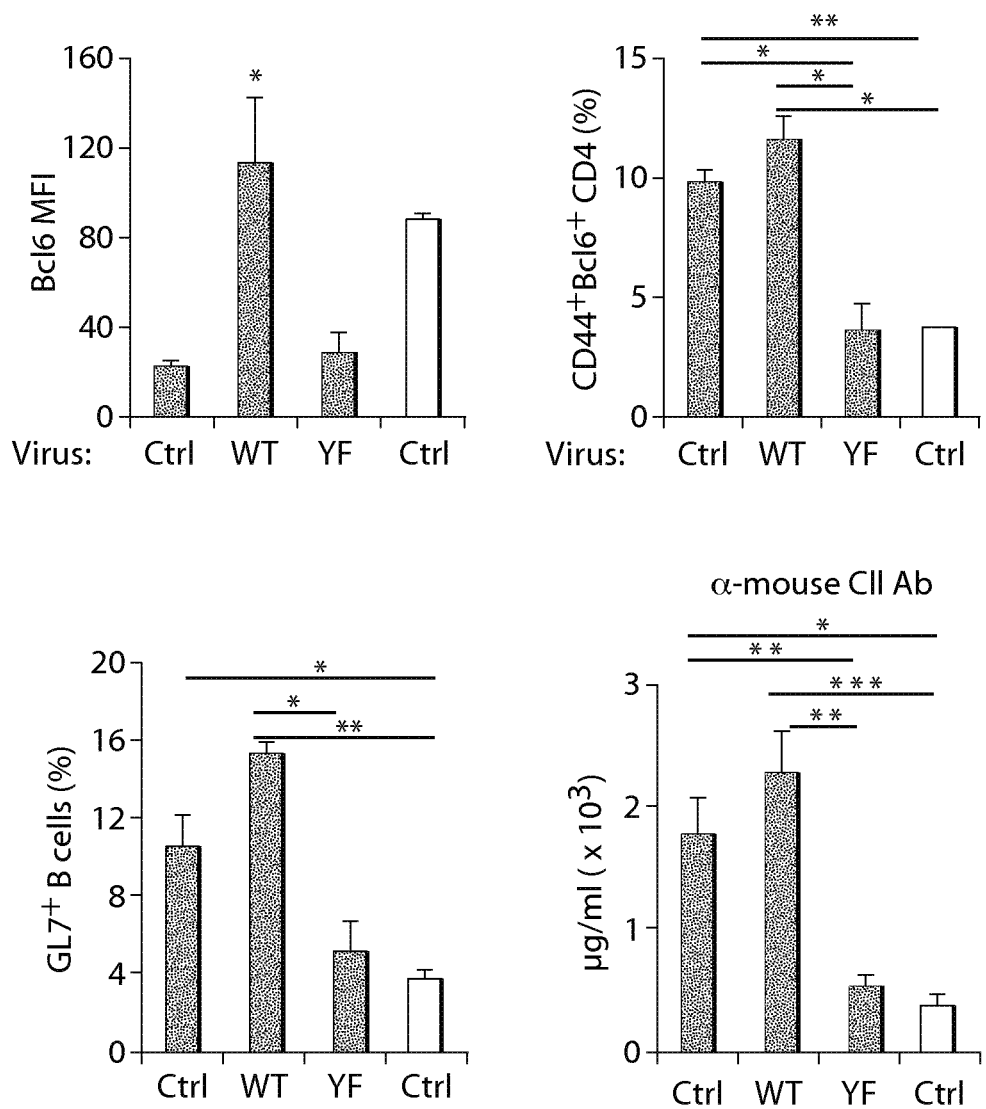
Figure 9C:
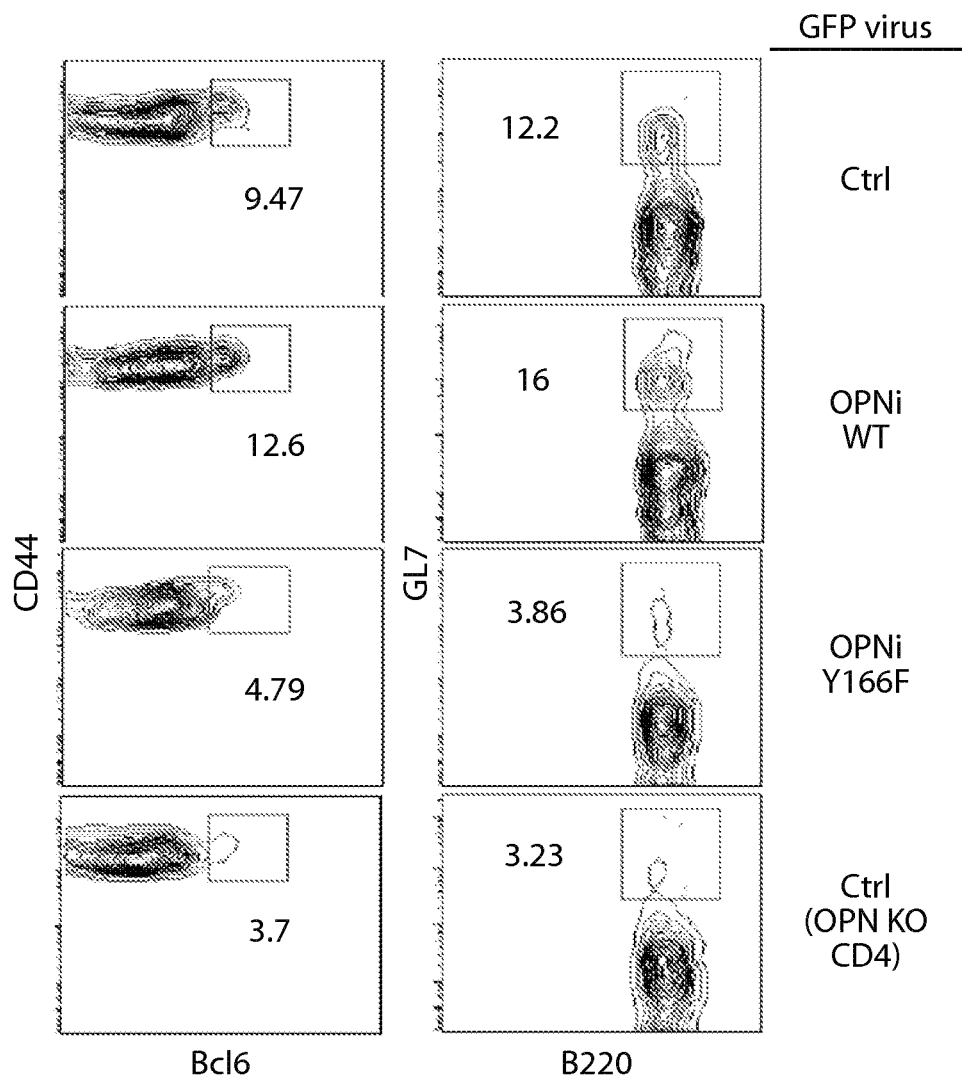
Figure 15C:
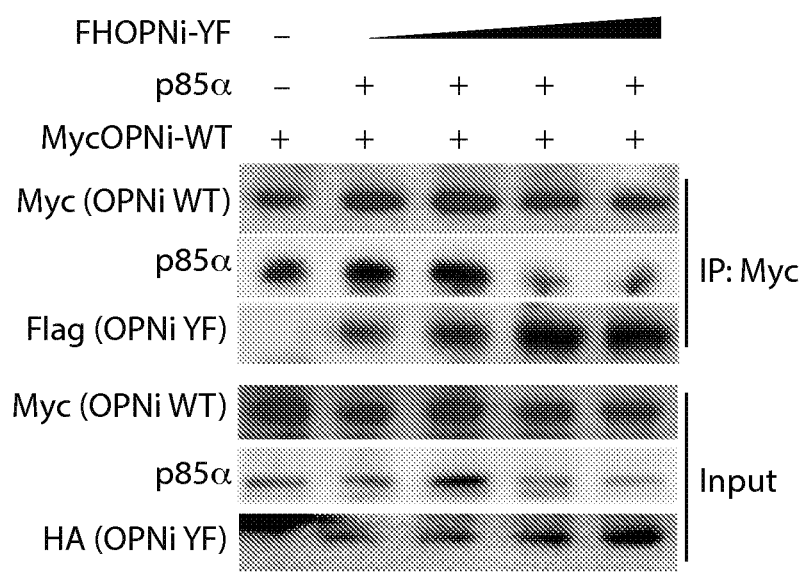

The physiological relevance was tested of the p85α-OPN-i interaction defined above using a retroviral reconstitution system (FIG. 9A). In vitro-activated OPN KO CD4+ T cells with retrovirus that expressed the OPN-i WT or mutant genes before transfer into Rag2−/−Prf1−/− hosts and LCMV infection were reconstituted. Bcl6 expression associated with $T_{FH}$ cell formation was increased substantially in CD4+ T cells reconstituted with OPN-i WT compared with CD4+ T cells expressing an OPN-i Y166F amino acid exchange mutant or control retroviral vector (FIG. 9A, 9B). Overexpression of the OPN-i Y166F mutant protein markedly reduced the interaction between OPN-i and p85α (FIG. 15C). Overexpression of OPN-i Y166F in collagen-immune CD4+ T cells decreased Bcl6+ $T_{FH}$ cell differentiation and reduced GC B cells and autoantibody response to collagen to levels that were similar to OPN KO CD4+ T cells reconstituted with control virus (FIG. 9C). In contrast, overexpression of OPN-i WT protein increased $T_{FH}$ and GC B cell formation to levels that were much higher than OPN-i KI CD4+ T cells reconstituted with control virus (FIG. 9C).

Figure 9D:
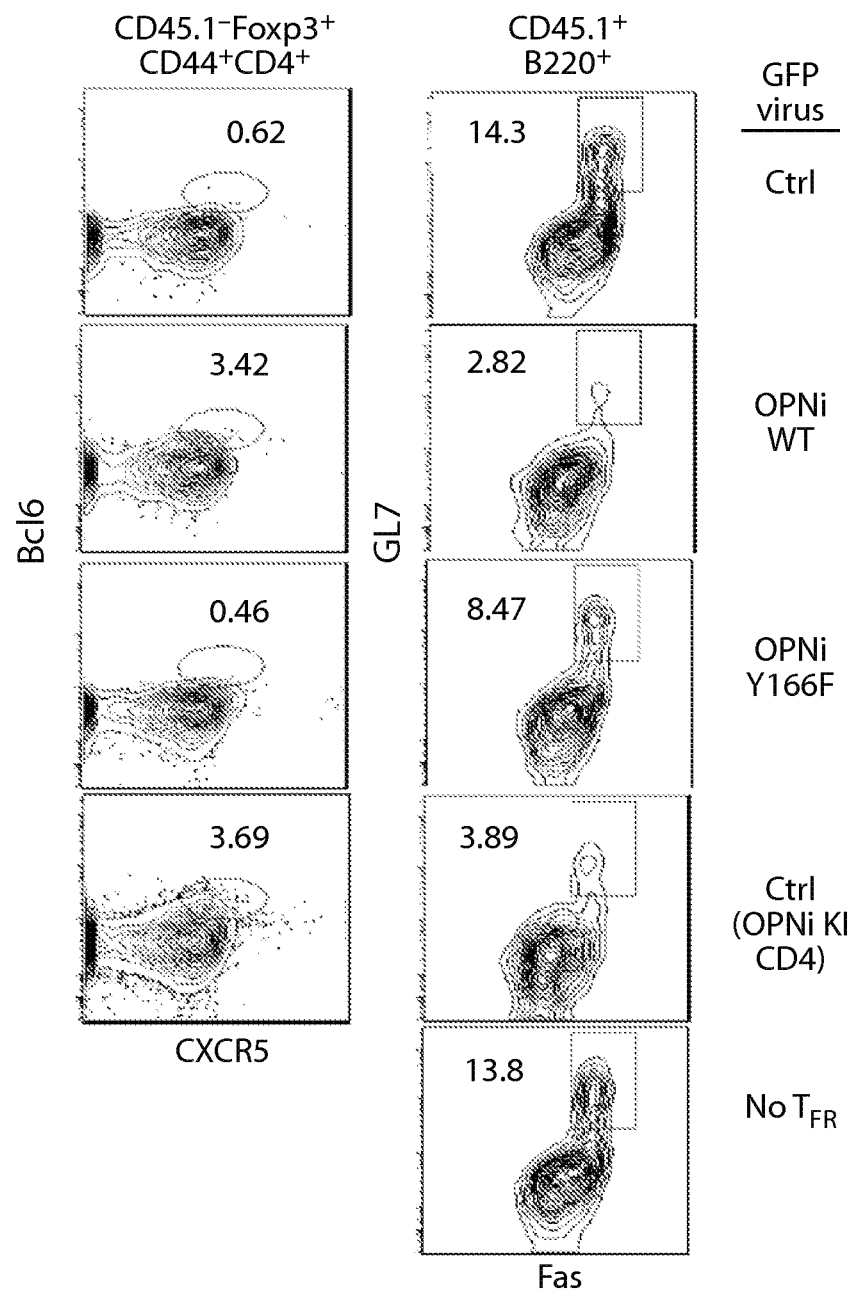
Figure 9E:
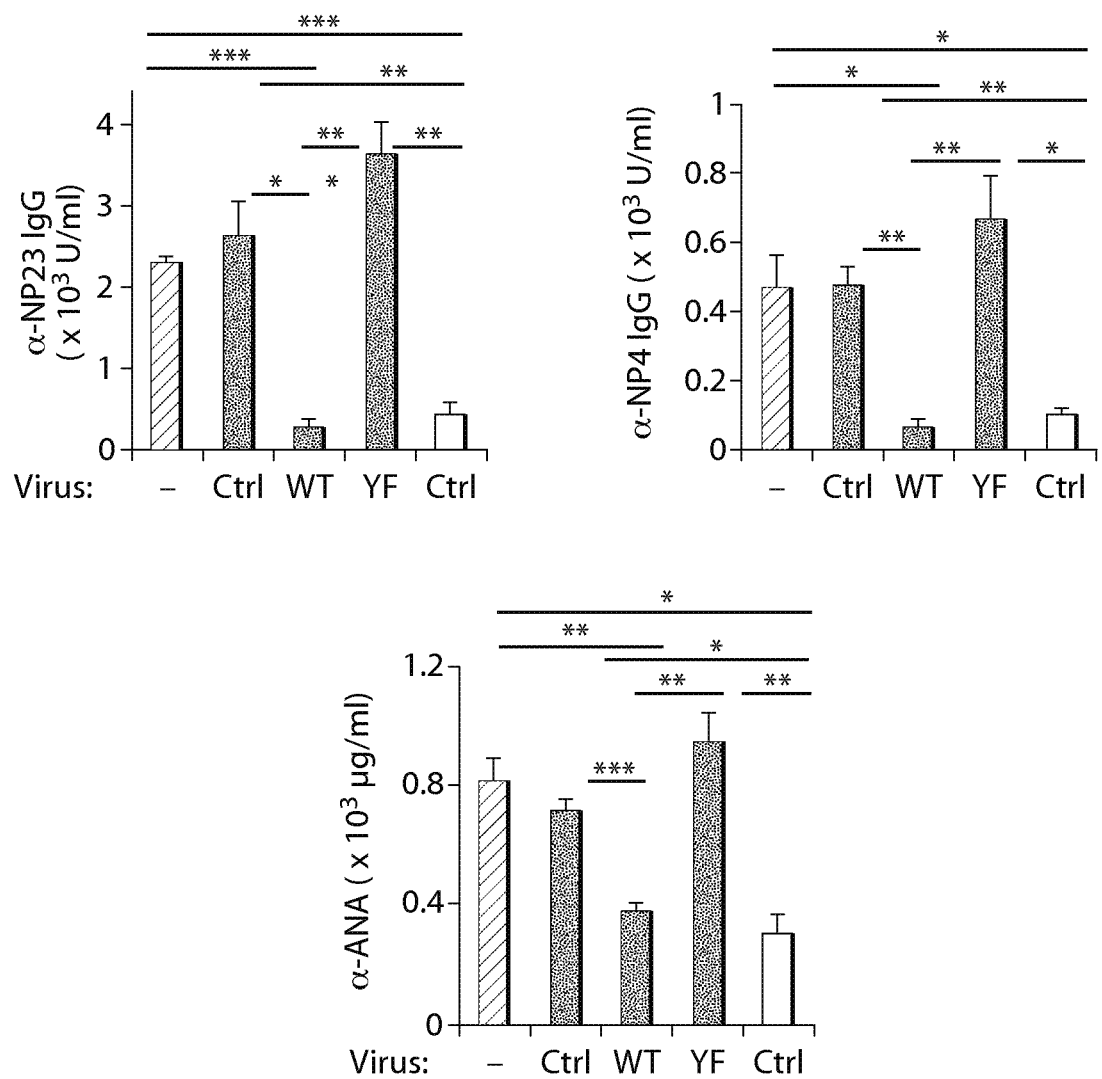

The relevance of the p85α-OPN-i interaction in functional $T_{FR}$ cell formation using a similar retroviral reconstitution system was also evaluated. OPN-i was expressed in OPN KO CD25+CD4+ T cells followed by co-transfer with CD45.1+ CD25− CD4+ effector T cells and B cells and immunization with NP-KLH in CFA (FIG. 9D). Expression of the OPN-i Y166F mutant in CD25+CD4+ T cells resulted in reduced numbers of Foxp3+Bcl6+CXCR5+ $T_{FR}$ cells to levels that were similar to OPN KO CD4+ T cells reconstituted with control virus (FIG. 9D). Decreased $T_{FR}$ cell formation was associated with a failed reduction of GC B cells and a marked increased anti-NP and anti-ANA antibody titers (FIG. 9D, 9E). Taken together, these results indicate that a specific interaction between OPN-i and p85α is essential for sustained expression of Bcl6 and functional differentiation of both $T_{FH}$ and $T_{FR}$ cells. These findings also suggest that selective targeting the p85α-OPN-i interaction in $T_{FH}$ or $T_{FR}$ cells may represent an effective therapeutic approach in modulating antibody responses in the context of systemic autoimmune disease.

Discussion

Signals from the ICOS receptor are essential for Bcl6 expression and for the initiation and maintenance of $T_{FH}$ and $T_{FR}$ cell differentiation[5, 26, 27]. Here, a molecular link that couples ICOS engagement to sustained Bcl6 expression and is essential for differentiation of both follicular CD4+ T-cell lineages that regulate the GC response is defined (FIG. 1). It is found that ICOS ligation promotes a specific interaction between the p85α component of PI3K and OPN-i that allows translocation of OPN-i to the nucleus where it protects Bcl6 from ubiquitination-dependent degradation. Although early steps resulting in enhanced Bcl6 gene expression and follicular T cell migration depend mainly on cytokines derived from activated DC[32, 33] and may be independent of OPN-i expression (FIG. 4A; FIG. 14D), sustained Bcl6 expression and full $T_{FH}$ and $T_{FR}$ cell differentiation require ICOS-dependent translocation of OPN-i and interaction with the Bcl6 TF (FIG. 1). These findings indicate that TCR-ICOS signals essential for sustained differentiation and expansion of $T_{FH}$ and $T_{FR}$ cells protect Bcl6 expression, in contrast to bystander CD4 cells that may undergo early cytokine-dependent activation by DC but fail to activate an ICOS-p85α-OPN-i pathway required for stable Bcl6 expression.

The ICOS-OPN-i Connection

ICOS activation induces two distinct but overlapping PI3K signaling pathways marked by PI3K(p110)-Akt activation on the one hand and a regulatory PI3K(p85α) component on the other. The catalytic ICOS-PI3K(p110)-Akt pathway can promote migration of $T_{FH}$ precursors into B cell follicles[11, 12], while it is shown here that the ICOS-p85α-OPN-i pathway contributes to stable Bcl6 expression and is essential for sustained follicular T cell responses. The division of labor between the two ICOS-linked PI3K pathways may depend, in part, on distinct environmental cues. MHC-II-independent G-protein coupled signals may facilitate activation of the PI3K(p110)-Akt pathway[12], while engagement of the TCR and ICOS may favor the PI3K (p85α-OPN-i pathway and sustained post-transcriptional expression of Bcl6[11, 12, 34]. The interaction between the p85α chaperone and OPN-i following ICOS-TCR ligation that results in OPN-i nuclear translocation resembles the interaction between the p85α chaperone and the XBP-1 protein resulting in nuclear localization of XBP-1 after ligation of the insulin receptor[15, 16]. Relatively low intranuclear levels of p85α (FIG. 7C) and its absence from OPN-i-Bcl6 complexes (FIG. 8A) suggest that p85α may be released before engagement of intranuclear Bcl6 by OPN-i. The ability of the multi-functional OPN-i adaptor protein to interact with other intranuclear proteins to regulate gene expression by follicular T cells deserves further study[35].

These findings also shed light on the differentiative relationship between $T_{FH}$ and $T_{FR}$ cell lineages. An appropriate balance between this follicular T-cell pair is critical for optimal GC responses to infection and avoidance of excessive or autoimmune responses that may result in host tissue destruction. Although $T_{FH}$ and $T_{FR}$ cells share many surface receptors and both require Bcl6 TF, the molecular elements responsible for differentiation of the two CD4+ T-cell lineages within GC follicles have been less clear. Here, ICOS-dependent expression of OPN-i is identified as an essential bridge to sustained Bcl6-dependent differentiation of both CD4+ subsets. The magnitude of the GC antibody response and associated B-cell selection depends on cognate $T_{FH}$ cell helper activity delivered to antigen-specific B-cells. Although OPN deficiency results in reduced $T_{FR}$ activity, defective $T_{FH}$ cell responses of OPN-deficient mice are not rescued by decreased inhibitory activity of $T_{FR}$ cells. In contrast, selective impairment of OPN-i expression by $T_{FR}$ but not $T_{FH}$ cells leads to substantially increased antibody responses, including the development of high affinity antibodies and autoantibodies (FIG. 9E). These findings indicate that OPN-dependent protection of Bcl6 expression in both follicular CD4+ T-cell subsets is essential for control of the germinal center response.

Osteopontin and the Germinal Center Response

The OPN-i and secreted OPN (OPN-s) isoforms arise from differential translation of the same mRNA[21]. Although increased expression of OPN gene has been associated with $T_{FH}$-associated autoimmune disorders and malignancies, the finding that intranuclear OPN contributes to lineage-specific T cell differentiation is unexpected. Mice that overexpress OPN develop a systemic autoimmune disorder[17] that resembles Roquin (Rc3h1) mice, which results in part from dysregulated ICOS expression[36-38]. Intracellular OPN may promote excessive expression of IFN-α by plasmacytoid dendritic cells (pDC), and contribute to Th17 cell expansion in the context of SLE[20, 24]. In support of the role of OPN in SLE pathogenesis, expression of OPN in humans with SLE and autoimmune-prone mice (MRL-lpr/lpr) correlates with disease activity[39, 40]. Although high circulating levels of OPN-s may be a useful biomarker for SLE disease activity, separate analysis of OPN-i expression by CD4+ $T_{FH}$ cells and serum OPN may provide a more accurate assessment of SLE status. The finding that disruption of the ICOS-p85α-OPN-i pathway by overexpressing OPN-i mutant inhibits $T_{FH}$ responses and associated autoantibody production also suggests that targeting the p85α-OPN-i interaction may allow inhibition of $T_{FH}$ cell responses and amelioration of systemic autoimmune disease.

Control of Bcl6 by $T_{FH}$ and $T_{FR}$ Cells

The analysis of the factors that contribute to sustained development and expansion of follicular T cells suggests a requirement for continued protection of the Bcl6 protein from ubiquitination and proteosomal degradation. Bcl6 represses a group of genes that control lymphocyte differentiation and cell division[4, 41]. The findings indicate that overexpression of OPN-i leading to enhanced levels of OPN-i-Bcl6 complexes may result in increased Bcl6 expression and enhanced $T_{FH}$ cell responses (FIG. 9C). Indeed, overexpression and nuclear localization of OPN are associated with aggressive $T_{FH}$-like lymphomas and poor prognosis[42, 43]. Studies of Bcl6 expression by normal and neoplastic GC B cells have also suggested that Bcl6 expression is highly sensitive to post-translational breakdown[4].

The interaction between the Bcl6 RD2 domain and OPN-i that inhibits ubiquitination-mediated degradation in follicular T cells may be analogous to the interaction between the Bcl6 BTB domain and Hsp90 that protects Bcl6 from proteasomal degradation in neoplastic GC B cells. Mutation of the Bcl6 BTB domain or inhibition of Hsp90 expression impairs normal and neoplastic GC B cell survival but spares $T_{FH}$ cell differentiation[4, 31, 44, 45]. Here it is shown that inhibition of OPN-i expression cripples $T_{FH}$ cell differentiation but does not affect B cell activity (FIG. 12C). Excessive Bcl6 expression may be inhibited by drugs that inhibit post-translational Bcl6 metabolism[46], including those that target the p85α-OPN-i interaction defined here. Introduction of post-translational regulation of Bcl6 may also allow lineage-specific control of follicular T cells and GC B cells through differential targeting of the OPN-i-Bcl6 and Hsp90-Bcl6 interaction, respectively.

The findings also bear on efforts to define $T_{FH}$ plasticity and diversity through lineage tracing of CD4$^+$ T cell subsets according to expression of characteristic transcription factors. Although expression of Bcl6 protein returns to basal levels by 2 weeks after immunization, Bcl6 mRNA expression remains elevated by "$T_{FH}$" cells (FIG. 4A; FIG. 12D, 12E). Precise definition of the $T_{FH}$ response, and its differentiative relationship to other $T_H$ subsets, may require coordinate measurements of Bcl6 expression at both the protein and RNA levels.

In sum, generation and analysis of OPN knock-in mice that differentially express OPN isoforms has allowed definition of an ICOS-dependent pathway that regulates Bcl6 expression at the post-translational level. The interaction between intranuclear OPN-i and Bcl6 that protects it from proteasome-associated degradation and allows sustained Bcl6 expression by $T_{FH}$ cells and $T_{FR}$ cells provides new insight into ICOS-dependent differentiation of $T_{FH}$ and $T_{FR}$ cells and suggest new therapeutic avenues to manipulate the GC response.

REFERENCES

1. Johnston, R. J. et al. Bcl6 and Blimp-1 are reciprocal and antagonistic regulators of T follicular helper cell differentiation. Science 325, 1006-1010 (2009).
2. Nurieva, R. I. et al. Bcl6 mediates the development of T follicular helper cells. Science 325, 1001-1005 (2009).
3. Yu, D. et al. The transcriptional repressor Bcl-6 directs T follicular helper cell lineage commitment. Immunity. 31, 457-468 (2009).
4. Bunting, K. L. & Melnick, A. M. New effector functions and regulatory mechanisms of BCL6 in normal and malignant lymphocytes. Curr Opin Immunol 25, 339-346 (2013).
5. Sage, P. T., Francisco, L. M., Carman, C. V. & Sharpe, A. H. The receptor PD-1 controls follicular regulatory T cells in the lymph nodes and blood. Nat Immunol 14, 152-161 (2013).
6. Linterman, M. A. et al. Foxp3(+) follicular regulatory T cells control the germinal center response. Nat. Med. 17, 975-982 (2011).
7. Chung, Y. et al. Follicular regulatory T cells expressing Foxp3 and Bcl-6 suppress germinal center reactions. Nat. Med. 17, 983-988 (2011).
8. Crotty, S. Follicular helper CD4 T cells (TFH). Annual Reviews of Immunology 29, 621-663 (2011).
9. Baumjohann, D., Okada, T. & Ansel, K. M. Cutting Edge: Distinct waves of BCL6 expression during T follicular helper cell development. J Immunol 187, 2089-2092 (2011).
10. Gigoux, M. et al. Inducible costimulator promotes helper T-cell differentiation through phosphoinositide 3-kinase. Proc Natl Acad Sci USA 106, 20371-20376 (2009).
11. Xu, H. et al. Follicular T-helper cell recruitment governed by bystander B cells and ICOS-driven motility. Nature 496, 523-527 (2013).
12. Kang, S. G. et al. MicroRNAs of the miR-17 approximately 92 family are critical regulators of TFH differentiation. Nat Immunol 14, 849-857 (2013).
13. Rolf, J., Fairfax, K. & Turner, M. Signaling pathways in T follicular helper cells. Journal of Immunology 184, 6563-6568 (2010).
14. Yu, J. et al. Regulation of the p85/p110 phosphatidylinositol 3'-kinase: stabilization and inhibition of the p110alpha catalytic subunit by the p85 regulatory subunit. Mol Cell Biol 18, 1379-1387 (1998).
15. Park, S. W. et al. The regulatory subunits of PI3K, p85alpha and p85beta, interact with XBP-1 and increase its nuclear translocation. Nat Med 16, 429-437 (2010).
16. Winnay, J. N., Boucher, J., Mori, M. A., Ueki, K. & Kahn, C. R. A regulatory subunit of phosphoinositide 3-kinase increases the nuclear accumulation of X-box-binding protein-1 to modulate the unfolded protein response. Nat Med 16, 438-445 (2010).
17. Cantor, H. & Shinohara, M. L. Regulation of T-helper-cell lineage development by osteopontin: the inside story. Nat. Rev. Immunol. 9, 137-141 (2009).
18. Ashkar, S. et al. Eta-1 (osteopontin): an early component of Type 1 (cell-mediated) immunity. Science 287, 860-864 (2000).
19. Shinohara, M. L. et al. T-bet-dependent expression of osteopontin contributes to T cell polarization. Proc Natl Acad Sci USA 102, 17101-17106 (2005).
20. Shinohara, M. L. et al. Osteopontin expression is essential for IFN-α production by plasmacytoid dendritic cells. Nat. Immunol. 7, 498-506 (2006).
21. Shinohara, M. L., Kim, H. J., Kim, J. H., Garcia, V. A. & Cantor, H. Alternative translation of Osteopontin generates intracellular and secreted isoforms that mediate distinct biological activities in dendritic cells. Proc. Natl. Acad. Sci. U.S.A. 105, 7235-7239 (2008).
22. Patarca, R., Wei, F. Y., Iregui, M. V. & Cantor, H. Differential induction of interferon-gamma gene expression after activation of CD4+ T-cells by conventional antigen and Mls superantigen. Proceedings of the National Academy of Science USA 88, 2736-2739 (1991).
23. Lampe, M. A., Patarca, R., Iregui, M. V. & Cantor, H. Polyclonal B-cell activation by the Eta-1 cytokine and the development of autoimmune disease. Journal of Immunology 147, 2902-2906 (1991).
24. Shinohara, M. L., Kim, J. H., Garcia, V. A. & Cantor, H. Engagement of the Type-I interferon receptor on dendritic cells inhibits promotion of Th17 cells: Role of intracellular Osteopontin. Immunity 29, 68-78 (2008).
25. Kerfoot, S. M. et al. Germinal center B cell and T follicular helper cell development initiates in the interfollicular zone. Immunity 34, 947-960 (2011).

26. Choi, Y. S. et al. ICOS receptor instructs T follicular helper cell versus effector cell differentiation via induction of the transcriptional repressor Bcl6. *Immunity* 34, 932-946 (2011).
27. Chang, J. H. et al. TRAF3 regulates the effector function of regulatory T cells and humoral immune responses. *J Exp Med* 211, 137-151 (2014).
28. Haxhinasto, S., Mathis, D. & Benoist, C. The AKT-mTOR axis regulates de novo differentiation of CD4+ Foxp3+ cells. *J Exp Med* 205, 565-574 (2008).
29. Obenauer, J. C., Cantley, L. C. & Yaffe, M. B. Scansite 2.0: Proteome-wide prediction of cell signaling interactions using short sequence motifs. *Nucleic Acids Res* 31, 3635-3641 (2003).
30. Yaffe, M. B. et al. A motif-based profile scanning approach for genome-wide prediction of signaling pathways. *Nat. Biotechnol.* 19, 348-353 (2001).
31. Cerchietti, L. C. et al. A purine scaffold Hsp90 inhibitor destabilizes BCL-6 and has specific antitumor activity in BCL-6-dependent B cell lymphomas. *Nat Med* 15, 1369-1376 (2009).
32. Choi, Y. S., Eto, D., Yang, J. A., Lao, C. & Crotty, S. Cutting edge: STAT1 is required for IL-6-mediated Bcl6 induction for early follicular helper cell differentiation. *J Immunol* 190, 3049-3053 (2013).
33. Nakayamada, S. et al. Type I IFN Induces Binding of STAT1 to Bcl6: Divergent Roles of STAT Family Transcription Factors in the T Follicular Helper Cell Genetic Program. *J Immunol* (2014).
34. Rolf, J. et al. Phosphoinositide 3-kinase activity in T cells regulates the magnitude of the germinal center reaction. *J Immunol* 185, 4042-4052 (2010).
35. Inoue, M. & Shinohara, M. L. Intracellular osteopontin (iOPN) and immunity. *Immunologic research* 49, 160-172 (2011).
36. Vinuesa, C. G. et al. A RING-type ubiquitin ligase family member required to repress follicular helper T cells and autoimmunity. *Nature* 435, 452-458 (2005).
37. Yu, D. et al. Roquin represses autoimmunity by limiting inducible T-cell costimulator messenger RNA. *Nature* 450, 299-303 (2007).
38. Glasmacher, E. et al. Roquin binds inducible costimulator mRNA and effectors of mRNA decay to induce microRNA-independent post-transcriptional repression. *Nat Immunol* 11, 725-733 (2010).
39. Patarca, R., Wei, F. Y., Singh, P., Morasso, M. I. & Cantor, H. Dysregulated expression of the T-cell cytokine Eta-1 in CD4-8-lymphocytes during the development of murine autoimmune disease. *Journal of Experimental Medicine* 172, 1177-1183 (1990).
40. Wong, C. K., Lit, L. C., Tam, L. S., Li, E. K. & Lam, C. W. Elevation of plasma osteopontin concentration is correlated with disease activity in patients with systemic lupus erythematosus. *Rheumatology (Oxford)* 44, 602-606 (2005).
41. Crotty, S., Johnston, R. J. & Schoenberger, S. P. Effectors and memories: Bcl-6 and Blimp-1 in T and B lymphocyte differentiation. *Nat Immunol* 11, 114-120 (2010).
42. Powell, J. A. et al. Expression profiling of a hemopoietic cell survival transcriptome implicates osteopontin as a functional prognostic factor in AML. *Blood* 114, 4859-4870 (2009).
43. Tun, H. W. et al. Pathway analysis of primary central nervous system lymphoma. *Blood* 111, 3200-3210 (2008).
44. Huang, C., Hatzi, K. & Melnick, A. Lineage-specific functions of Bcl-6 in immunity and inflammation are mediated by distinct biochemical mechanisms. *Nat Immunol* 14, 380-388 (2013).
45. Polo, J. M. et al. Specific peptide interference reveals BCL6 transcriptional and oncogenic mechanisms in B-cell lymphoma cells. *Nat Med* 10, 1329-1335 (2004).
46. Kronke, J. et al. Lenalidomide causes selective degradation of IKZF1 and IKZF3 in multiple myeloma cells. *Science* 343, 301-305 (2014).
47. Kim, H. J., Verbinnen, B., Tang, X., Lu, L. & Cantor, H. Inhibition of follicular T helper cells by CD8+ Treg is essential for self tolerance *Nature* 467, 328-332 (2010).
48. Leavenworth, J. W., Tang, X., Kim, H. J., Wang, X. & Cantor, H. Amelioration of arthritis through mobilization of peptide-specific CD8+ regulatory T cells *Journal of Clinical Investigation* 123, 1382-1389 (2013).
49. Takahashi, K., Mitsui, K. & Yamanaka, S. Role of ERas in promoting tumour-like properties in mouse embryonic stem cells. *Nature* 423, 541-545 (2003).
50. Zhao, J. J. et al. The oncogenic properties of mutant p110alpha and p110beta phosphatidylinositol 3-kinases in human mammary epithelial cells. *Proc Natl Acad Sci USA* 102, 18443-18448 (2005).
51. Lim, K. L. et al. Parkin mediates nonclassical, proteasomal-independent ubiquitination of synphilin-1: implications for Lewy body formation. *The Journal of neuroscience: the official journal of the Society for Neuroscience* 25, 2002-2009 (2005).

What is claimed is:

1. A method of promoting Bcl6-dependent follicular T cell differentiation in a subject, said method comprising
    isolating CD4+ T cells from peripheral blood from a subject in need thereof;
    transducing the isolated CD4+ T cells by contacting the CD4+ T cells with retroviral
    vectors expressing intracellular osteopontin (OPN-i);
        expanding the transduced CD4+ T cells by growing them in a culture medium until the number of transduced CD4+ T cells increases by at least 5%; and
        administering the expanded transduced CD4+ T cells to the subject, wherein, the OPN-i interacts with a p85α subunit of the phosphatidylinositol-3-OH kinase in the cytosol and with a Bcl6 RD2 domain in the nucleus of the follicular Bcl6+CD4+T cells.

2. The method of claim 1, wherein the T cell is an activated T cell.

3. The method of claim 1, wherein the T cells is modified to express a chimeric antigen receptor (CAR).

4. The method of claim 1, further comprising transducing the isolated CD4+ T cells by contacting the CD4+ T cells with retroviral vectors expressing p85α.

5. A method of promoting Bcl6-dependent follicular T cell differentiation in a subject, said method comprising
    isolating CD4+ T cells from peripheral blood from a subject in need thereof;
    treating the isolated CD4+ T cells with cell-permeable intracellular osteopontin (OPN-i) or fragments thereof fused to protein transduction domains;
        expanding the treated CD4+ T cells by growing them in a culture medium until the number of treated CD4+ T cells increases by at least 5%; and
        administering the expanded treated CD4+ T cells to the subject, wherein, the OPN-i interacts with a p85α subunit of the phosphatidylinositol-3-OH kinase in the cytosol and with a Bcl6 RD2 domain in the nucleus of the follicular Bcl6+CD4+T cells.

6. The method of claim 5, wherein the T cell is an activated T cell.

7. The method of claim 5, wherein the T cells is modified to express a chimeric antigen receptor (CAR).

8. The method of claim 5, wherein the cell-permeable OPN-i is fused to a protein transduction domain selected from the group consisting of transportan, AntHD, TAT, VP22, cationic prion protein domains and functional fragments thereof.

* * * * *

SEQUENCE LISTING

```
<160> NUMBER OF SEQ ID NOS: 8

<210> SEQ ID NO 1
<211> LENGTH: 724
<212> TYPE: PRT
<213> ORGANISM: Mus musculus

<400> SEQUENCE: 1

Met Ser Ala Glu Gly Tyr Gln Tyr Arg Ala Leu Tyr Asp Tyr Lys Lys
1               5                   10                  15

Glu Arg Glu Glu Asp Ile Asp Leu His Leu Gly Asp Ile Leu Thr Val
            20                  25                  30

Asn Lys Gly Ser Leu Val Ala Leu Gly Phe Ser Asp Gly Gln Glu Ala
        35                  40                  45

Arg Pro Glu Asp Ile Gly Trp Leu Asn Gly Tyr Asn Glu Thr Thr Gly
```

```
            50                  55                  60
Glu Arg Gly Asp Phe Pro Gly Thr Tyr Val Glu Tyr Ile Gly Arg Lys
65                  70                  75                  80

Arg Ile Ser Pro Pro Thr Pro Lys Pro Arg Pro Arg Pro Leu Pro
                85                  90                  95

Val Ala Pro Gly Ser Ser Lys Thr Glu Ala Asp Thr Glu Gln Gln Ala
                100                 105                 110

Leu Pro Leu Pro Asp Leu Ala Glu Gln Phe Ala Pro Pro Asp Val Ala
                115                 120                 125

Pro Pro Leu Leu Ile Lys Leu Leu Glu Ala Ile Glu Lys Lys Gly Leu
                130                 135                 140

Glu Cys Ser Thr Leu Tyr Arg Thr Gln Ser Ser Ser Asn Pro Ala Glu
145                 150                 155                 160

Leu Arg Gln Leu Leu Asp Cys Asp Ala Ala Ser Val Asp Leu Glu Met
                165                 170                 175

Ile Asp Val His Val Leu Ala Asp Ala Phe Lys Arg Tyr Leu Ala Asp
                180                 185                 190

Leu Pro Asn Pro Val Ile Pro Val Ala Val Tyr Asn Glu Met Met Ser
                195                 200                 205

Leu Ala Gln Glu Leu Gln Ser Pro Glu Asp Cys Ile Gln Leu Leu Lys
                210                 215                 220

Lys Leu Ile Arg Leu Pro Asn Ile Pro His Gln Cys Trp Leu Thr Leu
225                 230                 235                 240

Gln Tyr Leu Leu Lys His Phe Phe Lys Leu Ser Gln Ala Ser Ser Lys
                245                 250                 255

Asn Leu Leu Asn Ala Arg Val Leu Ser Glu Ile Phe Ser Pro Val Leu
                260                 265                 270

Phe Arg Phe Pro Ala Ala Ser Ser Asp Asn Thr Glu His Leu Ile Lys
                275                 280                 285

Ala Ile Glu Ile Leu Ile Ser Thr Glu Trp Asn Glu Arg Gln Pro Ala
                290                 295                 300

Pro Ala Leu Pro Pro Lys Pro Pro Lys Pro Thr Thr Val Ala Asn Asn
305                 310                 315                 320

Ser Met Asn Asn Asn Met Ser Leu Gln Asp Ala Glu Trp Tyr Trp Gly
                325                 330                 335

Asp Ile Ser Arg Glu Glu Val Asn Glu Lys Leu Arg Asp Thr Ala Asp
                340                 345                 350

Gly Thr Phe Leu Val Arg Asp Ala Ser Thr Lys Met His Gly Asp Tyr
                355                 360                 365

Thr Leu Thr Leu Arg Lys Gly Gly Asn Asn Lys Leu Ile Lys Ile Phe
                370                 375                 380

His Arg Asp Gly Lys Tyr Gly Phe Ser Asp Pro Leu Thr Phe Asn Ser
385                 390                 395                 400

Val Val Glu Leu Ile Asn His Tyr Arg Asn Glu Ser Leu Ala Gln Tyr
                405                 410                 415

Asn Pro Lys Leu Asp Val Lys Leu Leu Tyr Pro Val Ser Lys Tyr Gln
                420                 425                 430

Gln Asp Gln Val Val Lys Glu Asp Asn Ile Glu Ala Val Gly Lys Lys
                435                 440                 445

Leu His Glu Tyr Asn Thr Gln Phe Gln Glu Lys Ser Arg Glu Tyr Asp
                450                 455                 460

Arg Leu Tyr Glu Glu Tyr Thr Arg Thr Ser Gln Glu Ile Gln Met Lys
465                 470                 475                 480
```

```
Arg Thr Ala Ile Glu Ala Phe Asn Glu Thr Ile Lys Ile Phe Glu Glu
                485                 490                 495

Gln Cys Gln Thr Gln Glu Arg Tyr Ser Lys Glu Tyr Ile Glu Lys Phe
            500                 505                 510

Lys Arg Glu Gly Asn Glu Lys Glu Ile Gln Arg Ile Met His Asn His
        515                 520                 525

Asp Lys Leu Lys Ser Arg Ile Ser Glu Ile Ile Asp Ser Arg Arg Arg
    530                 535                 540

Leu Glu Glu Asp Leu Lys Lys Gln Ala Ala Glu Tyr Arg Glu Ile Asp
545                 550                 555                 560

Lys Arg Met Asn Ser Ile Lys Pro Asp Leu Ile Gln Leu Arg Lys Thr
                565                 570                 575

Arg Asp Gln Tyr Leu Met Trp Leu Thr Gln Lys Gly Val Arg Gln Lys
            580                 585                 590

Lys Leu Asn Glu Trp Leu Gly Asn Glu Asn Thr Glu Asp Gln Tyr Ser
        595                 600                 605

Leu Val Glu Asp Asp Glu Asp Leu Pro His His Asp Glu Lys Thr Trp
    610                 615                 620

Asn Val Gly Ser Ser Asn Arg Asn Lys Ala Glu Asn Leu Leu Arg Gly
625                 630                 635                 640

Lys Arg Asp Gly Thr Phe Leu Val Arg Glu Ser Ser Lys Gln Gly Cys
                645                 650                 655

Tyr Ala Cys Ser Val Val Val Asp Gly Glu Val Lys His Cys Val Ile
            660                 665                 670

Asn Lys Thr Ala Thr Gly Tyr Gly Phe Ala Glu Pro Tyr Asn Leu Tyr
        675                 680                 685

Ser Ser Leu Lys Glu Leu Val Leu His Tyr Gln His Thr Ser Leu Val
    690                 695                 700

Gln His Asn Asp Ser Leu Asn Val Thr Leu Ala Tyr Pro Val Tyr Ala
705                 710                 715                 720

Gln Gln Arg Arg

<210> SEQ ID NO 2
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 2

Phe Gln Val Ser Asp Glu Gln Tyr Pro Asp Ala Thr Asp Glu Asp
1               5                   10                  15

<210> SEQ ID NO 3
<211> LENGTH: 294
<212> TYPE: PRT
<213> ORGANISM: Mus musculus

<400> SEQUENCE: 3

Met Arg Leu Ala Val Ile Cys Phe Cys Leu Phe Gly Ile Ala Ser Ser
1               5                   10                  15

Leu Pro Val Lys Val Thr Asp Ser Gly Ser Ser Glu Glu Lys Leu Tyr
                20                  25                  30

Ser Leu His Pro Asp Pro Ile Ala Thr Trp Leu Val Pro Asp Pro Ser
            35                  40                  45

Gln Lys Gln Asn Leu Leu Ala Pro Gln Asn Ala Val Ser Ser Glu Glu
```

```
            50                  55                  60
Lys Asp Asp Phe Lys Gln Glu Thr Leu Pro Ser Asn Ser Asn Glu Ser
 65                  70                  75                  80

His Asp His Met Asp Asp Asp Asp Asp Asp Asp Asp Gly Asp
                 85                  90                  95

His Ala Glu Ser Glu Asp Ser Val Asp Ser Asp Ser Asp Glu Ser
                100                 105                 110

His His Ser Asp Glu Ser Asp Glu Thr Val Thr Ala Ser Thr Gln Ala
                115                 120                 125

Asp Thr Phe Thr Pro Ile Val Pro Thr Val Asp Val Pro Asn Gly Arg
            130                 135                 140

Gly Asp Ser Leu Ala Tyr Gly Leu Arg Ser Lys Ser Arg Ser Phe Gln
145                 150                 155                 160

Val Ser Asp Glu Gln Tyr Pro Asp Ala Thr Asp Glu Asp Leu Thr Ser
                165                 170                 175

His Met Lys Ser Gly Glu Ser Lys Glu Ser Leu Asp Val Ile Pro Val
                180                 185                 190

Ala Gln Leu Leu Ser Met Pro Ser Asp Gln Asp Asn Asn Gly Lys Gly
            195                 200                 205

Ser His Glu Ser Ser Gln Leu Asp Glu Pro Ser Leu Glu Thr His Arg
            210                 215                 220

Leu Glu His Ser Lys Glu Ser Gln Glu Ser Ala Asp Gln Ser Asp Val
225                 230                 235                 240

Ile Asp Ser Gln Ala Ser Ser Lys Ala Ser Leu Glu His Gln Ser His
                245                 250                 255

Lys Phe His Ser His Lys Asp Lys Leu Val Leu Asp Pro Lys Ser Lys
                260                 265                 270

Glu Asp Asp Arg Tyr Leu Lys Phe Arg Ile Ser His Glu Leu Glu Ser
            275                 280                 285

Ser Ser Ser Glu Val Asn
        290

<210> SEQ ID NO 4
<211> LENGTH: 707
<212> TYPE: PRT
<213> ORGANISM: Mus musculus

<400> SEQUENCE: 4

Met Ala Ser Pro Ala Asp Ser Cys Ile Gln Phe Thr Arg His Ala Ser
 1               5                  10                  15

Asp Val Leu Leu Asn Leu Asn Arg Leu Arg Ser Arg Asp Ile Leu Thr
                20                  25                  30

Asp Val Val Ile Val Val Ser Arg Glu Gln Phe Arg Ala His Lys Thr
             35                  40                  45

Val Leu Met Ala Cys Ser Gly Leu Phe Tyr Ser Ile Phe Thr Asp Gln
         50                  55                  60

Leu Lys Cys Asn Leu Ser Val Ile Asn Leu Asp Pro Glu Ile Ser Pro
 65                  70                  75                  80

Glu Gly Phe Cys Ile Leu Leu Asp Phe Met Tyr Thr Ser Arg Leu Asn
                 85                  90                  95

Leu Arg Glu Gly Asn Ile Met Ala Val Met Thr Thr Ala Met Tyr Leu
                100                 105                 110

Gln Met Glu His Val Val Asp Thr Cys Arg Lys Phe Ile Lys Ala Ser
                115                 120                 125
```

```
Glu Ala Glu Met Ala Pro Ala Leu Lys Pro Pro Arg Glu Glu Phe Leu
    130                 135                 140

Asn Ser Arg Met Leu Met Pro His Asp Ile Met Ala Tyr Arg Gly Arg
145                 150                 155                 160

Glu Val Val Glu Asn Asn Met Pro Leu Arg Asn Thr Pro Gly Cys Glu
                165                 170                 175

Ser Arg Ala Phe Ala Pro Pro Leu Tyr Ser Gly Leu Ser Thr Pro Pro
            180                 185                 190

Ala Ser Tyr Pro Met Tyr Ser His Leu Pro Leu Ser Thr Phe Leu Phe
            195                 200                 205

Ser Asp Glu Glu Leu Arg Asp Ala Pro Arg Met Pro Val Ala Asn Pro
210                 215                 220

Phe Pro Lys Glu Arg Ala Leu Pro Cys Asp Ser Ala Arg Gln Val Pro
225                 230                 235                 240

Asn Glu Tyr Ser Arg Pro Ala Met Glu Val Ser Pro Ser Leu Cys His
                245                 250                 255

Ser Asn Ile Tyr Ser Pro Lys Glu Ala Val Pro Glu Glu Ala Arg Ser
            260                 265                 270

Asp Ile His Tyr Ser Val Pro Glu Gly Pro Lys Pro Ala Val Pro Ser
        275                 280                 285

Ala Arg Asn Ala Pro Tyr Phe Pro Cys Asp Lys Ala Ser Lys Glu Glu
    290                 295                 300

Glu Arg Pro Ser Ser Glu Asp Glu Ile Ala Leu His Phe Glu Pro Pro
305                 310                 315                 320

Asn Ala Pro Leu Asn Arg Lys Gly Leu Val Ser Pro Gln Ser Pro Gln
                325                 330                 335

Lys Ser Asp Cys Gln Pro Asn Ser Pro Thr Glu Ser Cys Ser Ser Lys
            340                 345                 350

Asn Ala Cys Ile Leu Gln Ala Ser Gly Ser Pro Pro Ala Lys Ser Pro
        355                 360                 365

Thr Asp Pro Lys Ala Cys Asn Trp Lys Lys Tyr Lys Phe Ile Val Leu
    370                 375                 380

Asn Ser Leu Asn Gln Asn Ala Lys Pro Glu Gly Ser Glu Gln Ala Glu
385                 390                 395                 400

Leu Gly Arg Leu Ser Pro Arg Ala Tyr Pro Ala Pro Pro Ala Cys Gln
                405                 410                 415

Pro Pro Met Glu Pro Ala Asn Leu Asp Leu Gln Ser Pro Thr Lys Leu
            420                 425                 430

Ser Ala Ser Gly Glu Asp Ser Thr Ile Pro Gln Ala Ser Arg Leu Asn
        435                 440                 445

Asn Leu Val Asn Arg Ser Leu Ala Gly Ser Pro Arg Ser Ser Ser Glu
450                 455                 460

Ser His Ser Pro Leu Tyr Met His Pro Pro Lys Cys Thr Ser Cys Gly
465                 470                 475                 480

Ser Gln Ser Pro Gln His Thr Glu Met Cys Leu His Thr Ala Gly Pro
                485                 490                 495

Thr Phe Pro Glu Glu Met Gly Glu Thr Gln Ser Glu Tyr Ser Asp Ser
            500                 505                 510

Ser Cys Glu Asn Gly Thr Phe Phe Cys Asn Glu Cys Asp Cys Arg Phe
        515                 520                 525

Ser Glu Glu Ala Ser Leu Lys Arg His Thr Leu Gln Thr His Ser Asp
530                 535                 540

Lys Pro Tyr Lys Cys Asp Arg Cys Gln Ala Ser Phe Arg Tyr Lys Gly
```

```
                           545                 550                 555                 560
            Asn Leu Ala Ser His Lys Thr Val His Thr Gly Glu Lys Pro Tyr Arg
                            565                 570                 575

Cys Asn Ile Cys Gly Ala Gln Phe Asn Arg Pro Ala Asn Leu Lys Thr
                            580                 585                 590

His Thr Arg Ile His Ser Gly Glu Lys Pro Tyr Lys Cys Glu Thr Cys
                            595                 600                 605

Gly Ala Arg Phe Val Gln Val Ala His Leu Arg Ala His Val Leu Ile
                            610                 615                 620

His Thr Gly Glu Lys Pro Tyr Pro Cys Glu Ile Cys Gly Thr Arg Phe
            625                 630                 635                 640

Arg His Leu Gln Thr Leu Lys Ser His Leu Arg Ile His Thr Gly Glu
                            645                 650                 655

Lys Pro Tyr His Cys Glu Lys Cys Asn Leu His Phe Arg His Lys Ser
                            660                 665                 670

Gln Leu Arg Leu His Leu Arg Gln Lys His Gly Ala Ile Thr Asn Thr
                            675                 680                 685

Lys Val Gln Tyr Arg Val Ser Ala Ala Asp Leu Pro Pro Glu Leu Pro
                            690                 695                 700

Lys Ala Cys
            705

<210> SEQ ID NO 5
            <211> LENGTH: 300
            <212> TYPE: PRT
            <213> ORGANISM: Homo sapiens

<400> SEQUENCE: 5

Met Arg Ile Ala Val Ile Cys Phe Cys Leu Leu Gly Ile Thr Cys Ala
            1               5                   10                  15

Ile Pro Val Lys Gln Ala Asp Ser Gly Ser Ser Glu Glu Lys Gln Leu
                            20                  25                  30

Tyr Asn Lys Tyr Pro Asp Ala Val Ala Thr Trp Leu Asn Pro Asp Pro
                            35                  40                  45

Ser Gln Lys Gln Asn Leu Leu Ala Pro Gln Thr Leu Pro Ser Lys Ser
                            50                  55                  60

Asn Glu Ser His Asp His Met Asp Asp Met Asp Asp Glu Asp Asp Asp
            65                  70                  75                  80

Asp His Val Asp Ser Gln Asp Ser Ile Asp Ser Asn Asp Ser Asp Asp
                            85                  90                  95

Val Asp Asp Thr Asp Asp Ser His Gln Ser Asp Glu Ser His His Ser
                            100                 105                 110

Asp Glu Ser Asp Glu Leu Val Thr Asp Phe Pro Thr Asp Leu Pro Ala
                            115                 120                 125

Thr Glu Val Phe Thr Pro Val Val Pro Thr Val Asp Thr Tyr Asp Gly
                            130                 135                 140

Arg Gly Asp Ser Val Val Tyr Gly Leu Arg Ser Lys Ser Lys Lys Phe
            145                 150                 155                 160

Arg Arg Pro Asp Ile Gln Tyr Pro Asp Ala Thr Asp Glu Asp Ile Thr
                            165                 170                 175

Ser His Met Glu Ser Glu Glu Leu Asn Gly Ala Tyr Lys Ala Ile Pro
                            180                 185                 190

Val Ala Gln Asp Leu Asn Ala Pro Ser Asp Trp Asp Ser Arg Gly Lys
                            195                 200                 205
```

```
Asp Ser Tyr Glu Thr Ser Gln Leu Asp Asp Gln Ser Ala Glu Thr His
    210                 215                 220
Ser His Lys Gln Ser Arg Leu Tyr Lys Arg Lys Ala Asn Asp Glu Ser
225                 230                 235                 240
Asn Glu His Ser Asp Val Ile Asp Ser Gln Glu Leu Ser Lys Val Ser
                245                 250                 255
Arg Glu Phe His Ser His Glu Phe His Ser His Glu Asp Met Leu Val
            260                 265                 270
Val Asp Pro Lys Ser Lys Glu Asp Lys His Leu Lys Phe Arg Ile
        275                 280                 285
Ser His Glu Leu Asp Ser Ala Ser Ser Glu Val Asn
    290                 295                 300

<210> SEQ ID NO 6
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 6

Phe Arg Arg Pro Asp Ile Gln Tyr Pro Asp Ala Thr Asp Glu Asp
1               5                   10                  15

<210> SEQ ID NO 7
<211> LENGTH: 724
<212> TYPE: PRT
<213> ORGANISM: Homo sapiens

<400> SEQUENCE: 7

Met Ser Ala Glu Gly Tyr Gln Tyr Arg Ala Leu Tyr Asp Tyr Lys Lys
1               5                   10                  15
Glu Arg Glu Glu Asp Ile Asp Leu His Leu Gly Asp Ile Leu Thr Val
                20                  25                  30
Asn Lys Gly Ser Leu Val Ala Leu Gly Phe Ser Asp Gly Gln Glu Ala
            35                  40                  45
Arg Pro Glu Glu Ile Gly Trp Leu Asn Gly Tyr Asn Glu Thr Thr Gly
        50                  55                  60
Glu Arg Gly Asp Phe Pro Gly Thr Tyr Val Glu Tyr Ile Gly Arg Lys
65                  70                  75                  80
Lys Ile Ser Pro Pro Thr Pro Lys Pro Arg Pro Pro Arg Pro Leu Pro
                85                  90                  95
Val Ala Pro Gly Ser Ser Lys Thr Glu Ala Asp Val Glu Gln Gln Ala
            100                 105                 110
Leu Thr Leu Pro Asp Leu Ala Glu Gln Phe Ala Pro Pro Asp Ile Ala
        115                 120                 125
Pro Pro Leu Leu Ile Lys Leu Val Glu Ala Ile Glu Lys Lys Gly Leu
130                 135                 140
Glu Cys Ser Thr Leu Tyr Arg Thr Gln Ser Ser Ser Asn Leu Ala Glu
145                 150                 155                 160
Leu Arg Gln Leu Leu Asp Cys Asp Thr Pro Ser Val Asp Leu Glu Met
                165                 170                 175
Ile Asp Val His Val Leu Ala Asp Ala Phe Lys Arg Tyr Leu Leu Asp
            180                 185                 190
Leu Pro Asn Pro Val Ile Pro Ala Ala Val Tyr Ser Glu Met Ile Ser
        195                 200                 205
Leu Ala Pro Glu Val Gln Ser Ser Glu Glu Tyr Ile Gln Leu Leu Lys
```

```
            210                 215                 220
Lys Leu Ile Arg Ser Pro Ser Ile Pro His Gln Tyr Trp Leu Thr Leu
225                 230                 235                 240

Gln Tyr Leu Leu Lys His Phe Phe Lys Leu Ser Gln Thr Ser Ser Lys
                245                 250                 255

Asn Leu Leu Asn Ala Arg Val Leu Ser Glu Ile Phe Ser Pro Met Leu
                260                 265                 270

Phe Arg Phe Ser Ala Ala Ser Ser Asp Asn Thr Glu Asn Leu Ile Lys
            275                 280                 285

Val Ile Glu Ile Leu Ile Ser Thr Glu Trp Asn Glu Arg Gln Pro Ala
        290                 295                 300

Pro Ala Leu Pro Pro Lys Pro Pro Lys Pro Thr Thr Val Ala Asn Asn
305                 310                 315                 320

Gly Met Asn Asn Asn Met Ser Leu Gln Asp Ala Glu Trp Tyr Trp Gly
                325                 330                 335

Asp Ile Ser Arg Glu Glu Val Asn Glu Lys Leu Arg Asp Thr Ala Asp
                340                 345                 350

Gly Thr Phe Leu Val Arg Asp Ala Ser Thr Lys Met His Gly Asp Tyr
            355                 360                 365

Thr Leu Thr Leu Arg Lys Gly Gly Asn Asn Lys Leu Ile Lys Ile Phe
370                 375                 380

His Arg Asp Gly Lys Tyr Gly Phe Ser Asp Pro Leu Thr Phe Ser Ser
385                 390                 395                 400

Val Val Glu Leu Ile Asn His Tyr Arg Asn Glu Ser Leu Ala Gln Tyr
                405                 410                 415

Asn Pro Lys Leu Asp Val Lys Leu Leu Tyr Pro Val Ser Lys Tyr Gln
            420                 425                 430

Gln Asp Gln Val Val Lys Glu Asp Asn Ile Glu Ala Val Gly Lys Lys
        435                 440                 445

Leu His Glu Tyr Asn Thr Gln Phe Gln Glu Lys Ser Arg Glu Tyr Asp
450                 455                 460

Arg Leu Tyr Glu Glu Tyr Thr Arg Thr Ser Gln Glu Ile Gln Met Lys
465                 470                 475                 480

Arg Thr Ala Ile Glu Ala Phe Asn Glu Thr Ile Lys Ile Phe Glu Glu
                485                 490                 495

Gln Cys Gln Thr Gln Glu Arg Tyr Ser Lys Glu Tyr Ile Glu Lys Phe
            500                 505                 510

Lys Arg Glu Gly Asn Glu Lys Glu Ile Gln Arg Ile Met His Asn Tyr
        515                 520                 525

Asp Lys Leu Lys Ser Arg Ile Ser Glu Ile Ile Asp Ser Arg Arg Arg
530                 535                 540

Leu Glu Glu Asp Leu Lys Lys Gln Ala Ala Tyr Arg Glu Ile Asp
545                 550                 555                 560

Lys Arg Met Asn Ser Ile Lys Pro Asp Leu Ile Gln Leu Arg Lys Thr
                565                 570                 575

Arg Asp Gln Tyr Leu Met Trp Leu Thr Gln Lys Gly Val Arg Gln Lys
            580                 585                 590

Lys Leu Asn Glu Trp Leu Gly Asn Glu Asn Thr Glu Asp Gln Tyr Ser
        595                 600                 605

Leu Val Glu Asp Asp Glu Asp Leu Pro His His Asp Glu Lys Thr Trp
610                 615                 620

Asn Val Gly Ser Ser Asn Arg Asn Lys Ala Glu Asn Leu Leu Arg Gly
625                 630                 635                 640
```

```
Lys Arg Asp Gly Thr Phe Leu Val Arg Glu Ser Ser Lys Gln Gly Cys
                645                 650                 655

Tyr Ala Cys Ser Val Val Asp Gly Glu Val Lys His Cys Val Ile
            660                 665                 670

Asn Lys Thr Ala Thr Gly Tyr Gly Phe Ala Glu Pro Tyr Asn Leu Tyr
            675                 680                 685

Ser Ser Leu Lys Glu Leu Val Leu His Tyr Gln His Thr Ser Leu Val
            690                 695                 700

Gln His Asn Asp Ser Leu Asn Val Thr Leu Ala Tyr Pro Val Tyr Ala
705                 710                 715                 720

Gln Gln Arg Arg

<210> SEQ ID NO 8
<211> LENGTH: 706
<212> TYPE: PRT
<213> ORGANISM: Homo sapiens

<400> SEQUENCE: 8

Met Ala Ser Pro Ala Asp Ser Cys Ile Gln Phe Thr Arg His Ala Ser
1               5                   10                  15

Asp Val Leu Leu Asn Leu Asn Arg Leu Arg Ser Arg Asp Ile Leu Thr
            20                  25                  30

Asp Val Val Ile Val Val Ser Arg Glu Gln Phe Arg Ala His Lys Thr
        35                  40                  45

Val Leu Met Ala Cys Ser Gly Leu Phe Tyr Ser Ile Phe Thr Asp Gln
    50                  55                  60

Leu Lys Cys Asn Leu Ser Val Ile Asn Leu Asp Pro Glu Ile Asn Pro
65                  70                  75                  80

Glu Gly Phe Cys Ile Leu Leu Asp Phe Met Tyr Thr Ser Arg Leu Asn
                85                  90                  95

Leu Arg Glu Gly Asn Ile Met Ala Val Met Ala Thr Ala Met Tyr Leu
            100                 105                 110

Gln Met Glu His Val Val Asp Thr Cys Arg Lys Phe Ile Lys Ala Ser
        115                 120                 125

Glu Ala Glu Met Val Ser Ala Ile Lys Pro Pro Arg Glu Glu Phe Leu
    130                 135                 140

Asn Ser Arg Met Leu Met Pro Gln Asp Ile Met Ala Tyr Arg Gly Arg
145                 150                 155                 160

Glu Val Val Glu Asn Asn Leu Pro Leu Arg Ser Ala Pro Gly Cys Glu
                165                 170                 175

Ser Arg Ala Phe Ala Pro Ser Leu Tyr Ser Gly Leu Ser Thr Pro Pro
            180                 185                 190

Ala Ser Tyr Ser Met Tyr Ser His Leu Pro Val Ser Ser Leu Leu Phe
        195                 200                 205

Ser Asp Glu Glu Phe Arg Asp Val Arg Met Pro Val Ala Asn Pro Phe
    210                 215                 220

Pro Lys Glu Arg Ala Leu Pro Cys Asp Ser Ala Arg Pro Val Pro Gly
225                 230                 235                 240

Glu Tyr Ser Arg Pro Thr Leu Glu Val Ser Pro Asn Val Cys His Ser
                245                 250                 255

Asn Ile Tyr Ser Pro Lys Glu Thr Ile Pro Glu Glu Ala Arg Ser Asp
            260                 265                 270

Met His Tyr Ser Val Ala Glu Gly Leu Lys Pro Ala Ala Pro Ser Ala
        275                 280                 285
```

```
Arg Asn Ala Pro Tyr Phe Pro Cys Asp Lys Ala Ser Lys Glu Glu Glu
    290             295                 300

Arg Pro Ser Ser Glu Asp Glu Ile Ala Leu His Phe Glu Pro Pro Asn
305             310                 315                 320

Ala Pro Leu Asn Arg Lys Gly Leu Val Ser Pro Gln Ser Pro Gln Lys
                325                 330                 335

Ser Asp Cys Gln Pro Asn Ser Pro Thr Glu Ser Cys Ser Ser Lys Asn
                340                 345                 350

Ala Cys Ile Leu Gln Ala Ser Gly Ser Pro Pro Ala Lys Ser Pro Thr
            355                 360                 365

Asp Pro Lys Ala Cys Asn Trp Lys Lys Tyr Lys Phe Ile Val Leu Asn
370                 375                 380

Ser Leu Asn Gln Asn Ala Lys Pro Glu Gly Pro Glu Gln Ala Glu Leu
385                 390                 395                 400

Gly Arg Leu Ser Pro Arg Ala Tyr Thr Ala Pro Pro Ala Cys Gln Pro
                405                 410                 415

Pro Met Glu Pro Glu Asn Leu Asp Leu Gln Ser Pro Thr Lys Leu Ser
            420                 425                 430

Ala Ser Gly Glu Asp Ser Thr Ile Pro Gln Ala Ser Arg Leu Asn Asn
            435                 440                 445

Ile Val Asn Arg Ser Met Thr Gly Ser Pro Arg Ser Ser Ser Glu Ser
            450                 455                 460

His Ser Pro Leu Tyr Met His Pro Pro Lys Cys Thr Ser Cys Gly Ser
465                 470                 475                 480

Gln Ser Pro Gln His Ala Glu Met Cys Leu His Thr Ala Gly Pro Thr
                485                 490                 495

Phe Pro Glu Glu Met Gly Glu Thr Gln Ser Glu Tyr Ser Asp Ser Ser
            500                 505                 510

Cys Glu Asn Gly Ala Phe Phe Cys Asn Glu Cys Asp Cys Arg Phe Ser
            515                 520                 525

Glu Glu Ala Ser Leu Lys Arg His Thr Leu Gln Thr His Ser Asp Lys
530                 535                 540

Pro Tyr Lys Cys Asp Arg Cys Gln Ala Ser Phe Arg Tyr Lys Gly Asn
545                 550                 555                 560

Leu Ala Ser His Lys Thr Val His Thr Gly Glu Lys Pro Tyr Arg Cys
                565                 570                 575

Asn Ile Cys Gly Ala Gln Phe Asn Arg Pro Ala Asn Leu Lys Thr His
            580                 585                 590

Thr Arg Ile His Ser Gly Glu Lys Pro Tyr Lys Cys Glu Thr Cys Gly
            595                 600                 605

Ala Arg Phe Val Gln Val Ala His Leu Arg Ala His Val Leu Ile His
610                 615                 620

Thr Gly Glu Lys Pro Tyr Pro Cys Glu Ile Cys Gly Thr Arg Phe Arg
625                 630                 635                 640

His Leu Gln Thr Leu Lys Ser His Leu Arg Ile His Thr Gly Glu Lys
                645                 650                 655

Pro Tyr His Cys Glu Lys Cys Asn Leu His Phe Arg His Lys Ser Gln
            660                 665                 670

Leu Arg Leu His Leu Arg Gln Lys His Gly Ala Ile Thr Asn Thr Lys
            675                 680                 685
```

```
Val Gln Tyr Arg Val Ser Ala Thr Asp Leu Pro Pro Glu Leu Pro Lys
    690                 695                 700

Ala Cys
705
```

UNITED STATES PATENT AND TRADEMARK OFFICE
CERTIFICATE OF CORRECTION

| | | |
|---|---|---|
| PATENT NO. | : 11,371,989 B2 | Page 1 of 1 |
| APPLICATION NO. | : 16/195586 | |
| DATED | : June 28, 2022 | |
| INVENTOR(S) | : Cantor et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 506 days.

Signed and Sealed this
Tenth Day of June, 2025

Coke Morgan Stewart
*Acting Director of the United States Patent and Trademark Office*